US007265144B2

(12) United States Patent
Rudolph et al.

(10) Patent No.: US 7,265,144 B2
(45) Date of Patent: Sep. 4, 2007

(54) ANILINOPYRAZOLE DERIVATIVES USEFUL FOR THE TREATMENT OF DIABETES

(75) Inventors: Joachim Rudolph, Guilford, CT (US); Louis-David Cantin, Hamden, CT (US); Steven Magnuson, Wallingford, CT (US); William Bullock, Easton, CT (US); Ann-Marie Bullion, Milford, CT (US); Libing Chen, Milford, CT (US); Chih-Yuan Chuang, New Haven, CT (US); Sidney Liang, Bethany, CT (US); Dyuti Majumdar, Milford, CT (US); Herbert Ogutu, Hamden, CT (US); Alan Olague, Shelton, CT (US); Ning Qi, Hamden, CT (US); Philip L. Wickens, Wallingford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 447 days.

(21) Appl. No.: 10/719,485

(22) Filed: Nov. 21, 2003

(65) Prior Publication Data

US 2004/0157904 A1 Aug. 12, 2004

Related U.S. Application Data

(60) Provisional application No. 60/498,214, filed on Aug. 27, 2003, provisional application No. 60/429,917, filed on Nov. 27, 2002.

(51) Int. Cl.
*A61K 31/4152* (2006.01)
*C07D 231/44* (2006.01)

(52) U.S. Cl. .................................... 514/406; 548/367.4

(58) Field of Classification Search ................ 514/406; 548/367.4
See application file for complete search history.

(56) References Cited

U.S. PATENT DOCUMENTS

| | | | |
|---|---|---|---|
| 3,257,410 | A | 6/1966 | Putter et al. |
| 3,790,576 | A | 2/1974 | DeWald |
| 5,916,908 | A | 6/1999 | Giese et al. |
| 5,942,520 | A | 8/1999 | Pamukcu et al. |
| 5,998,424 | A | 12/1999 | Galemmo et al. |

FOREIGN PATENT DOCUMENTS

| | | |
|---|---|---|
| DE | 1143515 | 2/1963 |
| WO | 9319054 | 9/1993 |
| WO | 9614843 | 5/1996 |
| WO | 9708149 | 3/1997 |
| WO | 9964407 | 12/1999 |

OTHER PUBLICATIONS

Menzel, et al., "Synthesen und Reaktionen neuer ortho-kondensierter Pyrazoloverbindungen," Angew. Chem., 74 (21), 839-847 (1962).

Crenshaw, et al., "Interferon Inducing Activities of Derivatives of 1,3-Dimethyl-4-(3-dimethylaminopropylamino)-1 *H*-pyrazolo[3,4-*b*]quinoline and Related Compounds," J. Med. Chem, 19(2), 262-275 (1976).

Catarzi, et al., "Tricyclic Heteroaromatic Systems. Synthesis and $A_1$ and $A_{2a}$ Adenosine Binding Activities of Some 1-Aryl-1,4-dihydro-3-methyl[1]benzopyrano[2,3-*c*]pyrazol-4-ones, 1-Aryl-4,9-dihydro-3-methyl-1*H*-pyrazolo[3,4-*b*]quinolin-4-ones, and 1-Aryl-1 *H*-imidazo[4,5-*b*]quinoxalines," J. Med. Chem., 38, 1330-1336 (1995).

*Primary Examiner*—Kamal A. Saeed

(57) ABSTRACT

The present invention relates to anilinopyrazole compounds, pharmaceutical compositions, and methods for treating diabetes and related disorders.

40 Claims, No Drawings

ANILINOPYRAZOLE DERIVATIVES USEFUL FOR THE TREATMENT OF DIABETES

This application claims benefit of U.S. Provisional Application Ser. No. 60/429,917, filed Nov. 27, 2002, and U.S. Provisional Application Ser. No. 60/498,214, filed on Aug. 27, 2003, the contents of which are incorporated herein by reference in their entirety.

FIELD OF THE INVENTION

The present invention relates to anilinopyrazole compounds, pharmaceutical compositions, and methods for treating diabetes and related disorders.

BACKGROUND OF THE INVENTION

Diabetes is characterized by impaired glucose metabolism manifesting itself among other things by an elevated blood glucose level in the diabetic patient. Underlying defects lead to a classification of diabetes into two major groups. Type 1 diabetes, or insulin dependent diabetes mellitus (IDDM), arises when patients lack insulin-producing beta-cells in their pancreatic glands. Type 2 diabetes, or non-insulin dependent diabetes mellitus (NIDDM), occurs in patients with impaired beta-cell function and alterations in insulin action.

The current treatment for type 1 diabetic patients is injection of insulin, while the majority of type 2 diabetic patients are treated with agents that stimulate beta-cell function or with agents that enhance the tissue sensitivity of the patients towards insulin. The drugs presently used to treat type 2 diabetes include alpha-glucosidase inhibitors, insulin sensitizers, insulin secretagogues, and metformin.

Over time, almost one-half of type 2 diabetic subjects lose their response to these agents. Insulin treatment is instituted after diet, exercise, and oral medications have failed to adequately control blood glucose. The drawbacks of insulin treatment are the need for drug injection, the potential for hypoglycemia, and weight gain.

Because of the problems with current treatments, new therapies to treat type 2 diabetes are needed. In particular, new treatments to retain normal (glucose-dependent) insulin secretion are needed. Such new drugs should have the following characteristics: dependency on glucose for promoting insulin secretion (i.e., compounds that stimulate insulin secretion only in the presence of elevated blood glucose); low primary and secondary failure rates; and preservation of islet cell function.

INS-1 cells are a model for islet beta-cell insulin secretion. When maintained in the presence of beta-mercaptoethanol, these cells retain many of the characteristics of islet beta-cells in situ. The cells secrete insulin in response to physiologically relevant glucose concentrations with an $EC_{50}$ of 6 mM glucose (Hohmeier, et al., Diabetes 49:424, 2002). These cells also secrete insulin in response to multiple known secretagogues, including agents that elevate intracellular cyclic AMP, nutrients other than glucose, and potassium chloride. This characteristic of INS-1 cells further demonstrates that the cells retain many of the signaling pathways that are involved in the insulin secretory response, and as such are suitable for identifying compounds that affect these pathways. INS-1 cells are therefore useful tools for identifying compounds that stimulate insulin secretion in the presence of glucose and thus useful in the treatment of diabetes and related disorders.

DETAILED DESCRIPTION OF THE INVENTION

The invention provides anilinopyrazole derivatives of Formula (I)

(I)

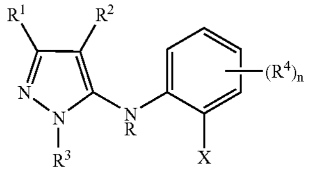

wherein

R is H or $(C_1-C_6)$alkyl;

$R^1$ is H,

- $(C_1-C_6)$alkyl optionally substituted with one substituent selected from the group consisting of $(C_1-C_4)$alkoxy, phenyl optionally substituted with halo, and [tri$(C_1-C_4)$alkyl]silyl,
- $(C_3-C_6)$alkenyl,
- $(C_3-C_6)$alkynyl,
- $(C_3-C_6)$cycloalkyl optionally substituted with up to two substituents selected from the group consisting of $(C_1-C_3)$alkyl, $CF_3$, and halo,
- $(C_1-C_3)$haloalkyl, or
- phenyl optionally substituted with up to four substituents selected from the group consisting of
  - halo,
  - $(C_1-C_6)$alkyl optionally substituted with one $(C_1-C_4)$alkoxy,
  - $(C_1-C_6)$alkoxy,
  - $(C_1-C_3)$haloalkyl,
  - $(C_1-C_3)$haloalkoxy,
  - $NR^8R^8$,
  - cyano, and
  - $(C_1-C_6)$alkylthio;

$R^2$ is H,

- halo,
- $(C_1-C_6)$alkyl optionally substituted with one $(C_1-C_4)$alkoxy,
- $(C_3-C_6)$cycloalkyl optionally substituted with up to two substituents selected from the group consisting of $(C_1-C_3)$alkyl and halo,
- $(C_1-C_3)$haloalkyl,
- pyridyl optionally substituted with up to two substituents selected from the group consisting of $(C_1-C_6)$alkoxy, $(C_1-C_6)$alkythio, halo, and $(C_1-C_6)$alkyl optionally substituted with one $(C_1-C_4)$alkoxy,
- pyrimidyl,
- phenyl optionally substituted with up to four substituents selected from the group consisting of
  - $(C_1-C_6)$alkyl optionally substituted with one $(C_1-C_4)$alkoxy,
  - $(C_1-C_6)$alkoxy,
  - hydroxy,
  - $NR^8R^8$,
  - cyano,
  - $(C_1-C_6)$alkylthio,
  - halo,
  - $CO_2R^8$,
  - $(C_1-C_3)$haloalkoxy,
  - $(C_1-C_4)$acyl, and benzoyl, or tetrahydronaphthyl, indanyl, benzodioxolyl, or benzodioxanyl, each of which may be optionally substituted with up to two substituents selected from the group consisting of $(C_1-C_6)$alkoxy, $(C_1-C_6)$alkythio, halo, and $(C_1-C_6)$alkyl optionally substituted with one $(C_1-C_4)$ alkoxy, or when $R^1$ and $R^2$ are $(C_1-C_6)$alkyl, they may, together with C atoms to which they are attached, form a 5- or 6-membered carbocyclic ring, or $R^1$ and $R^2$ may, together with the C atoms to which they are attached form a 6-membered heterocyclic ring containing a N atom and optionally substituted on N with $(C_1-C_3)$ alkyl;

$R^3$ is $(C_1-C_6)$alkyl, $(C_3-C_6)$cycloalkyl, benzyl optionally substituted on the aryl ring with up to four substituents selected from the group consisting of $(C_1-C_6)$alkyl optionally substituted with one $(C_1-C_4)$ alkoxy, halo, $(C_1-C_3)$haloalkyl, $(C_1-C_6)$alkoxy, $(C_1-C_3)$haloalkoxy, $NR^8R^8$, cyano, $(C_1-C_6)$alkylthio, and $SO_2(C_1-C_3)$alkyl, $(C_2-C_3)$haloalkyl, or phenyl optionally substituted with up to four substituents selected from the group consisting of $(C_1-C_6)$alkyl optionally substituted with one $(C_1-C_4)$ alkoxy, halo, $(C_1-C_3)$haloalkyl, $(C_1-C_6)$alkoxy, $(C_1-C_3)$haloalkoxy $NR^8R^8$, cyano, $(C_1-C_6)$alkylthio, and $SO_2(C_1-C_3)$alkyl;

$R^4$ is $(C_1-C_6)$alkyl optionally substituted with one $(C_1-C_4)$ alkoxy, $(C_1-C_6)$alkoxy, $(C_1-C_6)$alkylthio, $(C_1-C_3)$haloalkyl, $(C_1-C_3)$haloalkoxy, halo, $NR^8R^8$, pyrimidyl, pyridyl, imidazolyl, or phenyl optionally substituted with up to four substituents selected from the group consisting of halo, $(C_1-C_6)$alkyl optionally substituted with one $(C_1-C_4)$ alkoxy, $(C_1-C_6)$alkoxy, $(C_1-C_3)$haloalkyl, $(C_1-C_3)$haloalkoxy, $NR^8R^8$, cyano, and $(C_1-C_6)$alkylthio;

n=0, 1, 2, or 3;

X is $CO_2R^8$, $CONR^5R^6$, $SO_2NHR^7$, or oxadiazolyl optionally substituted with $(C_1-C_6)$alkyl;

$R^5$ is H, $(C_1-C_6)$alkyl, $(C_2-C_6)$alkyl substituted with $OR^6$, benzyl optionally substituted on the aryl ring with up to four substituents selected from the group consisting of halo, $(C_1-C_6)$alkyl optionally substituted with one $(C_1-C_4)$ alkoxy, $(C_1-C_6)$alkoxy, $(C_1-C_3)$haloalkyl, $(C_1-C_3)$haloalkoxy, $NR^8R^8$, cyano, and $(C_1-C_6)$alkylthio, phenyl optionally substituted with up to four substituents selected from the group consisting of $(C_1-C_6)$alkyl optionally substituted with one $(C_1-C_4)$ alkoxy, halo, $(C_1-C_6)$alkoxy, $(C_1-C_3)$haloalkyl, $(C_1-C_3)$haloalkoxy, $NR^8R^8$, cyano, and $(C_1-C_6)$alkylthio, pyridyl optionally substituted with up to two substituents selected from the group consisting of halo, $(C_1-C_6)$alkyl optionally substituted with one $(C_1-C_4)$ alkoxy, $(C_1-C_6)$alkoxy, $(C_1-C_3)$haloalkoxy, $NR^8R^8$, cyano, and $(C_1-C_6)$alkylthio,

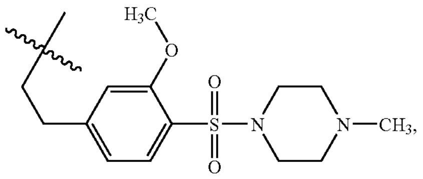

or $SO_2$-phenyl said phenyl optionally substituted with up to four substituents selected from the group consisting of halo $(C_1-C_6)$alkyl optionally substituted with one $(C_1-C_4)$ alkoxy, $(C_1-C_6)$alkoxy, $(C_1-C_3)$haloalkyl, $(C_1-C_3)$haloalkoxy, $NR^8R^8$, cyano, and $(C_1-C_6)$alkylthio;

$R^6$ is H or $(C_1-C_6)$alkyl;

or $R^5$ and $R^6$ together with N atom to which they are attached, may form a piperidine, morpholine, thiomorpholine, or piperazine ring said piperazine optionally substituted on N with $(C_1-C_3)$alkyl;

$R^7$ is H or methyl;

$R^8$ is H, $(C_1-C_6)$alkyl, benzyl optionally substituted on the aryl ring with up to four substituents selected from the group consisting of halo, $(C_1-C_6)$alkyl optionally substituted with one $(C_1-C_4)$ alkoxy, $(C_1-C_3)$alkoxy, $(C_1-C_3)$haloalkyl, $(C_1-C_3)$haloalkoxy, cyano, and $(C_1-C_6)$alkylthio, or phenyl optionally substituted with up to four substituents selected from the group consisting of $(C_1-C_6)$alkyl optionally substituted with one $(C_1-C_4)$ alkoxy, halo, $(C_1-C_6)$alkoxy, $(C_1-C_3)$haloalkyl, $(C_1-C_3)$haloalkoxy, cyano, and $(C_1-C_6)$alkylthio;

and the pharmaceutically acceptable salts thereof;

provided that when R and $R^2$ are H and X is $CO_2H$, then $R_1$ is not H, methyl, or ethyl, and further provided that the Formula (I) compound is not

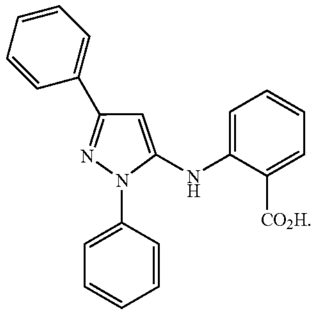

The terms identified above have the following meaning throughout:

The term "halo" means F, Br, Cl, and I.

The terms "$(C_1-C_3)$alkyl," "$(C_1-C_6)$alkyl," and "$(C_2-C_6)$ alkyl" mean a linear or branched saturated hydrocarbon radical having from about 1 to about 3 C atoms, about 1 to about 6 C atoms, about 2 to about 6 C atoms, respectively. Such groups include, but are not limited to, methyl, ethyl, n-propyl, isopropyl, butyl, isobutyl, pentyl, hexyl, and the like.

The term "$(C_3-C_6)$alkenyl" means a linear or branched unsaturated hydrocarbon radical containing a double bond and from about 3 to about 6 carbon atoms. The double bond may be between any two available carbon atoms in the chain. Such groups include, allyl, isopropenyl, 2-butenyl, 2-ethyl-2-butenyl, 1-hexenyl, and the like.

The term "$(C_3-C_6)$alkynyl" means a linear or branched unsaturated hydrocarbon radical containing a triple bond and from about 3 to about 6 carbon atoms. The triple bond may be between any two available carbon atoms in the chain. Such groups include, propargyl, 2-butynyl, 1-methyl-2-butynyl, 3-hexynyl, and the like.

The term "$(C_3-C_6)$cycloalkyl" includes cyclopropyl, cyclobutyl, cyclopentyl, and cyclohexyl.

The terms "$(C_1-C_3)$alkoxy," "$(C_1-C_4)$alkoxy," and "$(C_1-C_6)$alkoxy" mean a linear or branched saturated hydrocarbon radical having from about 1 to about 3 C atoms, about 1 to about 4 C atoms, or about 1 to about 6 C atoms, respectively, said radical being attached to an O atom. The O atom is the atom through which the alkoxy substituent is attached to the rest of the molecule. Such groups include, but are not limited to, methoxy, ethoxy, n-propoxy, isopropoxy, butoxy, pentyloxy, hexyloxy, and the like.

The terms "$(C_1-C_3)$haloalkoxy" and "$(C_2-C_3)$haloalkoxy" mean a $(C_1-C_3)$alkoxy group or a $(C_2-C_3)$alkoxy group, respectively, substituted on C with a halogen atom. Such groups include trifluoromethoxy, difluoromethoxy, 2,2-difluoroethoxy, 2,2,2-trifluoroethoxy, 2-chloroethoxy, 3-chloropropoxy, 1-fluoro-2,2,-dichloroethoxy, and the like.

The terms "$(C_1-C_3)$haloalkyl" and "$(C_2-C_3)$haloalkyl" mean a $(C_1-C_3)$alkyl group or $(C_2-C_3)$alkyl group substituted on C with a halogen atom. Such groups include trifluoromethyl, difluoroethyl, 1-fluoro-2,2-dichloroethyl, 3-chloropropyl, 4-bromohexyl, and the like.

The term "[tri$(C_1-C_4)$alkylsilyl]" means a Si radical bearing three $(C_1-C_4)$alkyl substituents, each substituent being independently selected. The Si atom is the atom through which the radical is attached to the rest of the molecule. Such groups include, but are not limited to, trimethylsilyl, tert-butyl-dimethylsilyl, and the like.

The formula C(O) means a radical in which the C atom bears a doubly bonded oxygen, (an oxo substituent) and in which there remains two additional binding sites, that is, represents a radical of the formula:

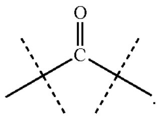

The term "$(C_1-C_4)$acyl" means a $(C_1-C_4)$alkyl radical substituted on the C of a C(O) group. The C of the C(O) is the group is also the atom through which the substituent is attached to the rest of the molecule. Such groups include, but are not limited to, acetyl ($CH_3C(O)—$), n-propanoyl ($CH_3CH_2C(O)—$), isobutanoyl [$(CH_3)_2CHC(O)—$], and the like.

The formula "$NR^8R^8$" means that each of the two possible $R^8$ groups attached to the N atom are selected independently from the other so that they may be the same or they may be different.

The terms "$(C_1-C_3)$alkylthio" and "$(C_1-C_6)$alkylthio" mean a linear or branched saturated hydrocarbon radical having from about 1 to about 3 C atoms, or about 1 to about 6 C atoms, respectively, said radical being attached to an S atom. The S atom is the atom through which the alkylthio substituent is attached to the rest of the molecule. Such groups include, but are not limited to, methylthio, ethylthio, n-propylthio, isopropylthio, and the like.

The term "$SO_2(C_1-C_3)$alkyl" means a linear or branched saturated hydrocarbon radical having from about 1 to about 3 C atoms, said radical being attached to the S atom of the $SO_2$ group. The S atom of the $SO_2$ group is the atom through which the $SO_2(C_1-C_3)$alkyl substituent is attached to the rest of the molecule. Such groups include methylsulfonyl, ethylsulfonyl, n-propylsulfonyl and isopropylsulfonyl, and the like.

The term "6-membered carbocyclic ring" means a partially unsaturated ring containing C atoms fused to the pyrazole ring to form a tetrahydroindazole ring system. The ring may be optionally substituted with ($C_1$-$C_6$)alkyl groups at any available position, up to a total of about 6 C atoms.

The term "6-membered heterocyclic ring containing an N atom and substituted on N with ($C_1$-$C_3$)alkyl" means a heterocyclic ring fused to the pyrazole ring to form either a tetrahydropyrazolo[4,3-c]pyridine or tetrahydropyrazolo[3,4-c]pyridine bicyclic ring system. The N atom of the tetrahydropyridine heterocycle is located at either the 5 or 6-position of the bicyclic system, as illustrated below. The N atom may be optionally substituted (indicated as $R^{opt\ sub}$ in the illustration below), with ($C_1$-$C_3$)alkyl.

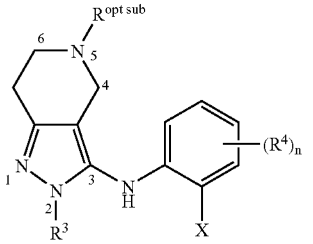

tetrahydropyrazolo[4,3-c]pyridine

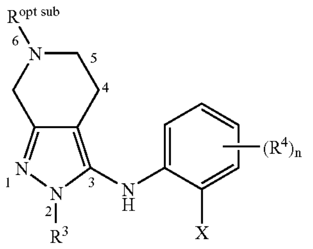

tetrahydropyrazolo[3,4-c]pyridine

The terms "tetrahydronaphthyl," "indanyl," "benzodioxolyl," or "benzodioxanyl" mean bicyclic ring radicals of the formulae

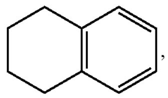 , 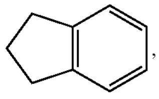 ,

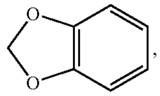 , and 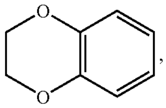 , respectively. The radical is attached to the rest of the molecule at any available carbon of the phenyl ring. Where the radical is optionally substituted, the substituent may be attached at any available carbon atom.

The term "optionally substituted" means that the moiety so modified may have from none to up to at least the highest number of substituents indicated. Each substituent may replace any H atom on the moiety so modified as long as the replacement is chemically possible and chemically stable. When there are two or more substituents on any moiety, each substituent is chosen independently of any other substituent and can, accordingly, be the same or different.

Alternative Forms Of Novel Compounds

Also included in the compounds of the present invention are (a) the stereoisomers thereof, (b) the pharmaceutically-acceptable salts thereof, (c) the tautomers thereof, (d) the protected acids and the conjugate acids thereof, and (e) the prodrugs thereof.

The stereoisomers of these compounds may include, but are not limited to, enantiomers, diastereomers, racemic mixtures, and combinations thereof. Such stereoisomers may be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the inhibitors described above.

Pharmaceutically-acceptable salts of the compounds of the present invention include salts commonly used to form alkali metal salts or form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, heterocyclic, carboxylic, and sulfonic classes of organic acids. Examples of organic and sulfonic classes of organic acids includes, but are not limited to, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicylic, galactaric, and galacturonic acid, and combinations thereof.

Tautomers of the compounds of the invention are encompassed by the present invention. Thus, for example, a carbonyl includes its hydroxy tautomer.

The protected acids include, but are not limited to, esters, hydroxyamino derivatives, amides and sulfonamides.

The present invention includes the prodrugs and salts of the prodrugs. Formation of prodrugs is well known in the art in order to enhance the properties of the parent compound; such properties include solubility, absorption, biostability, and release time (see, e.g., "*Pharmaceutical Dosage Form and Drug Delivery Systems*" (Sixth Edition), edited by Ansel et al., publ. by Williams & Wilkins, pgs. 27-29, (1995), which is hereby incorporated by reference). Commonly used prodrugs are designed to take advantage of the major drug biotransformation reactions, and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation, and acetylation (see, e.g., *Goodman and Gilman's The Pharmacological Basis of Therapeutics* (Ninth Edition), editor Molinoff et al., publ. by McGraw-Hill, pages 11-13, (1996), which is hereby incorporated by reference).

A comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87.

General Preparative Methods

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention.

Reaction Scheme A illustrates the general method for the preparation of the Formula (Ia) [Formula (I) where R is H] compounds. An aminopyrazole of Formula (III) is coupled with either a 2-bromo or 2-iodobenzoic acid, benzoic ester, benzoic acid amide, or benzenesulfonamide of Formula (IV), using Ullmann-type conditions (copper (II) acetate in DMF, heated in a sealed tube for 16 h) or a 2-bromobenzoic ester, benzoic acid amide, or benzenesulfonamide of Formula (IV) using Buchwald-type conditions (cesium carbonate, BINAP and $Pd_2(dba)_3$ in anhydrous toluene, heated to 110° C. for 16 h under argon).

Reaction Scheme A

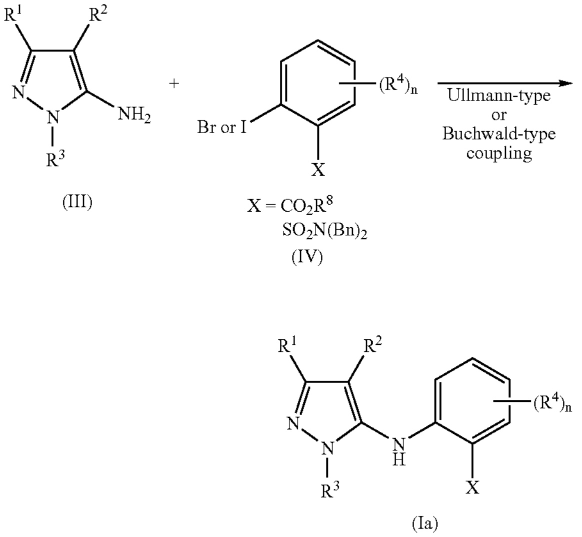

(III)

X = $CO_2R^8$
$SO_2N(Bn)_2$
(IV)

(Ia)

Reaction Scheme B illustrates a general method for conversion of compounds of Formula (Ib) into other Formula (Ia) compounds having at least one $R^4$ substituent, by reaction of the halogen-containing (Ib) under Suzuki coupling conditions [e.g., a palladium catalyst such as Pd(dppf) $Cl_2$, and a boronic acid (V)].

Reaction Scheme B

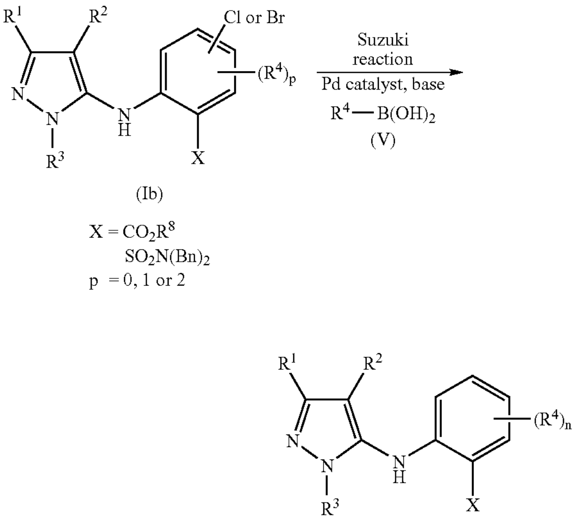

(Ib)

X = $CO_2R^8$
$SO_2N(Bn)_2$
p = 0, 1 or 2

(Ia)
n = 1, 2 or 3

Reaction Scheme C outlines a general method for the preparation of other Formula (Ia) compounds from compounds of Formula (Id) [Formula (I) where $R^2$ is bromo or iodo]. In this scheme, a bromine or iodine is introduced to the compound of Formula (Ic) [Formula (I) where $R^2$ is H] and the resulting Formula (Id) compound is allowed to undergo a Suzuki reaction with a boronic acid $R^2B(OH)_2$.

Reaction Scheme C

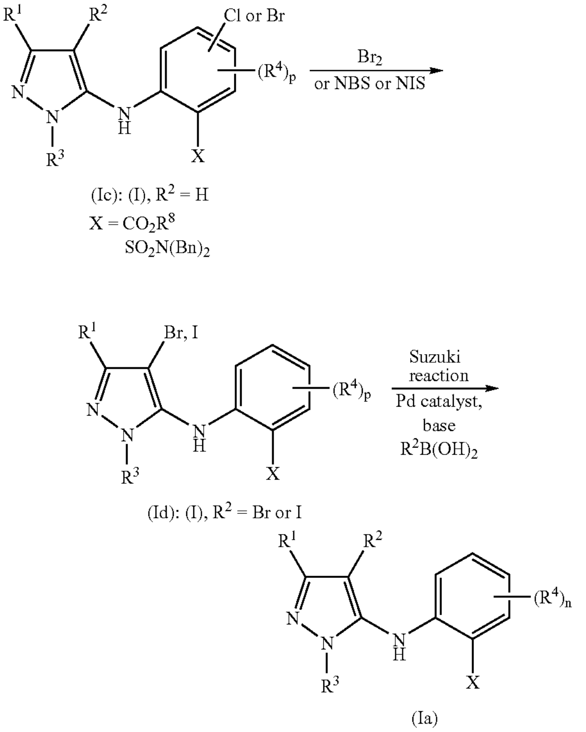

(Ic): (I), $R^2$ = H
X = $CO_2R^8$
$SO_2N(Bn)_2$ (Id): (I), $R^2$ = Br or I (Ia)

By combining the methods of Reaction Schemes A, B, and C, Formula (Ia) compounds may be prepared containing a variety of $R^2$ and $R^4$ substituents as shown in Reaction Scheme D1. For example, coupling a dibromobenzoic acid, dibromobenzoic ester, or dibromobenzenesulfonamide of Formula (IVa) with a pyrazole of Formula (IIIa) provides an intermediate of Formula (Ie). Suzuki reaction of (Ie) with a boronic acid derivative gives (If) which can be brominated or iodinated to give (Id). Finally, (Id) can be converted to the Formula (Ia) compounds via another Suzuki reaction.

Reaction Scheme D1

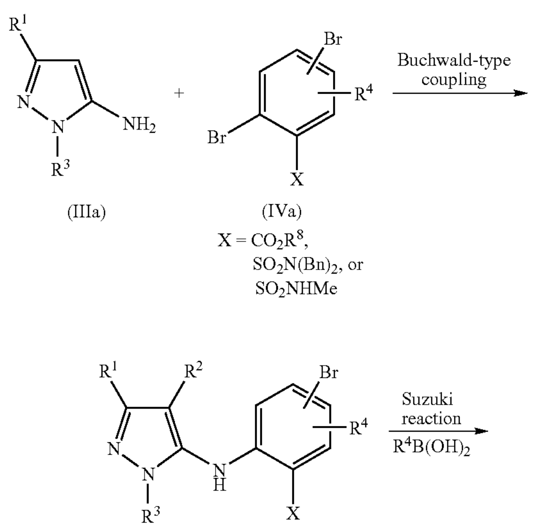

(IIIa)

(IVa)

X = $CO_2R^8$, $SO_2N(Bn)_2$, or $SO_2NHMe$ (Ie): (I), $R^2$ = H

-continued

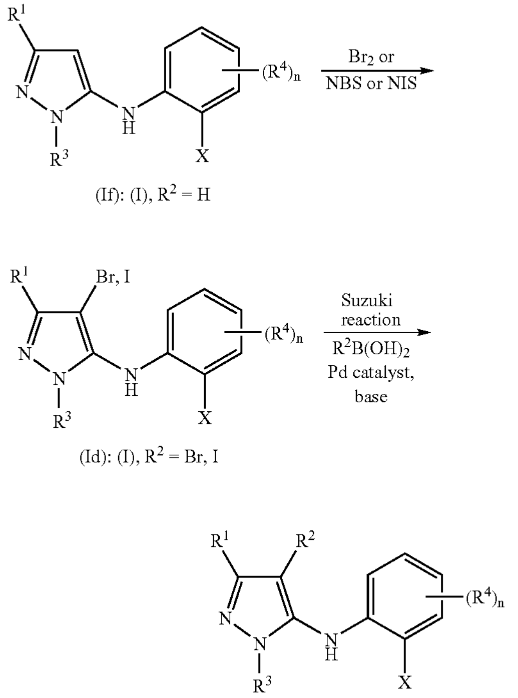

(If): (I), $R^2$ = H (Id): (I), $R^2$ = Br, I (Ia)

Other compounds of Formula (I) where $R^2$ is iodo (Formula Ig) or fluoro (Formula Ih) may be prepared from Formula (If) compounds as shown in Reaction Scheme D2, by iodination with NIS or fluorination with Selectfluor®, respectively.

Reaction Scheme D2

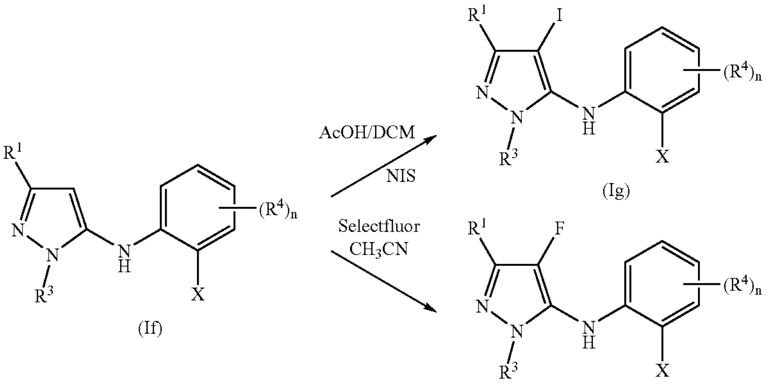

(If)

(Ig)

(Ih)

Compounds of Formula (I) in which $R^4$ is an amino group $NR^5R^6$ or imidazole can be prepared by a special sequence outlined in Reaction Scheme E.

Reaction Scheme E

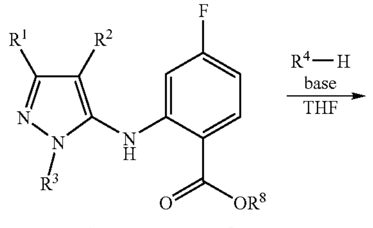

(Ij): $R^4$ = 4-F; X = $CO_2R^8$

-continued

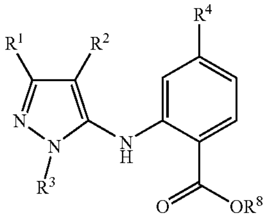

(Ik): $R^4 = NR^5R^6$ or imidazol-1-yl
X = $CO_2R^8$

In this sequence, a 4-fluoro group on the phenyl ring can be displaced by an $R^4$ group, where $R^4$=$NR^5R^6$ or an imidazolyl, in an aromatic nucleophilic substitution reaction. The reaction is conducted in the presence of a base such as $LiNMe_2$ or $K_2CO_3$, Compounds of Formula (I) where X is $C(O)NR^5R^6$ or oxadiazolyl can be prepared by the route described in Reaction Scheme F.

Reaction Scheme F

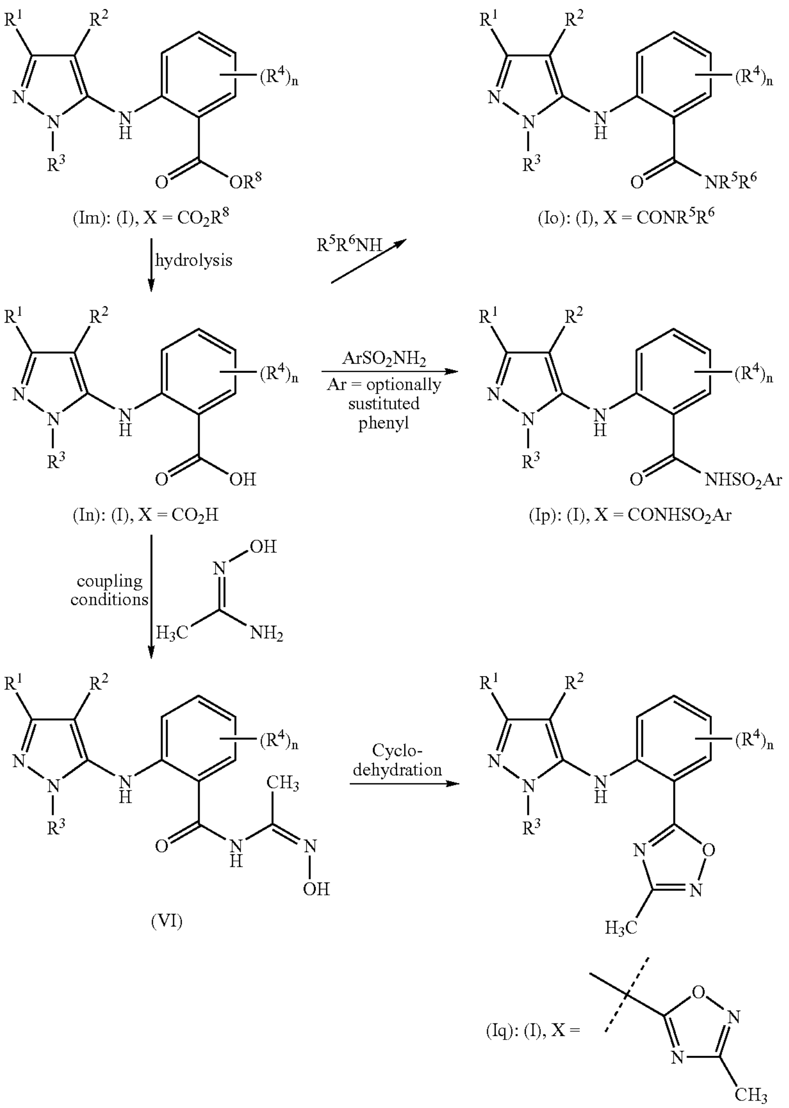

(Im): (I), X = $CO_2R^8$ (Io): (I), X = $CONR^5R^6$ (In): (I), X = $CO_2H$ (Ip): (I), X = $CONHSO_2Ar$ (VI)

(Iq): (I), X =

An ester compound of Formula (Im) is hydrolyzed to the acid compound of Formula (In) usually in mild aqueous base. Formula (In) can then be converted to amides of Formula (Io) by reaction with an amine $R^5R^6NH$ and a coupling agent, or with an optionally substituted phenyl sulfonamide $ArSO_2NH_2$ and a coupling agent, to give the acyl sulfonamide of Formula (Ip). The Formula (In) compound may also be converted to the Formula (Iq) compound by reaction with an N-hydroxy-acetamidine facilitated by base such as triethylamine and coupling agents such as HOAT and EDCI. The oxadiazole ring in Formula (Iq) is formed when the Formula (VI) compound is subjected to cyclodehydration conditions such as the addition of (methoxycarbonylsulfamoyl)-triethylammonium hydroxide (Burgess reagent).

Reaction Scheme G outlines the general method for preparation of Formula (I) compounds in which X=$SO^2NHR^7$ and $R^7$ is H.

Reaction Scheme G

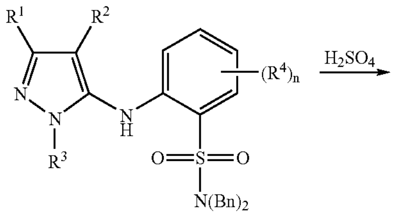

(Ir): (I), X = $SO_2N(Bn)_2$

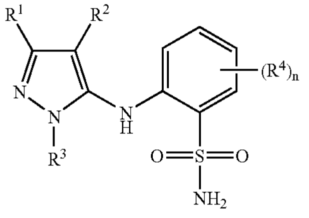

(Is): (I), X = $SO_2NH_2$

The N,N-dibenzylsulfonamide compound of Formula (Ir) is prepared as described in Reaction Scheme A and can be de-benzylated with sulfuric acid to give the compound of Formula (Is).

Reaction Scheme G

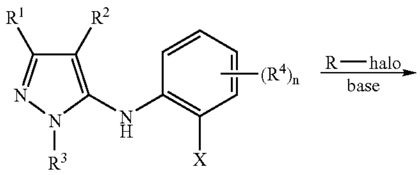

(Ia)

-continued

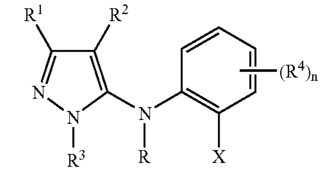

(I)

halo = Br, I, Cl
R = $(C_1\text{-}C_6)$alkyl

The compounds of Formula (I) where R is $(C_1\text{-}C_6)$alkyl are prepared by N-alkylation of the corresponding Formula (I) compounds where R is H, using standard conditions such as those shown in Reaction Scheme H. Such conditions include an alkylating agent such as iodomethane, and a base such as sodium hydride, and the reaction is carried out in inert solvent such as DMF.

Synthesis of Intermediates

Intermediates are either commercially available, or are prepared by standard methods known in the art and/or by analogy to one of the procedures shown below.

5-Aminopyrazoles

5-Aminopyrazole starting materials of Formula (III) are either commercially available or can be prepared as shown in Reaction Schemes I, J, or K.

Reaction Scheme I

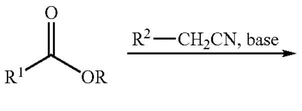

(VII)

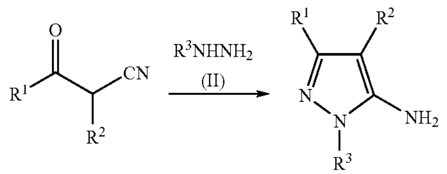

(VIII) (III)

In Reaction Scheme I, condensation of an optionally substituted acetonitrile with an appropriately substituted ester (VII), and base, gives the cyanoketone (VIII). Esters of Formula (VII) where $R^1$ is an optionally substituted phenyl, can be prepared, if necessary, from the corresponding bromo compound of Formula $R^1$—Br, for example, by reaction with BuLi and $CO_2$ to form an acid of Formula $R^1$—COOH, which can be esterified to (VII). The compound of formula (VIII) is then allowed to react with a substituted hydrazine of Formula (II) to give the desired aminopyrazole (III). If the cyanoketone (VII) is commercially available, the first step is omitted.

Reaction Scheme J

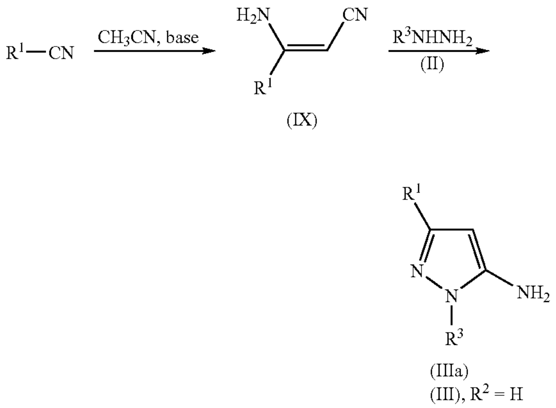

(IX)

(IIIa)
(III), $R^2$ = H

In Reaction Scheme J, acetonitrile is allowed to condense to the enaminonitrile (IX), then react with the hydrazine (II) to form (IIIa) [(III) where $R^2$=H].

and trimeric boronic acid esters such as

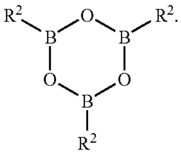

Reaction Scheme K illustrates how the aminopyrazole of Formula (IIIa) may be converted to other aminopyrazoles of Formula (III) by bromination and Suzuki or Stille coupling reactions to introduce an $R^2$ group other than H. The product of the Stille reaction (IIIc) can also be reduced, for example by hydrogenation, to give the saturated compound of Formula (IIId).

Examples of preparations of aminopyrazoles are shown in the descriptions of Intermediates B-M, below.

Hydrazines

Hydrazine starting materials of Formula (II) are either commercially available or, in the case of phenyl hydrazines Reaction Scheme K

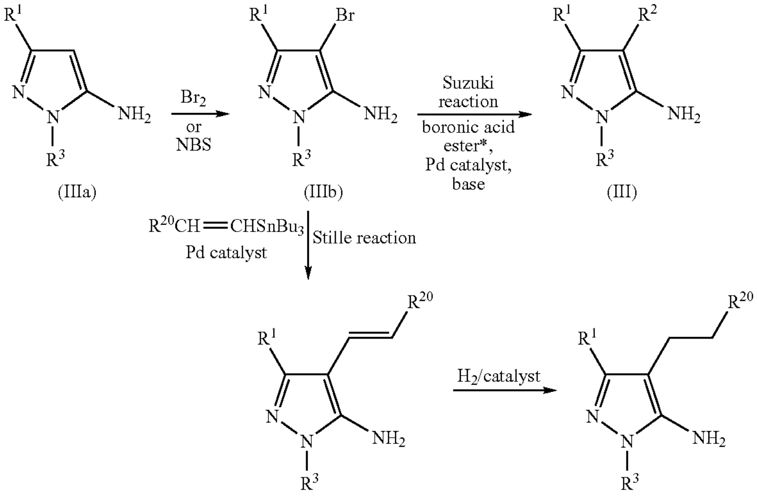

(IIIa) (IIIb) (III) (IIIc) (IIId)

$R^{20}$ is H, $(C_1-C_4)$ alkyl

*Suitable boronic acid esters include $R^2B(OR')_2$ where R' is a lower alkyl group, or two R' groups may form a ring such as

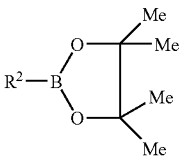

($R^3$=optionally substituted phenyl), can be prepared as shown in Reaction Scheme L.

Reaction Scheme L

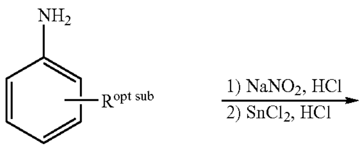

$R^{opt\ sub}$ = an optional substituent

-continued

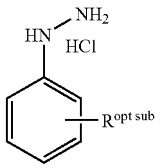

(IIa), [(II), $R^3$ = optionally substituted phenyl]

A substituted aniline is converted into a diazonium salt intermediate which is subsequently reduced using tin(II) chloride as the reductant.

An example of a preparation of an arylhydrazine is shown in the description of Intermediate A, below.

2-Bromobenzoic Acid Derivatives

The 2-bromobenzoic acid derivatives used in the coupling reactions with 5-aminopyrazoles were either commercially available or prepared by straightforward means well known in the art. An example of one such preparation is shown in the description of Intermediate N below.

Specific Examples of the Invention

The following specific examples are presented to illustrate the invention described herein, but should not be construed as limiting the scope of the invention in any way.

Abbreviations and Acronyms

When the following abbreviations are used throughout the disclosure, they have the following meaning:

| | |
|---|---|
| abs | absolute |
| Ac | acetyl |
| AcOH | acetic acid |
| amu | atomic mass unit |
| aq | aqueous |
| BINAP | 2,2'-Bis(diphenylphosphino)-1,1'-binaphthyl |
| Bn | benzyl |
| Boc | t-butoxycarbonyl |
| $BTMAICl_2$ | benzyltrimethylammonium dichloriodate |
| Bu | butyl |
| $CDCl_3$ | deuterochloroform |
| CDI | carbonyl diimidazole |
| Celite ® | brand of diatomaceous earth filtering agent, registered trademark of Celite Corporation |
| CI-MS | chemical ionization mass spectroscopy |
| conc | concentrated |
| d | doublet |
| DCM | dichloromethane |
| dd | doublet of doublet |
| ddd | doublet of doublet of doublet |
| DMAP | 4-(N,N-dimethyl)amino pyridine |
| DMF | N,N-dimethyl formamide |
| DMSO | dimethylsulfoxide |
| DMSO-$d_6$ | dimethylsulfoxide-$d_6$ |
| DOWEX ® 66 | Dowex hydroxide, weakly basic anion, macroporous, 25-50 mesh |
| dppf | 1,1'-bis(diphenylphosphino)ferrocene |
| EDCl | 1-(3-dimethylaminopropyl)-3-ethylcarbodiimide hydrochloride |
| EI | electron impact ionization |
| EI - MS | electron impact - mass spectrometry |
| equiv | equivalent |
| ES - MS | electrospray mass spectrometry |
| Et | ethyl |
| $Et_2O$ | diethyl ether |
| $Et_3N$ | triethylamine |
| EtOAc | ethyl acetate |
| EtOH | ethanol |
| g | gram |
| GC-MS | gas chromatography - mass spectrometry |
| h | hour(s) |

-continued

| | |
|---|---|
| Hex | hexanes |
| $^1H$ NMR | proton nuclear magnetic resonance |
| HOAT | 1-hydroxy-7-aza-benzotriazole |
| HOBT | 1-hydroxybenzotriazole |
| HPLC | high-performance liquid chromatography |
| HPLC ES-MS | high-performance liquid chromatography-electrospray mass spectroscopy |
| KOtBu | potassium tert-butoxide |
| L | liter |
| LC-MS | liquid chromatography/mass spectroscopy |
| LDA | lithium diisopropylamide |
| m | multiplet |
| M | molar |
| mL | milliliter |
| m/z | mass over charge |
| Me | methyl |
| MeCN | acetonitrile |
| MeOH | methanol |
| mg | milligram |
| MHz | megahertz |
| min | minute(s) |
| mmol | millimole |
| mol | mole |
| mp | melting point |
| MS | mass spectrometry |
| N | normal |
| NaOAc | sodium acetate |
| NBS | N-bromosuccinimide |
| NIS | N-iodosuccinimide |
| NMM | 4-methylmorpholine |
| NMR | nuclear magnetic resonance |
| $Pd_2(dba)_3$ | tris(dibenzylideneacetone)dipalladium(0) |
| $Pd(OAc)_2$ | palladium acetate |
| $Pd(PPh_3)_4$ | tetrakis(triphenylphosphine)palladium(0) |
| Pd/C | palladium on carbon |
| $Pd(dppf)Cl_2$ | [1,1'-bis(diphenylphosphino)ferrocene]dichloro-palladium(II) |
| Ph | phenyl |
| ppm | parts per million |
| Pr | propyl |
| psi | pounds per square inch |
| q | quartet |
| qt | quintet |
| $R_f$ | TLC retention factor |
| rt | room temperature |
| RT | retention time (HPLC) |
| s | singlet |
| TBAF | tetrabutylammonium fluoride |
| TBDMS | tert-butyldimethylsilyl |
| TBDMSCl | tert-butyldimethylsilyl chloride |
| TBS | tert-butyldimethylsilyl |
| TFA | trifluoroacetic acid |
| THF | tetrahydrofuran |
| TLC | thin layer chromatography |
| TMS | tetramethylsilane |
| v/v | volume per unit volume |
| vol | volume |
| w/w | weight per unit weight |

General Experimental Methods

Air and moisture sensitive liquids and solutions were transferred via syringe or cannula, and introduced into reaction vessels through rubber septa. Commercial grade reagents and solvents were used without further purification. The term "concentration under reduced pressure" refers to use of a Buchi rotary evaporator at approximately 15 mm of Hg. All temperatures are reported uncorrected in degrees Celsius (° C.). Thin layer chromatography (TLC) was performed on EM Science pre-coated glass-backed silica gel 60 A F-254 250 μm plates. Column chromatography (flash chromatography) was performed on a Biotage system using 32-63 micron, 60 A, silica gel pre-packed cartridges. Purification using preparative reversed-phase HPLC chromatography were accomplished using a Gilson 215 system, typically using a YMC Pro-C18 AS-342 (150×20 mm I.D.)

column. Typically, the mobile phase used was a mixture of $H_2O$ (A) and MeCN (B). The water could be mixed or not with 0.1% TFA. A typical gradient was:

| Time [min] | A: % | B: % | Flow [mL/min] |
|---|---|---|---|
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

Electron impact mass spectra (EI-MS) were obtained with a Hewlett Packard 5989A mass spectrometer equipped with a Hewlett Packard 5890 Gas Chromatograph with a J & W DB-5 column (0.25 μM coating; 30 m×0.25 mm). The ion source was maintained at 250° C. and spectra were scanned from 50-800 amu at 2 sec per scan.

High pressure liquid chromatography-electrospray mass spectra (LC-MS) were obtained using either a:

(A) Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% to 95% B over 3.5 minutes at a flow rate of 1.0 mL/min was used with an initial hold of 0.5 minutes and a final hold at 95% B of 0.5 minutes. Total run time was 6.5 minutes.

or (B) Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-800 amu over 1.5 seconds. ELSD (Evaporative Light Scattering Detector) data was also acquired as an analog channel. The eluents were A: 2% acetonitrile in water with 0.02% TFA, and B: 2% water in acetonitrile with 0.018% TFA. Gradient elution from 10% to 90% B over 3.5 minutes at a flow rate of 1.5 mL/min was used with an initial hold of 0.5 minutes and a final hold at 90% B of 0.5 minutes. Total run time was 4.8 minutes. An extra switching valve was used for column switching and regeneration.

Routine one-dimensional NMR spectroscopy was performed on 300/400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$ and 7.26 ppm for $CDCl_3$ for $^1H$ spectra, and 39.5 ppm for DMSO-$d_6$, 1.3 ppm for $CD_3CN$, 49.0 ppm for $CD_3OD$, 53.8 ppm for $CD_2Cl_2$ and 77.0 ppm for $CDCl_3$ for $^{13}C$ spectra.

Synthesis of Intermediates

Hydrazines

Intermediate A

Preparation of (2.6-dimethylphenyl) hydrazine hydrochloride

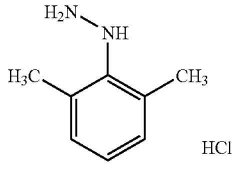

To a cold (0° C.) solution of 2,6-dimethylaniline (5.0 g, 41.3 mmol) in 50% aqueous HCl (45 mL), was added slowly under stirring a cold (0° C.) solution of $NaNO_2$ (2.85 g, 41.3 mmol) in water (22.5 mL). The temperature was closely monitored during the addition and was not allowed to exceed 5° C. Upon completion of the addition, the bright orange solution containing the diazonium salt intermediate was stirred at the same temperature for 20 min. A mixture of $SnCl_2$ (11.0 g, 57.8 mmol) in conc HCl (30 mL) was added to the reaction mixture at 0° C. over a period of ~5 min. The reaction mixture was then warmed to rt and stirred for 6 h. The precipitate was collected by filtration and washed with a small volume of cold water. Drying in vacuo afforded the title compound as a white amorphous solid (7.00 g, 98%). The product was used in the next step without further purification. ES-MS m/z 137.0 ($MH^+$); HPLC RT (min) 1.09.

5-Aminopyrazoles

Intermediate B

Preparation of 3-cyclopentyl-1-(2-methylphenyl)-1H-pyrazol-5-amine

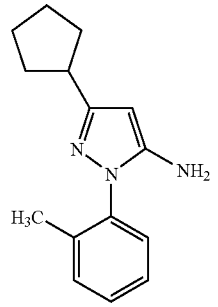

Step 1: Preparation of 3-cyclopentyl-3-oxoprolanenitrile

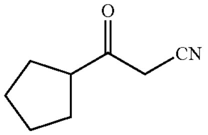

To a suspension of NaH (2.75 g, 68.7 mmol) in THF (15 mL) at 70° C. was added dropwise a solution of methyl cyclopentanecarboxylate (8.00 g, 62.4 mmol) and anhydrous acetonitrile (3.91 mL, 74.9 mmol) in THF (5 mL). The mixture was stirred for 16 h at 70° C.-72° C., cooled to rt, and diluted with ethyl acetate and aqueous HCl. The organic layer was washed with water and brine and dried ($MgSO_4$). Removal of the solvent provided 3-cyclopentyl-3-oxopropanenitrile, which was used without further purification.

Step 2: Preparation of 3-cyclopentyl-1-(2-methylphenyl)-1H-pyrazol-5-amine

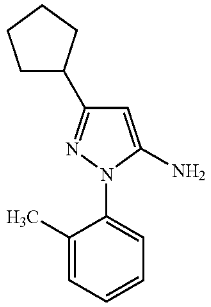

A solution of (2-methylphenyl)hydrazine hydrochloride (2.00 g, 14.6 mmol) and crude 3-cyclopentyl-3-oxopropanenitrile from the previous step (2.32 g, ~14.6 mmol) in toluene (6 mL) was heated to reflux for 16 h. Removal of the solvent under reduced pressure provided a residue which was purified by silica gel chromatography using hexane/EtOAc (3:1, v/v) as the eluent. Concentration under reduced pressure provided 3-cyclopentyl-1-(2-methylphenyl)-1H-pyrazol-5-amine as a light orange solid (2.19 g, 62%). ES-MS m/z 241.9 ($MH^+$); HPLC RT (min) 1.69. $^1$H NMR (400 MHz, $CDCl_3$) δ 1.58-1.82 (m, 6H), 2.00-2.16 (m, 2H), 2.17-2.21 (s, 3H), 2.93-3.11 (m, 1H), 3.42-3.58 (s, 2H), 5.41-5.46 (s, 1H), 7.20-7.28 (m, 2H) 7.29-7.37 (m, 2H).

Intermediate C

Preparation of 3-tert-butyl-1-(2-methylphenyl)-1H-pyrazol-5-amine

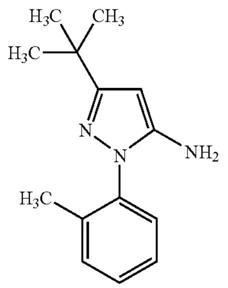

4,4-Dimethyl-3-oxopentanenitrile (36.7 g, 0.29 mol), (2-methylphenyl)hydrazine hydrochloride (47.7 g, 0.29 mol), and glacial acetic acid (7.03 g, 6.7 mL, 0.12 mol) were dissolved in abs ethanol (585 mL) and heated under reflux for 18 h. After removal of the solvent under reduced pressure, EtOAc and water (500 mL each) were added, then sodium bicarbonate (42 g, 0.50 mol) was carefully added. After addition of hexane (500 mL), the organic phase was separated, washed with brine (500 mL), and dried over $Na_2SO_4$. The mixture was then filtered through a pad of silica gel (500 g) on a sintered glass funnel. The pad was eluted with hexanes/EtOAc (1:1, v/v), and the filtrate was concentrated under reduced pressure. The resulting solid was triturated with hexanes/EtOAc (9:1, v/v), filtered, washed and dried in vacuo to afford a colorless solid (61.5 g, 93%). $^1$H NMR (400 MHz, $CD_2Cl_2$) δ 1.29 (s, 9H), 2.12 (s, 3H), 3.56 (br, 2H), 5.48 (s, 1H), 7.28 (m, 2H), 7.31 (m, 2H).

Intermediate D

Preparation of 3-(4-fluorophenyl)-1-(2-methylphenyl)-1H-pyrazol-5-amine

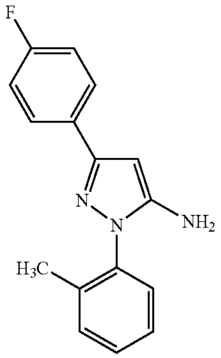

Step 1: Preparation of 3-amino-3-(4-fluorophenyl)acrylonitrile.

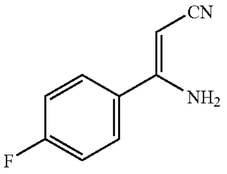

To a solution of 4-fluorobenzonitrile (5.00 g, 41.3 mmol) and acetonitrile (4.35 mL, 82.5 mmol) in toluene (100 mL) was added potassium tert-butoxide (13.9 g, 124 mmol). The mixture was stirred for 24 h, and then quenched by slow addition of aqueous sodium bicarbonate. The resulting suspension was extracted with dichloromethane (3×50 mL). The organic solution was washed with water, dried ($Na_2SO_4$), and concentrated under reduced pressure. The residue was triturated with EtOH/$Et_2O$ to afford 3-amino-3-(4-fluorophenyl)acrylonitrile (6.20 g, 93%) as a white solid. $^1$H NMR (300 MHz, acetone-$d_6$) δ 4.23 (s, 1H), 6.20 (s, 2H), 7.22 (ddd, 2H), 7.71 (m, 2H).

Step 2: Preparation of 3-(4-fluorophenyl)-1-(2-methylphenyl)-1H-pyrazol-5-amine

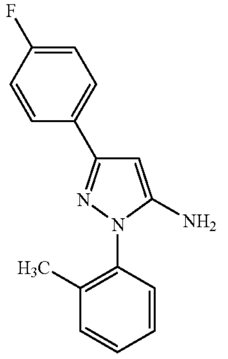

To a solution of 3-amino-3-(4-fluorophenyl)acrylonitrile (600 mg, 3.70 mmol) in 1 N HCl (6 mL) was added (2-methylphenyl)hydrazine hydrochloride (558 mg, 3.51 mmol). The reaction was refluxed for 16 h, and then cooled to rt. The resulting mixture was basified to pH 12 by slow addition of 1 N aqueous sodium hydroxide. The precipitate was collected by filtration, and then recrystallized from EtOH/$Et_2O$ to afford the intermediate (800 mg, 81%) as a light orange solid. $^1H$ NMR (400 MHz, $CD_2Cl_2$) δ 2.20 (s, 3H), 2.14 (br s, 2H), 5.91 (s, 1H), 7.06 (t, 2H), 7.36 (d, 4H), 7.75 (m, 2H). This material was used without further purification.

Intermediate E

Preparation of 3-(4-fluoro-2-methylphenyl)-1-(2-methylphenyl)-1H-pyrazol-5-amine

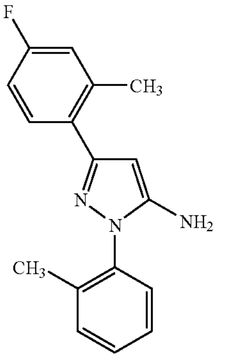

Step 1: Preparation of 4-fluoro-2-methylbenzoic acid

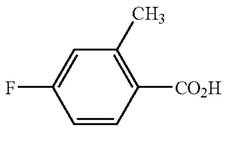

To a cooled (−78° C.) solution of 2-bromo-5-fluorotoluene (10.0 g, 52.9 mmol) in diethyl ether (100 mL) was added dropwise n-butyllithium (1.6 M in hexane, 21.2 mL, 52.9 mmol). The mixture was stirred for 5 min, and slowly warmed to 0° C. Dry ice (100 g, 2.27 mol) was slowly added to the mixture while stirring, and it was allowed to warm to rt over 16 h. The mixture was adjusted to pH=2, and extracted with ethyl acetate (3×20 mL). The organic phase was concentrated and the resulting yellow residue suspended in water (100 mL). The suspension was adjusted to pH=12 with 2 N NaOH, and washed with diethyl ether. The aqueous phase was then acidified to pH=2 with 2 N HCl, and extracted with diethyl ether (3×50 mL). The organic extract was washed with water, dried ($MgSO_4$), and concentrated under reduced pressure to afford the product (5.0 mg, 61%) as a white solid. $^1H$ NMR (400 MHz, DMSO-$d_6$) δ 2.53 (s, 3H), 7.06-7.17 (m, 2H), 7.87 (dd, 1H), 12.85 (s, 1H).

Step 2: Preparation of methyl 4-fluoro-2-methylbenzoate

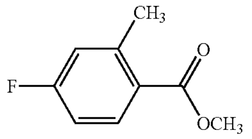

To a solution of 4-fluoro-2-methylbenzoic acid (4.0 g, 26.0 mmol) in THF (30 mL) in a pressure vessel was added cesium carbonate (8.45 mg, 26.0 mmol) and iodomethane (2.0 M in tert-butyl methyl ether, 13.0 mL, 26.0 mmol). The vessel was sealed and the reaction was stirred at 70° C. for 16 h. After cooling to rt, the reaction was quenched with saturated sodium bicarbonate (10 mL) and water (50 mL). The aqueous layer was extracted with dichloromethane (3×50 mL), and then the organic phase was dried ($Na_2SO_4$) and concentrated under reduced pressure to give the crude product. This material was triturated with acetone and hexanes to afford pure product (3.8 g, 87%) as a white solid. $^1H$ NMR (400 MHz, acetone-$d_6$) δ 2.60 (s, 3H), 3.86 (s, 3H), 7.05-7.12 (m, 2H), 7.96 (s, 1H); ES-MS m/z 168.2 ($MH^+$); HPLC RT (min) 3.20.

Step 3: Preparation of 3-(4-fluoro-2-methylphenyl)-3-oxopropanenitrile

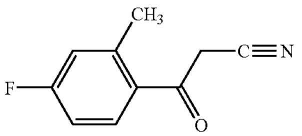

To a suspension of hexane-washed sodium hydride (60% oil dispersion, 995 mg, 24.9 mmol) was added dropwise a THF solution (20 mL) of methyl 4-fluoro-2-methylbenzoate (3.8 g, 22.6 mmol) and anhydrous acetonitrile (2.4 mL, 45.2 mmol). The mixture was stirred at 70° C. for 16 h, and then cooled to rt. The resulting mixture was diluted with ethyl acetate (20 mL) and 1 N HCl (10 mL) and the layers were partitioned. The organic phase was washed with water (3×20 mL) and brine (20 mL), dried ($Na_2SO_4$), and concentrated under reduced pressure to afford 4.0 g of yellow oil, which was taken to the next step without further purification. ES-MS m/z 178.2 ($MH^+$); HPLC RT (min) 2.22.

Step 4: Preparation of 3-(4-fluoro-2-methylphenyl)-1-(2-methylphenyl)-1H-pyrazol-5-amine

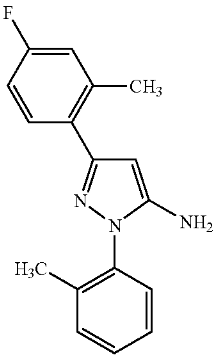

To a solution of 3-(4-fluoro-2-methylphenyl)-3-oxopropanenitrile (2.0 g, 11.3 mmol) in toluene (10 mL) was added (2-methylphenyl)hydrazine hydrochloride (2.15 g, 13.5 mmol). The reaction was stirred at 110° C. for 16 h, and then cooled to rt. It was concentrated under reduced pressure, and the residue was purified by silica gel flash chromatography (2:1-1:1=hexanes:ethyl acetate) to afford the product as a yellow oil (500 mg, 16%). $^1$H NMR (400 MHz, DMSO-$d_6$) δ 2.12 (s, 3H), 2.44 (s, 3H), 5.74 (s, 1H), 7.02-7.14 (m, 2H), 7.34-7.43 (m, 4H), 7.52 (dd, 1H); ES-MS m/z 282.4 (MH$^+$); HPLC RT (min) 3.36

Intermediate F

Preparation of 3-methyl-1-(2-methylphenyl)-1H-pyrazol-5-amine

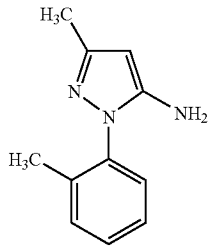

3-Aminocrotonitrile (2.00 g, 24.4 mmol) was added to a stirred solution of (2-methylphenyl)hydrazine hydrochloride (3.67 g, 23.1 mmol) in 1 M hydrochloric acid (20 mL). The reaction was heated (100° C.) for 18 h and then cooled to rt. The solution was adjusted to pH>12 using 1 M aqueous sodium hydroxide. The mixture was extracted with dichloromethane (3×20 mL), and then the combined organic extracts were washed with brine, dried over anhydrous magnesium sulfate, filtered, and concentrated in vacuo. Flash chromatography of the residue over silica gel using 25-50% ethyl acetate/hexane afforded 3-methyl-1-(2-methylphenyl)-1H-pyrazol-5-amine (3.97 g, 87%) as an orange oil. $^1$H NMR (300 MHz, acetone-$d_6$) δ 7.29 (m, 4H), 5.32 (s, 1H), 2.12 (s, 3H), 2.08 (s, 3H); ES-MS m/z 188.2 (MH$^+$), HPLC RT (min) 0.79.

Intermediate G

Preparation of 2-(2-methylphenyl)-4,5,6,7-tetrahydro-2H-indazol-3-amine

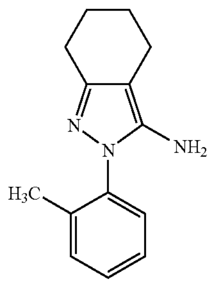

To a solution of (2-methylphenyl)hydrazine hydrochloride (464 mg, 2.92 mmol) in ethanol (2 mL) was added 2-oxocyclohexanecarbonitrile (300 mg, 2.44 mmol), and the mixture was heated to 60° C. and stirred for 16 h. The flask was then cooled to rt and the solvent was evaporated to give a solid. The crude residue of 2-(2-methylphenyl)-4,5,6,7-tetrahydro-2H-indazol-3-amine hydrochloride (449 mg, 70%) was used in the next step with no further purification. ES-MS m/z 228.2 (MH$^+$); HPLC RT (min) 1.22.

Intermediate H

Preparation of 4-(4-fluorophenyl)-3-methyl-1-(2-methylphenyl)-1H-pyrazol-5-amine

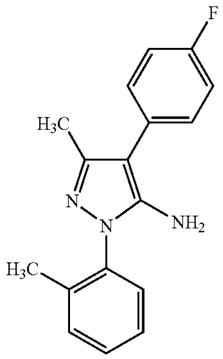

Step 1: Preparation of 4-bromo-3-methyl-1-(2-methylphenyl)-1H-pyrazol-5-amine

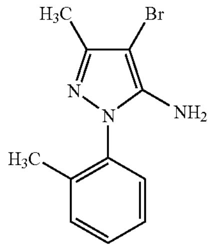

To a solution of 3-methyl-1-(2-methylphenyl)-1H-pyrazol-5-amine (Intermediate F, 7.78 g, 41.7 mmol) in acetic acid (90 mL) was added a solution of bromine (6.64 g, 41.6 mmol) in acetic acid (10 mL). The reaction mixture was stirred for 30 min. Water was added to the reaction mixture, and the mixture was basified using a cold KOH solution (1 N). The white solid, 4-bromo-3-methyl-1-(2-methylphenyl)-1H-pyrazol-5-amine, was collected and used in the next step without purification.

Step 2: Preparation of 4-(4-fluorophenyl)-3-methyl-1-(2-methylphenyl)-1H-pyrazol-5-amine

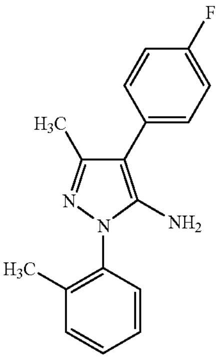

4-Bromo-3-methyl-1-(2-methylphenyl)-1H-pyrazol-5-amine (2 g, 7.52 mmol), 4-fluorophenylboronic acid (2.10 g, 11.3 mmol), and $Pd(PPh_3)_4$ (434 mg, 0.38 mmol) were dissolved in DMF (20 mL), and $Na_2CO_3$ (saturated aq solution, 18 mL) was added. The mixture was degassed for 10 min and then heated at 110° C. for 2 h. The reaction mixture was diluted, and the solid was filtered off. The solvent was concentrated under reduced pressure, and the residue purified by silica gel flash chromatography using 10 to 40% ethyl acetate in hexanes to give 1.2 g (90% pure, 51%) of the title compound. $^1$H NMR (300 MHz, $CD_2Cl_2$) δ 7.25-7.34 (m, 6H), 7.08 (t, 2H), 3.62 (s, 2H), 2.20 (s, 3H), 2.14 (s, 3H).

Intermediate I

Preparation of tert-butyl (4-bromo-3-tert-butyl-1-methyl-1H-pyrazol-5-yl)carbamate

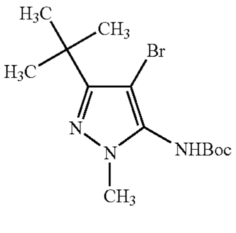

Step 1: Preparation of 4-bromo-3-tert-butyl-1-methyl-1H-pyrazol-5-amine

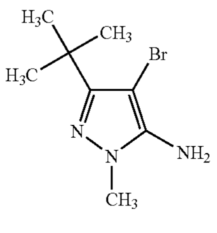

To a solution of 3-tert-butyl-1-methyl-1H-pyrazol-5-amine (10 g, 65.3 mmol) in acetic acid (90 mL) was added bromine (10.4 g, 65.26 mmol) in acetic acid (10 mL). The solution was stirred at rt for 30 min, and then water (100 mL) was added. The reaction mixture was basified to pH 9 using KOH (1.0 M ice cold solution). The resulting brown solid was filtered, collected, and purified by silica gel flash chromatography using 10 to 30% ethyl acetate in hexanes to afford 13.2 g (87%) of the title compound (white solid).

Step 2: Preparation of tert-butyl (4-bromo-3-tert-butyl-1-methyl-1H-pyrazol-5-yl)carbamate

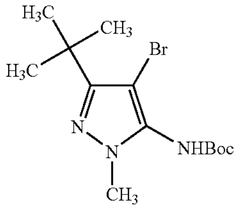

The product from Step 1 (2 g, 8.62 mmol), di-tert-butyl dicarbonate (2.82 g, 12.92 mmol), and DMAP (105 mg, 0.86 mmol) were dissolved in DCM (40 mL) and stirred for 16 h. Potassium carbonate (10% aqueous solution, 100 mL) was added into the reaction mixture, and stirring was continued for another 4 h. The organic layer was separated and concentrated under reduced pressure. The residue was purified by silica gel flash chromatography with 5 to 20% ethyl acetate in hexanes to give 2.3 g (80%) of the title compound. $^1$H NMR (300 MHz, $CD_2Cl_2$) δ 3.55 (s, 3H), 1.37 (s, 9H), 1.31 (s, 9H).

Intermediate J

Preparation of 4-bromo-3-tert-butyl-1-(2-methylphenyl)-1H-pyrazol-5-amine

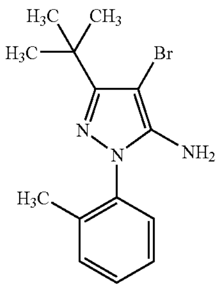

To a solution of 3-tert-butyl-1-(2-methylphenyl)-1H-pyrazol-5-amine (1.00 g, 4.36 mmol) in acetic acid (10 mL) was added bromine (662 mg, 0.21 mL, 4.14 mmol) dropwise. The reaction mixture was stirred for 5 min, and then diluted with water (50 mL), causing a solid to precipitate. The solid was collected by filtration, then dissolved in EtOAc (50 mL). The EtOAc solution was then washed with saturated $NaHCO_3$ and brine, dried ($Na_2SO_4$), and concentrated under reduced pressure to afford the product (935 mg, 70%) as a white solid: $^1$H NMR (300 MHz, DMSO-$d_6$) δ 1.32 (s, 9H), 2.04 (s, 3H) 5.02 (s, 2H), 7.20-7.38 (m, 4H). ES-MS m/z 308.6 ($MH^+$); HPLC RT (min) 3.15.

Intermediate K

Preparation of 3-tert-butyl-4-methyl-1-(2-methylphenyl)-1H-pyrazol-5-amine

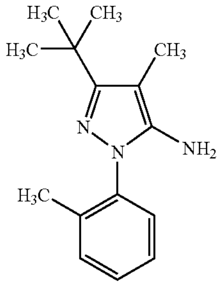

To a solution of 4-bromo-3-tert-butyl-1-(2-methylphenyl)-1H-pyrazol-5-amine (Intermediate J, 800 mg, 2.60 mmol) in DMF (5 mL) was added trimethylboroxine (0.73 mL, 5.19 mmol), [1,1'-bis(diphenylphosphino)-butane]palladium (II) dichloride (157 mg, 0.26 mmol), and potassium carbonate (1.08 g, 7.79 mmol). The reaction mixture was stirred for 18 h at 155° C. After cooling, the reaction mixture was diluted with water (100 mL) and extracted with EtOAc (3×25 mL). The combined organic layers were washed with brine, dried ($Na_2SO_4$), filtered, and concentrated under reduced pressure. The residue was purified by silica gel flash chromatography using hexane/EtOAc (1:9, v/v) to afford the product (243 mg, 38%) as a white solid: $^1$H NMR (300 MHz, DMSO-$d_6$) δ 1.24 (s, 9H), 1.97 (s, 3H), 2.03 (s, 3H), 4.48 (s, 2H) 7.14-7.32 (m, 4H). ES-MS m/z 244.2 (MH$^+$); HPLC RT (min) 1.17.

Intermediate L

Preparation of 3-tert-butyl-1-methyl-4-pyridin-3-yl-1H-pyrazol-5-amine

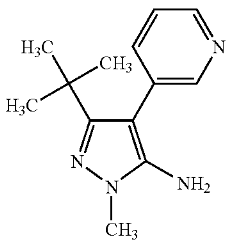

tert-Butyl (4-bromo-3-tert-butyl-1-methyl-1H-pyrazol-5-yl)carbamate (Intermediate I, 1.7 g, 5.12 mmol), pyridine-3-boronic acid (1.26 g, 10.23 mmol), and $Pd(PPh_3)_4$ (295 mg, 0.26 mmol) were dissolved in ethanol (25 mL), and $Na_2CO_3$ (2 M aqueous solution, 25 mL) was added. The mixture was degassed for 10 min. The reaction mixture was then heated to 80° C. for 16 h. The mixture was diluted with ethyl acetate, the solid was filtered off, and the filtrate was treated with TFA (5 mL). The mixture was stirred for 30 min before being concentrated under reduced pressure. The crude was dissolved in methanol and filtered though a $C_8$-silica plug. HPLC purification with gradient elution from 5 to 60% acetonitrile in water afforded 300 mg (25%) of the title compound. $^1$H NMR (300 MHz, $CD_3OD$) δ 8.73 (d, 1H), 8.64 (s, 1H), 8.14 (d, 1H), 7.81 (dd, 1H), 3.73 (s, 3H), 1.20 (s, 9H). ES-MS m/z 231.2 (MH$^+$); HPLC RT (min) 0.23.

Intermediate M

Preparation of 4-ethyl-3-(4-fluorophenyl)-1-(2-methylphenyl)-1H-pyrazol-5-amine

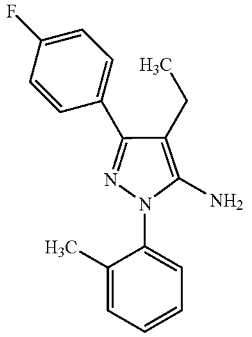

Step 1: Preparation of 3-(4-fluorophenyl)-1-(2-methylphenyl)-4-vinyl-1H-pyrazol-5-amine

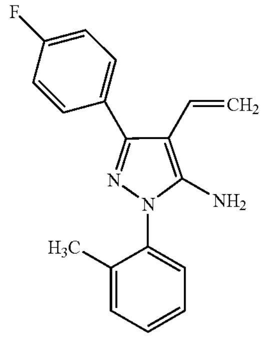

To a solution of 4-bromo-3-(4-fluorophenyl)-1-(2-methylphenyl)-1H-pyrazol-5-amine (200 mg, 0.58 mmol) in toluene (10 mL) was added tributylvinyl tin (0.33 mL, 366 mg, 1.16 mmol) and tetrakis(triphenylphosphine)palladium(0) (66 mg, 0.06 mmol). The reaction mixture was heated to reflux and stirred for 16 h. After cooling to rt, the mixture was concentrated under reduced pressure. The residue was dissolved in EtOAc (100 mL), washed with brine (50 mL), dried ($Na_2SO_4$), filtered, and concentrated under reduced pressure. Silica gel flash chromatography of the residue using 10% EtOAc/Hex afforded 3-(4-fluorophenyl)-1-(2-methylphenyl)-4-vinyl-1H-pyrazol-5-amine (87 mg, 51%): $^1$H NMR (300 MHz, DMSO-$d_6$) δ 2.12 (s, 3H), 4.96 (dd, 1H) 5.21 (dd, 1H), 5.26 (s, 2H), 6.55 (dd, 1H), 7.18-7.56 (m, 8H). ES-MS m/z294.2 (MH$^+$); HPLC RT (min) 3.54.

Step 2: Preparation of 4-ethyl-3-(4-fluorophenyl)-1-(2-methylphenyl)-1H-pyrazol-5-amine

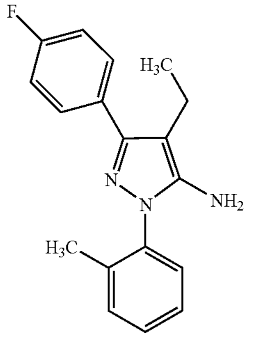

To a mixture of wet palladium on carbon (10 wt %, 10 mg) in EtOH (5 mL) was added 3-(4-fluorophenyl)-1-(2-methylphenyl)-4-vinyl-1H-pyrazol-5-amine (87 mg, 0.30 mmol) in EtOH (5 mL). The reaction was mixed on a Parr shaker under $H_2$ atmosphere (55 psi) for 16 h. The palladium catalyst was filtered through Celite® and rinsed with EtOH (3×20 mL). The solution was concentrated under reduced pressure to afford the title compound (68 mg, 77%) containing trace impurities. This material was used in subsequent reactions without further purification: ES-MS m/z 296.2 ($MH^+$); HPLC RT (min) 2.65.

2-Bromobenzoic Acid Derivatives

Intermediate N

Preparation of methyl 2-bromo-5-(difluoromethoxy)benzoate

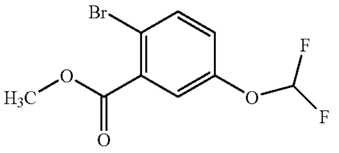

Step 1: Preparation of methyl 2-bromo-5-hydroxybenzoate

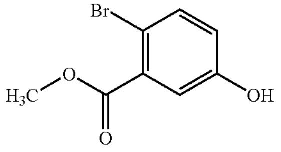

To a cold solution (ice water bath) of the methyl-2-bromo-5-methoxybenzoate (2.00 g, 8.16 mmol) in dichloromethane (15 mL) was added $AlCl_3$(5.44 g, 40.8 mmol) under argon, and the reaction temperature was maintained below 10° C. using an ice-water bath. The light brown suspension was stirred for 10 min, then EtSH (3.02 mL, 40.8 mmol) was added dropwise at such a rate that the reaction temperature was maintained below 5° C. After 2.5 h of stirring below 10° C., the reaction mixture was slowly poured into ice water with agitation. The organic layer was separated, and the aqueous layer was extracted with DCM. The combined organic layers were washed with water, dried over $MgSO_4$, filtered and concentrated under reduced pressure to afford a light yellow oil which was used in the next step without further purification.

Step 2: Preparation of methyl 2-bromo-5-(difluoromethoxy)benzoate

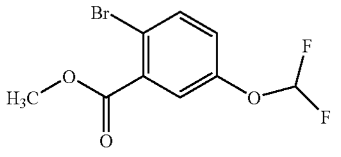

To a solution of methyl 2-bromo-5-hydroxybenzoate (5.63 mmol, 1.30 g) in DMF (8 mL) was added cesium carbonate (11.3 mmol, 3.67 g) and methyl chlorodifluoroacetate (6.75 mmol, 0.71 mL), and the reaction mixture stirred at 90° C. for 16 h. After cooling to rt and dilution with ethyl acetate, the mixture was filtered and concentrated under reduced pressure. The residue was purified by silica gel chromatography using hexane/EtOAc (9:1, v/v) as the eluent. The product was obtained as a light yellow oil (560 mg, 35%). GC-MS m/z: 280 ($MH^+$).

Secondary and Tertiary Amides

The amine precursors used for all amide forming reactions were commercially available except the amine used for Example 315. Its synthesis is described in the following section.

Intermediate O

Preparation of (2-{4-methoxy-3-[(4-methylpiperazin-1-yl)sulfonyl]phenyl}ethyl)amine dihydrochloride

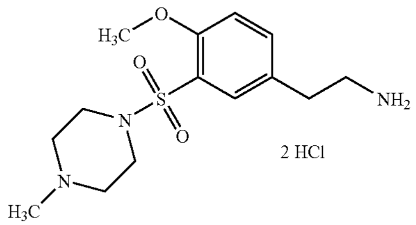

Step 1: Preparation of 2,2,2-trifluoro-N-[2-(4-methoxyphenyl)ethyl]acetamide

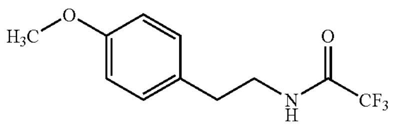

To a solution of 4-methoxyphenethylamine (2.5 g, 16.5 mmol) in $CH_2Cl_2$ (45 mL) at 0° C. was added a solution of trifluoroacetic anhydride in $CH_2Cl_2$ (5 mL). The reaction mixture was stirred at 0° C. for 30 min and then at rt for 1 h. Then a saturated aqueous solution of $NH_4Cl$ was added, the phases separated and the aqueous phase extracted with $CH_2Cl_2$. The combined organic phases were dried ($Na_2SO_4$), filtered and concentrated under reduced pressure. The resulting solid was recrystallized from $Et_2O$/hexanes to give the product as a beige solid (2.36 g, 58%). $^1H$ NMR (400 MHz, $CDCl_3$), δ 2.82 (t, 2H), 3.62 (q, 2H), 3.81 (s, 3H), 6.19-6.30 (broad, 1H), 6.87 (d, 2H), 7.10 (d, 2H); GC-MS m/z 247 ($M^+$),1 RT (min) 12.22.

Step 2: Preparation of 2,2,2-trifluoro-N-(2-{4-methoxy-3-[(4-methylpiperazin-1-yl) sulfonyl] phenyl}ethyl) acetamide

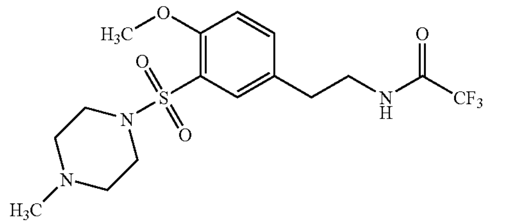

To a flask charged with 2,2,2-trifluoro-N-[2-(4-methoxyphenyl)ethyl]acetamide (1.00 g, 4.05 mmol) was added chlorosulfonic acid (4 mL) at 0° C. under $N_2$. After 30 min, the reaction temperature was raised to rt, and stirring was continued for an additional 90 min. The reaction mixture was the added dropwise to a mixture of $CH_2Cl_2$ and ice-water being cooled by an ice bath [violent reaction upon contact with water]. The phases were separated, and the aqueous layer was extracted with $CH_2Cl_2$. The combined organic phases were dried ($Na_2SO_4$), filtered and concentrated under reduced pressure.

The resulting sulfonyl chloride was dissolved in $CH_2Cl_2$ (30 mL) to which were added $Et_3N$ (1.29 mL, 8.10 mmol) and 1-methylpiperazine (0.674 mL, 6.08 mmol) at 0° C. under $N_2$. The solution was warmed to rt and stirred for 14 h. Then the reaction mixture was concentrated and purified by silica gel flash chromatography using EtOAc/MeOH (4:1, v/v) to give the title compound as a yellow oil (1.26 g, 75%). $^1H$ NMR (400 MHz, $CDCl_3$). δ 2.13 (s, 3H), 2.48 (broad t, 4H), 2.87 (t, 2H), 3.27 (broad t, 4H), 3.56 (q, 2H), 3.88 (s, 3H), 6.70-6.77 (broad s, 1H), 6.94 (d, 1H), 7.33 (dd, 1H), 7.69 (dd, 1H); ES-MS m/z 410.3 ($(MH)^+$), 432.1 ($(M+Na)^+$) 840.7 ($(2M+Na)^+$) HPLC RT (min) 1.19.

Step 3: Preparation of (2-{4-methoxy-3-[(4-methylpiperazin-1-yl)sulfonyl]phenyl} ethyl)amine dihydrochloride

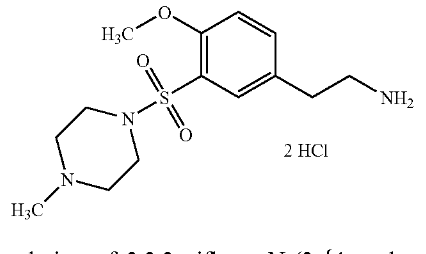

2 HCl

To a solution of 2,2,2-trifluoro-N-(2-{4-methoxy-3-[(4-methylpiperazin-1-yl)sulfonyl]-phenyl}ethyl) acetamide (from Step 2), (1.25 g, 3.05 mmol) in MeOH (30 mL) and $H_2O$ (8 mL) was added $K_2CO_3$ (2.11 g, 15.3 mmol), and the solution was stirred at 60° C. for 2 h. After cooling to rt, the MeOH was evaporated under reduced pressure. The remaining aqueous mixture was extracted with $CH_2Cl_2$ (6×50 mL), and the combined organic phases were dried ($Na_2SO_4$), filtered, and concentrated under reduced pressure. The residue was then dissolved in MeOH, and 4 equivalents of 1 N HCl in MeOH were added causing the formation of a white precipitate. The solvent was removed under reduced pressure, and the resulting solid was recrystallized from MeOH/$Et_2O$ to give the title compound [assumed to be the bis-HCl salt] as a white solid (457 mg, 48%). $^1H$ NMR (400 MHz, $CD_3OD$) δ 2.29 (s, 3H), 2.48 (broad t, 4H), 2.78 (dd, 2H), 2.87-2.92 (m, 2H), 3.23 (broad t, 4H), 3.91 (s, 3H) 7.16 (d, 1H), 7.47 (dd, 1H), 7.68 (d, 1H); ES-MS m/z ($MH^+$) 314.2, HPLC RT (min) 0.70.

EXAMPLE 1

Preparation of 2-[(3-tert-butyl-1-methyl-1H-pyrazol-5-yl)amino]-5-methoxybenzoic acid

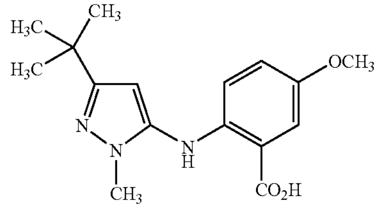

A mixture of 2-bromo-5-methoxy benzoic acid (2.26 g, 9.79 mmol), potassium carbonate (1.49 g, 10.8 mmol), 5-amino-3-tert-butyl-1-methylpyrazole (1.50 g, 9.79 mmol), and copper (II) acetate (35 mg, 0.20 mmol) in DMF (20 mL) was heated (150° C.) in a sealed tube for 16 h. After cooling, the reaction mixture was diluted with water (10 mL) and acidified to pH=4 with acetic acid. This mixture was extracted with dichloromethane (3×20 mL), and then the combined organic extracts were washed with water (2×30 mL), dried over $Na_2SO_4$, filtered, and concentrated under reduced pressure. HPLC purification of the residue (YMC propack C18 column, 150×20 mm ID, 30%-80% acetonitrile in water gradient) afforded the title compound (973 mg, 31%) as a pale yellow solid. $^1H$ NMR (300 MHz, DMSO-$d_6$) δ 13.22 (br s, 1H), 9.24 (br s, 1H), 7.38 (d, 1H), 7.10 (dd, 1H), 6.80 (d, 1H), 5.95 (s, 1H), 3.70 (s, 3H), 3.55 (s, 3H), 1.21 (s, 9H); ES-MS m/z 304.2 ($MH^+$), HPLC RT (min) 2.58.

EXAMPLE 2

Preparation of 2-{[3-(4-chlorophenyl)-1-methyl-1H-pyrazol-5-yl)amino]}-4,5-dimethoxybenzoic acid trifluoroacetate

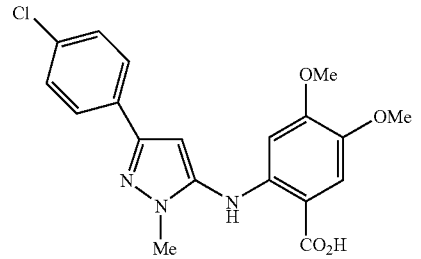

TFA

A mixture of 2-bromo-4,5-dimethoxy benzoic acid (105 mg, 0.40 mmol), potassium carbonate (61 mg, 0.44 mmol), 5-amino-3-(4-chlorophenyl)-1-methylpyrazole (84 mg, 0.40 mmol), and copper (II) acetate (2 mg, 0.01 mmol) in DMF (2 mL) was heated (150° C.) in a sealed tube for 16 h. After cooling, the reaction mixture was diluted with water (2 mL) and then acidified to pH=4 with acetic acid. The mixture was extracted with dichloromethane (3×5 mL), and then the combined organic extracts were washed with water (2×5 mL), dried over $Na_2SO_4$, filtered, and concentrated under reduced pressure. HPLC-MS purification of the residue (HPLC: YMC propack C18 column, 100×20 mm ID, 10%-95% acetonitrile/TFA (0.1%) in water/TFA (0.1%) gradient; MS: 120-1000 amu on Micromass LCZ single quadrupole with electrospray ionization) afforded the title compound (28 mg, 14%) as a white solid. $^1H$ NMR (300 MHz, DMSO-$d_6$) δ 9.78 (s, 1H), 7.82 (ddd, 2H), 7.42 (ddd, 2H), 7.36 (s, 1H), 6.74 (s, 1H), 6.56 (s, 1H), 3.74 (s, 3H), 3.71 (s, 6H); ES-MS m/z 388.2 ($MH^+$), HPLC RT (min) 2.58.

EXAMPLE 3

Preparation of 2-{[3-(4-fluorophenyl)-1-(2-methylphenyl)-1H-pyrazol-5-yl]amino}benzoic acid

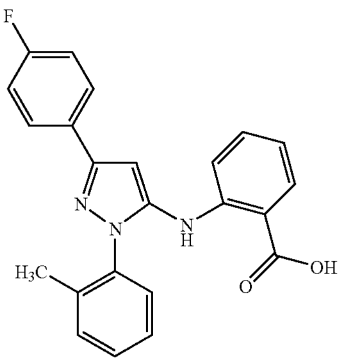

To a solution of 3-(4-fluorophenyl)-1-(2-methylphenyl)-1H-pyrazol-5-amine (Intermediate D, 100 mg, 0.37 mmol) in DMF (3 mL), was added 2-iodobenzoic acid (93 mg, 0.37 mmol), potassium carbonate (62 mg, 0.45 mmol), and copper (II) acetate (3 mg, 0.01 mmol). The mixture was stirred at 150° C. for 18 h and then cooled to rt. The solution was adjusted to pH 4 using glacial acetic acid. The mixture was extracted with dichloromethane (3×5 mL), and then the combined organic extracts were washed with brine, dried ($MgSO_4$), filtered, and concentrated under reduced pressure. The residue was purified by HPLC (45-90% acetonitrile in water) to afford the title compound (17 mg, 12%) as a light yellow solid. $^1H$ NMR (400 MHz, DMSO-$d_6$) δ 2.08 (s, 3H), 6.85 (ddd, 1H), 6.93 (s, 1H), 7.24 (ddd, 2H), 7.42 (m, 6H), 7.84 (dd, 1H), 7.92 (ddd, 2H), 10.02 (s, 1H), 13.23 (s, 1H); ES-MS m/z 388.2 ($MH^+$); HPLC RT (min) 3.47.

EXAMPLE 4

Preparation of 2-{[3-tert-butyl-1-(2-methylphenyl)-1H-pyrazol-5-yl]amino}-5-methoxybenzoic acid

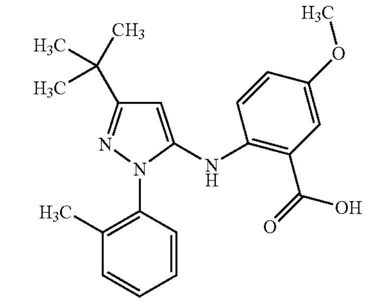

To a solution of 3-tert-butyl-1-(2-methylphenyl)-1H-pyrazol-5-amine (Intermediate C, 1.00 g, 4.36 mmol) in DMF (20 mL), was added 2-bromo-5-methoxybenzoic acid (1.01 g, 4.36 mmol), potassium carbonate (723 mg, 5.23 mmol), and copper (II) acetate (32 mg, 0.17 mmol). The mixture was stirred at 150° C. for 18 h and then cooled to rt. The solution was adjusted to pH 4 using glacial acetic acid. The mixture was extracted with dichloromethane (3×5 mL), and then the combined organic extracts were washed with brine, dried ($MgSO_4$), filtered, and concentrated under reduced pressure. The residue was purified by HPLC (45-90% acetonitrile in water) to afford the product (500 mg, 33%) as a light yellow solid. $^1H$ NMR (400 MHz, DMSO-$d_6$) δ 1.29 (s, 9H), 1.98 (s, 3H), 3.69 (s, 3H), 6.19 (s, 1H), 7.14 (dd, 1H), 7.26-7.37 (m, 6H), 9.49 (s, 1H), 13.25 (s, 1H); ES-MS m/z 380.3 ($MH^+$); HPLC RT (min) 3.18.

The following analogs were synthesized using the methods described in Examples 1-4. Examples 7 and 28 were obtained as trifluoroacetic acid salts, as described for Example 2.

In Table 1a, the locant of the $R^4$ group(s) is defined as shown.

TABLE 1a

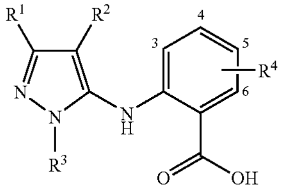

| Ex. No. | $R^1$ | $R^2$ | $R^3$ | $R^4$ | LC-MS RT (min) | LC-MS $[M + H]^+$ | Note* |
|---|---|---|---|---|---|---|---|
| 5 | H | H | Et | — | 2.38 | 232.1 | c |
| 6 | H | H | Ph | 5-SMe | 3.02 | 326.1 | c |
| 7 | Me | H | Me | 4-F | 2.31 | 250.1 | c |

TABLE 1a-continued
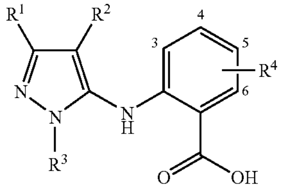
| Ex. No. | $R^1$ | $R^2$ | $R^3$ | $R^4$ | LC-MS RT (min) | LC-MS $[M + H]^+$ | Note* |
|---|---|---|---|---|---|---|---|
| 8 | Me | H | Me | 3-$CF_3$ | 1.94 | 300.1 | c |
| 9 | Me | H | Bn | 4-F | 2.85 | 326.2 | c |
| 10 | Me | H | Ph | 5-OMe | 2.79 | 324.1 | c |
| 11 | t-Bu | H | Me | — | 2.81 | 274.1 | c |
| 12 | t-Bu | H | Me | 5-SMe | 2.90 | 320.2 | c |
| 13 | t-Bu | H | Et | 4,5-di-OMe | 2.54 | 366.2 | I |
| 14 | t-Bu | H | 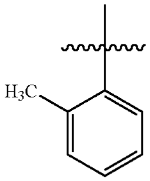 | — | 3.3 | 350.2 | I |
| 15 | t-Bu | H | 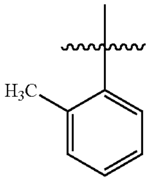 | 4,5-di-OMe | 3.06 | 410.2 | I |
| 16 | t-Bu | H | 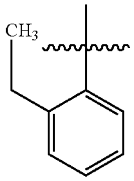 | 5-OMe | 3.31 | 394.3 | I |
| 17 | t-Bu | H | 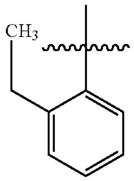 | 4,5-di-OMe | 3.77 | 424.2 | I |
| 18 | t-Bu | H | 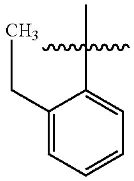 | — | 3.99 | 364.2 | I |
| 19 | t-Bu | H | 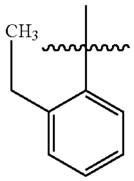 | 5-OMe | 3.90 | 394.2 | I |

TABLE 1a-continued
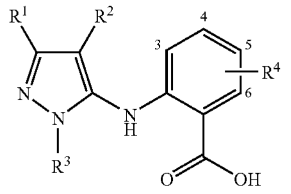
| Ex. No. | $R^1$ | $R^2$ | $R^3$ | $R^4$ | LC-MS RT (min) | LC-MS $[M + H]^+$ | Note* |
|---|---|---|---|---|---|---|---|
| 20 | t-Bu | H | 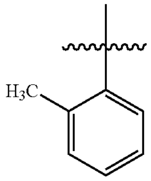 | 6-F | 3.84 | 368.2 | I |
| 21 | t-Bu | H | 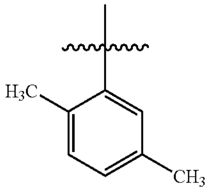 | 4-F | 4.14 | 382.2 | I |
| 22 | t-Bu | H | 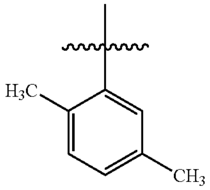 | 5-F | 4.02 | 382.2 | I |
| 23 | t-Bu | H | 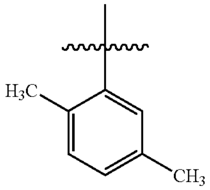 | 6-F | 3.97 | 382.2 | I |
| 24 | t-Bu | H | 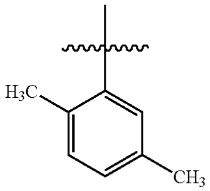 | 4-Me | 4.07 | 378.2 | I |
| 25 | t-Bu | H | 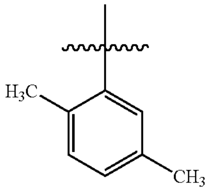 | 5-Me | 4.06 | 378.2 | I |

TABLE 1a-continued
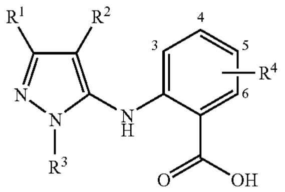
| Ex. No. | $R^1$ | $R^2$ | $R^3$ | $R^4$ | LC-MS RT (min) | LC-MS $[M + H]^+$ | Note* |
|---|---|---|---|---|---|---|---|
| 26 | t-Bu | H | 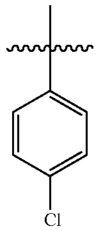 | 4,5-di-OMe | 3.60 | 430.2 | I |
| 27 | t-Bu | H | 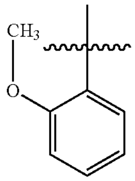 | 5-OMe | 3.65 | 396.2 | I |
| 28 | Ph | H | Me | 4,5-di-OMe | 2.71 | 354.2 | c |
| 29 | Ph | H | Ph | 5-OMe | 4.06 | 386.2 | c |
| 30 | Ph | H | 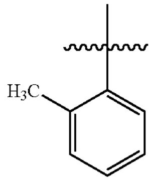 | — | 3.57 | 370.1 | J |
| 31 | Ph | H | 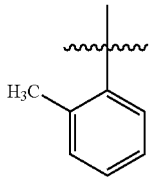 | 4,5-di-OMe | 3.36 | 430.1 | J |
| 32 | Ph | H | 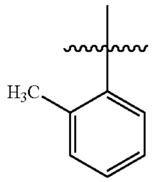 | 5-OMe | 3.39 | 400.2 | J |
| 33 | Ph | H | 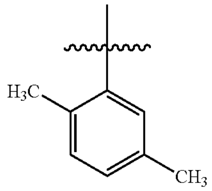 | 4-F | 3.75 | 402.1 | J |

TABLE 1a-continued
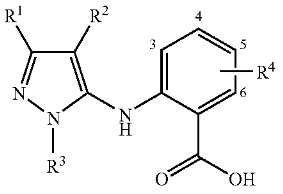
| Ex. No. | $R^1$ | $R^2$ | $R^3$ | $R^4$ | LC-MS RT (min) | LC-MS $[M + H]^+$ | Note* |
|---|---|---|---|---|---|---|---|
| 34 | Ph | H | 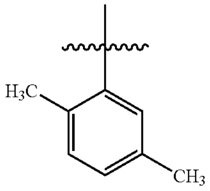 | 6-F | 3.60 | 402.2 | J |
| 35 | Ph | H | 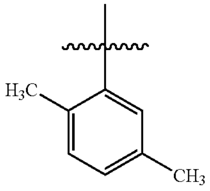 | 4-Me | 3.76 | 398.2 | J |
| 36 | Ph | H | 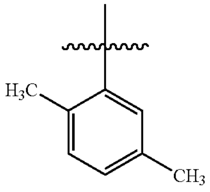 | 5-Me | 3.79 | 398.2 | J |
| 37 | Ph | H | 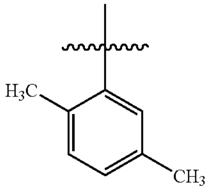 | — | 3.63 | 384.2 | J |
| 38 | Ph | H | 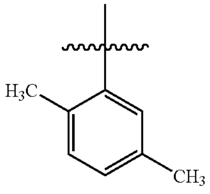 | 5-OMe | 3.57 | 414.1 | J |
| 39 | Ph | H | 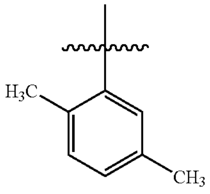 | 4,5-di-OMe | 3.39 | 444.2 | J |

TABLE 1a-continued
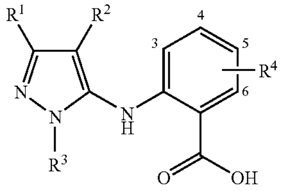
| Ex. No. | $R^1$ | $R^2$ | $R^3$ | $R^4$ | LC-MS RT (min) | LC-MS $[M + H]^+$ | Note* |
|---|---|---|---|---|---|---|---|
| 40 | Ph | H | 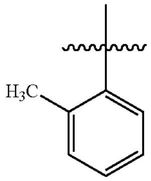 | 4-F | 3.56 | 388.1 | J |
| 41 | Ph | H | 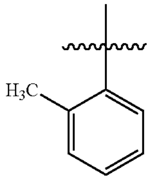 | 6-F | 3.43 | 388.2 | J |
| 42 | Ph | H | 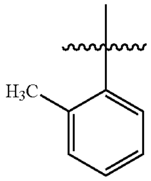 | 4-Cl | 4.20 | 404.1 | J |
| 43 | Ph | H | 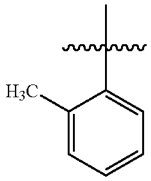 | 5-Me | 4.07 | 384.2 | J |
| 44 | Ph | H | 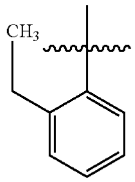 | 5-OMe | 3.56 | 414.3 | J |
| 45 | Ph | H | 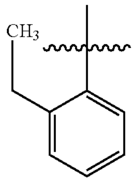 | 4,5-di-OMe | 3.36 | 444.3 | J |
| 46 | 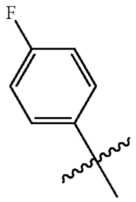 | H | Ph | 5-MeO | 3.52 | 404.2 | J |

TABLE 1a-continued
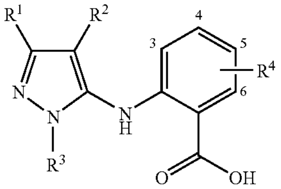
| Ex. No. | $R^1$ | $R^2$ | $R^3$ | $R^4$ | LC-MS RT (min) | LC-MS $[M + H]^+$ | Note* |
|---|---|---|---|---|---|---|---|
| 47 | 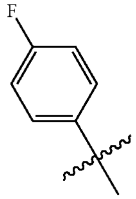 | H | 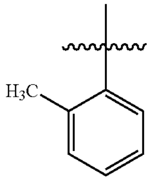 | 5-OMe | 3.44 | 418.2 | J |
| 48 | 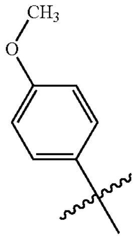 | H | 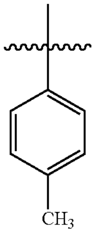 | — | 3.93 | 400.2 | J |
| 49 | 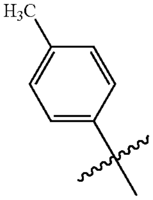 | H | 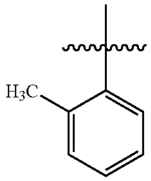 | — | 3.55 | 384.2 | J |
| 50 | 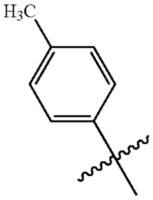 | H | 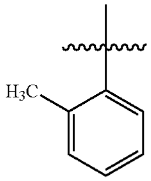 | 5-OMe | 3.52 | 414.3 | J |
| 51 | 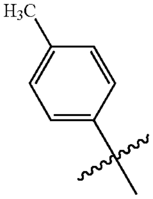 | H | 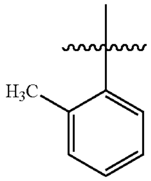 | 4,5-di-OMe | 3.33 | 444.2 | J |
| 52 | 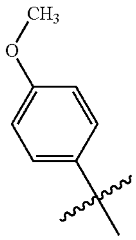 | H | 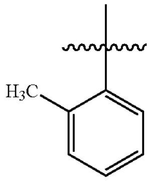 | — | 3.30 | 400.2 | J |

TABLE 1a-continued
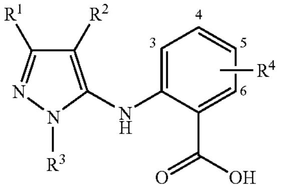
| Ex. No. | $R^1$ | $R^2$ | $R^3$ | $R^4$ | LC-MS RT (min) | LC-MS $[M + H]^+$ | Note* |
|---|---|---|---|---|---|---|---|
| 53 | 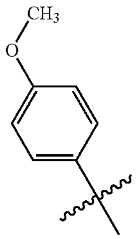 | H | 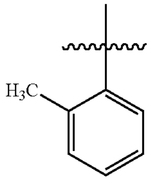 | 5-OMe | 3.27 | 430.2 | J |
| 54 | 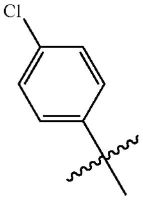 | H | 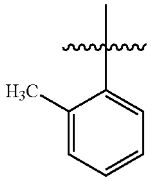 | 4,5-di-OMe | 3.47 | 464.2 | J |
| 55 | 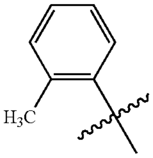 | H | 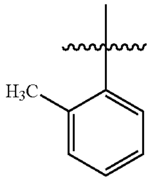 | 5-OMe | 3.66 | 414.2 | J |
| 56 | 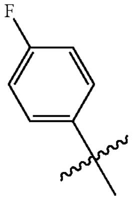 | H | 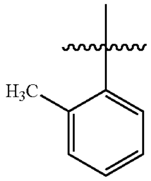 | 4-F | 3.63 | 406.2 | J |
| 57 | 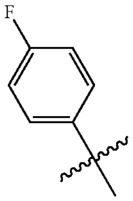 | H | 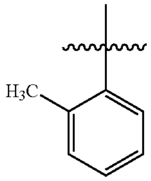 | 6-F | 3.95 | 406.1 | J |
| 58 | 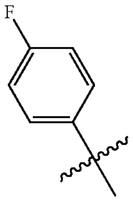 | H | 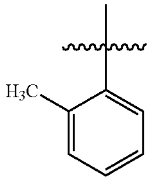 | 4-Me | 4.10 | 402.2 | J |

TABLE 1a-continued
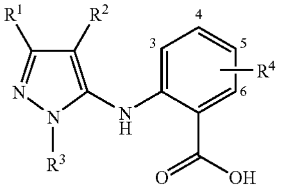
| Ex. No. | $R^1$ | $R^2$ | $R^3$ | $R^4$ | LC-MS RT (min) | LC-MS $[M + H]^+$ | Note* |
|---|---|---|---|---|---|---|---|
| 59 | 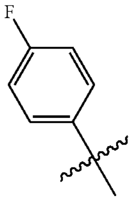 | H | 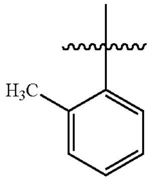 | 5-Me | 4.12 | 402.2 | J |
| 60 | 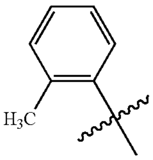 | H | 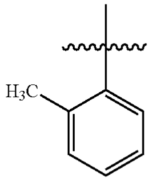 | — | 3.68 | 384.2 | J |
| 61 | 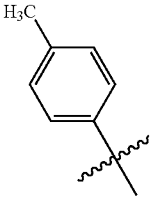 | H | 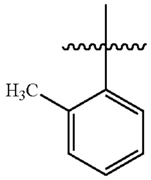 | 4-F | 3.73 | 402.1 | J |
| 62 | 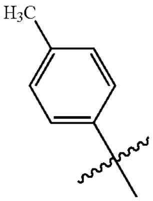 | H | 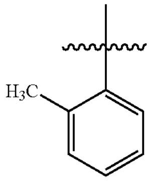 | 6-F | 3.59 | 402.1 | J |
| 63 | 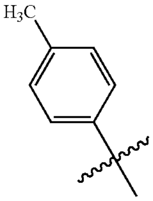 | H | 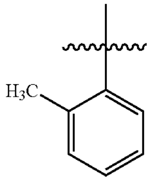 | 4-Cl | 3.93 | 418.1 | J |
| 64 | 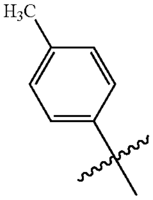 | H | 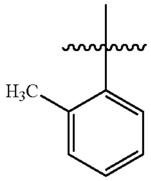 | 4-Me | 3.73 | 398.2 | J |

TABLE 1a-continued
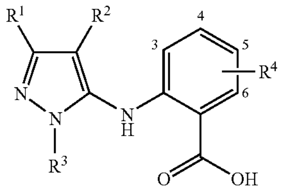
| Ex. No. | $R^1$ | $R^2$ | $R^3$ | $R^4$ | LC-MS RT (min) | LC-MS $[M + H]^+$ | Note* |
|---|---|---|---|---|---|---|---|
| 65 | 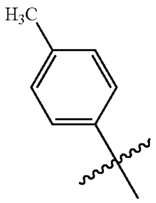 | H | 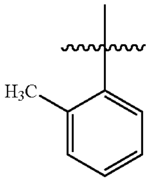 | 5-Me | 3.77 | 398.2 | J |
| 66 | 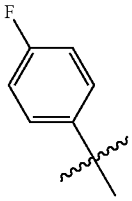 | H | 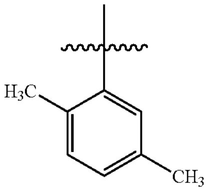 | — | 4.12 | 402.2 | J |
| 67 | 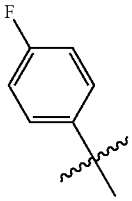 | H | 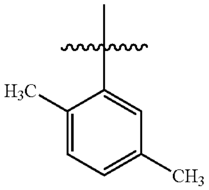 | 4-F | 4.21 | 420.2 | J |
| 68 | 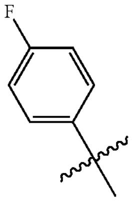 | H | 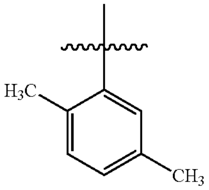 | 6-F | 4.08 | 420.1 | J |
| 69 | 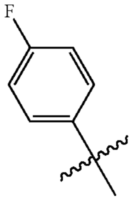 | H | 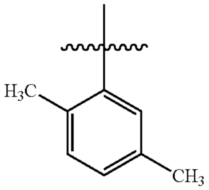 | 4-Me | 4.23 | 416.2 | J |
| 70 | 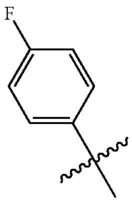 | H | 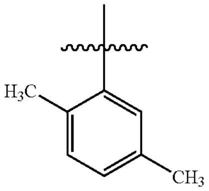 | 5-Me | 4.25 | 416.2 | J |

TABLE 1a-continued
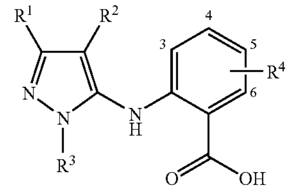
| Ex. No. | $R^1$ | $R^2$ | $R^3$ | $R^4$ | LC-MS RT (min) | LC-MS $[M + H]^+$ | Note* |
|---|---|---|---|---|---|---|---|
| 71 | 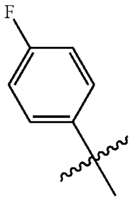 | H | 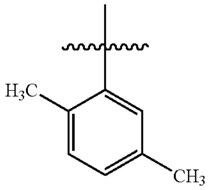 | 5-OMe | 4.09 | 432.2 | J |
| 72 | 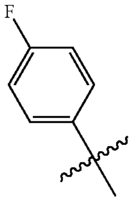 | H | 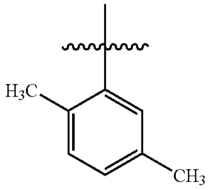 | 4,5-di-OMe | 3.93 | 462.2 | J |
| 73 | 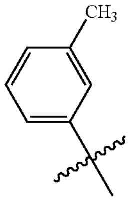 | H | 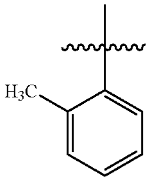 | — | 4.07 | 384.2 | J |
| 74 | 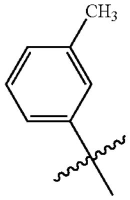 | H | 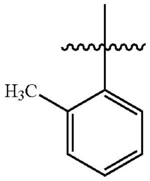 | 5-OMe | 4.05 | 414.2 | J |
| 75 | Me | 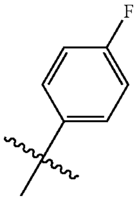 | 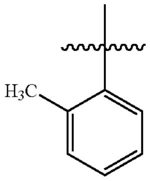 | 6-F | 3.26 | 420.2 | K |
| 76 | t-Bu | H | 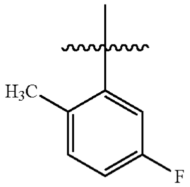 | 6-F | 3.94 | 386.2 | I |

TABLE 1a-continued
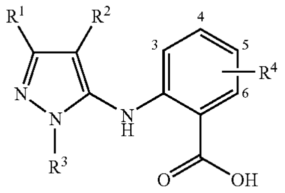
| Ex. No. | $R^1$ | $R^2$ | $R^3$ | $R^4$ | LC-MS RT (min) | LC-MS $[M + H]^+$ | Note* |
|---|---|---|---|---|---|---|---|
| 77 | t-Bu | H | 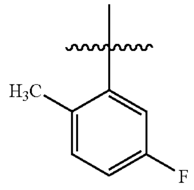 | 4-F | 4.1 | 386.2 | I |
| 78 | t-Bu | H | 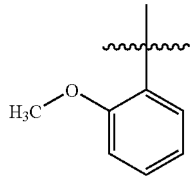 | 4-F | 3.58 | 384.2 | I |
| 79 | t-Bu | H | 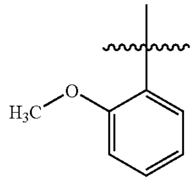 | 5-Me | 3.51 | 380.2 | I |
| 80 | t-Bu | H | 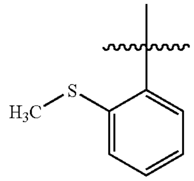 | 5-OMe | 3.36 | 412.2 | I |
| 81 | t-Bu | H | 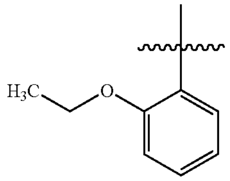 | — | 3.86 | 380.3 | I |
| 82 | t-Bu | H | 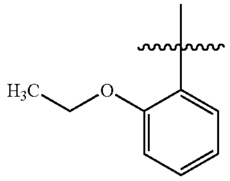 | 5-OMe | 3.73 | 410.3 | I |
| 83 | t-Bu | H | 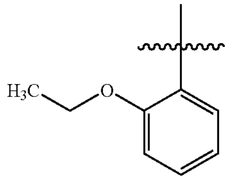 | 5-Me | 3.92 | 394.2 | I |

TABLE 1a-continued
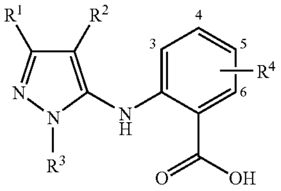
| Ex. No. | $R^1$ | $R^2$ | $R^3$ | $R^4$ | LC-MS RT (min) | LC-MS $[M + H]^+$ | Note* |
|---|---|---|---|---|---|---|---|
| 84 | t-Bu | H | 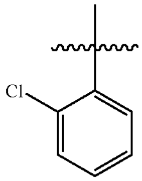 | 5-OMe | 3.82 | 400.2 | I |
| 85 | t-Bu | H | 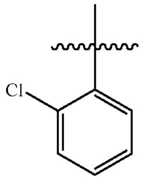 | 4-F | 3.99 | 388.1 | I |
| 86 | 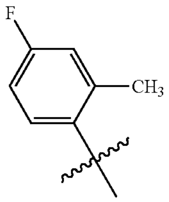 | H | 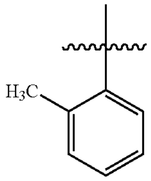 | — | 4.12 | 402.2 | I |
| 87 | 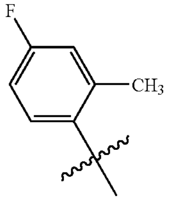 | H | 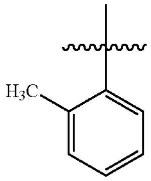 | 5-OMe | 4.08 | 432.2 | I |
| 88 | Ph | H | 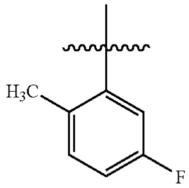 | — | 4 | 388.2 | J |
| 89 | 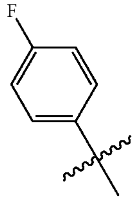 | H | 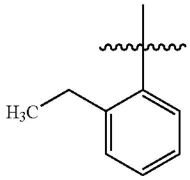 | — | 3.79 | 402.2 | J |

TABLE 1a-continued
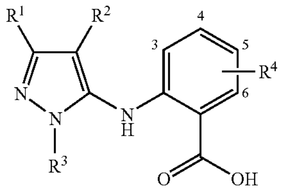
| Ex. No. | $R^1$ | $R^2$ | $R^3$ | $R^4$ | LC-MS RT (min) | LC-MS $[M + H]^+$ | Note* |
|---|---|---|---|---|---|---|---|
| 90 | 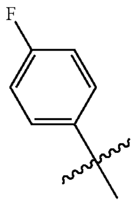 | H | 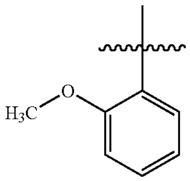 | 4-F | 4 | 422.2 | J |
| 91 | 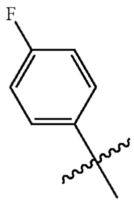 | H | 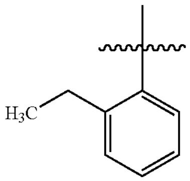 | 5-OMe | 3.76 | 432.2 | J |
| 92 | 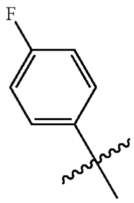 | H | 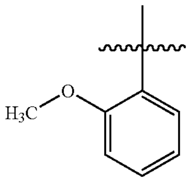 | 4,5-Di-OMe | 3.69 | 464.2 | J |
| 93 | 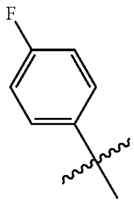 | H | 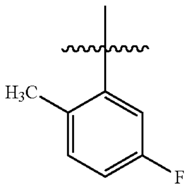 | 5-OMe | 3.71 | 436.2 | J |
| 94 | 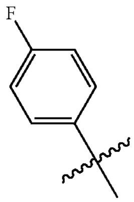 | H | 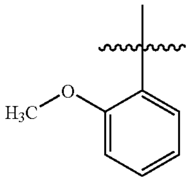 | 5-Me | 4.03 | 418.2 | J |
| 95 | 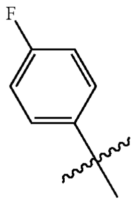 | H | 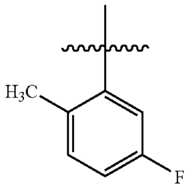 | 5-Me | 3.88 | 420.2 | J |

TABLE 1a-continued
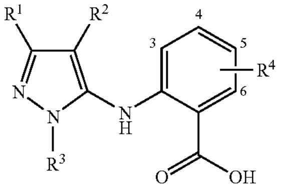
| Ex. No. | $R^1$ | $R^2$ | $R^3$ | $R^4$ | LC-MS RT (min) | LC-MS $[M + H]^+$ | Note* |
|---|---|---|---|---|---|---|---|
| 96 | 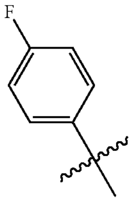 | H | 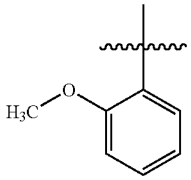 | 5-OMe | 3.87 | 434.2 | J |
| 97 | 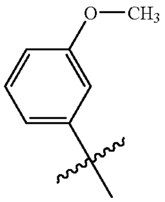 | H | 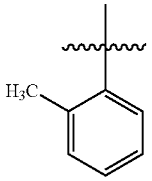 | 4-F | 3.66 | 418.2 | J |
| 98 | 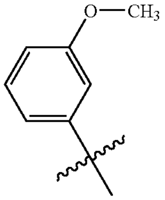 | H | 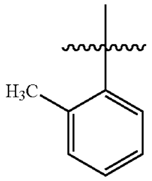 | 4,5-Di-OMe | 3.7 | 460.2 | J |
| 99 | 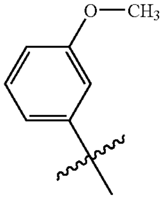 | H | 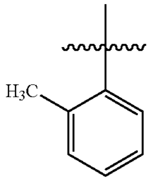 | — | 3.89 | 400.2 | J |
| 100 | 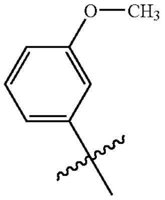 | H | 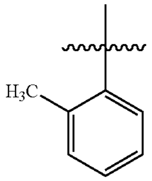 | 5-OMe | 3.86 | 430.2 | J |
| 101 | 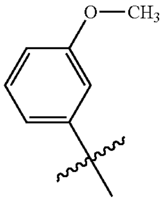 | H | 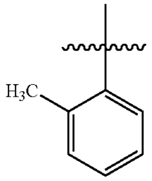 | 5-Me | 4.03 | 414.2 | J |

TABLE 1a-continued
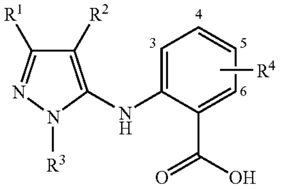
| Ex. No. | $R^1$ | $R^2$ | $R^3$ | $R^4$ | LC-MS RT (min) | LC-MS $[M + H]^+$ | Note* |
|---|---|---|---|---|---|---|---|
| 102 | Me | 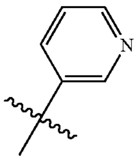 | 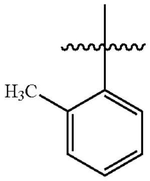 | 5-Cl | 2.89 | 419.2 | K |
| 103 | t-Bu | Me | 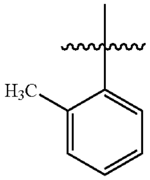 | — | 4.07 | 364.2 | K |
| 104 | t-Bu | Me | 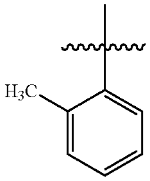 | 5-OMe | 4.01 | 394.2 | K |
| 105 | 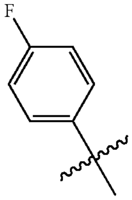 | Me | 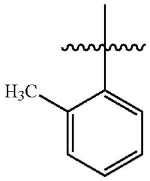 | 5-OMe | 3.8 | 424.2 | K |
| 106 | t-Bu | Me | 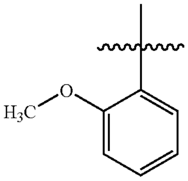 | — | 3.58 | 380.2 | K |
| 107 | t-Bu | Me | 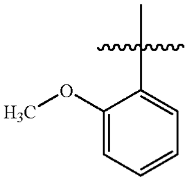 | 5-OMe | 3.52 | 410.2 | K |
*Note: Origin of the aminopyrazole used for the coupling reaction: c = commercial; H, I, J, K = using the methods outlined in Reaction Schemes I, J, or K as described above.

TABLE 1b

| Ex. No. | IUPAC Name |
|---|---|
| 5 | 2-[(1-ethyl-1H-pyrazol-5-yl)amino]benzoic acid |
| 6 | 2-[(1-phenyl-1H-pyrazol-5-yl)amino-5-(methylthio)]benzoic acid |
| 7 | 2-[(1,3-dimethyl-1H-pyrazol-5-yl)amino]-4-fluorobenzoic acid trifluoroacetate |
| 8 | 2-[(1,3-dimethyl-1H-pyrazol-5-yl)amino]-3-(trifluoromethyl)benzoic acid |
| 9 | 2-[(1-benzyl-3-methyl-1H-pyrazol-5-yl)amino]-4-fluorobenzoic acid |
| 10 | 5-methoxy-2-[(3-methyl-1-phenyl-1H-pyrazol-5-yl)amino]benzoic acid |
| 11 | 2-[(3-tert-butyl-1-methyl-1H-pyrazol-5-yl)amino]benzoic acid |
| 12 | 2-[(3-tert-butyl-1-methyl-1H-pyrazol-5-yl)amino]-5-(methylthio)benzoic acid |
| 13 | 2-[(3-tert-butyl-1-ethyl-1H-pyrazol-5-yl)amino]-4,5-dimethoxybenzoic acid |
| 14 | 2-{[3-tert-butyl-1-(2-methylphenyl)-1H-pyrazol-5-yl]amino}benzoic acid |
| 15 | 2-{[3-tert-butyl-1-(2-methylphenyl)-1H-pyrazol-5-yl]amino}-4,5-dimethoxybenzoic acid |
| 16 | 2-{[3-tert-butyl-1-(2,4-dimethylphenyl)-1H-pyrazol-5-yl]amino}-5-methoxybenzoic acid |
| 17 | 2-{[3-tert-butyl-1-(2-ethylphenyl)-1H-pyrazol-5-yl]amino}-4,5-dimethoxybenzoic acid |
| 18 | 2-{[3-tert-butyl-1-(2-ethylphenyl)-1H-pyrazol-5-yl]amino}benzoic acid |
| 19 | 2-{[3-tert-butyl-1-(2-ethylphenyl)-1H-pyrazol-5-yl]amino}-5-methoxybenzoic acid |
| 20 | 2-{[3-tert-butyl-1-(2-methylphenyl)-1H-pyrazol-5-yl]amino}-6-fluorobenzoic acid |
| 21 | 2-{[3-tert-butyl-1-(2,5-dimethylphenyl)-1H-pyrazol-5-yl]amino}-4-fluorobenzoic acid |
| 22 | 2-{[3-tert-butyl-1-(2,5-dimethylphenyl)-1H-pyrazol-5-yl]amino}-5-fluorobenzoic acid |
| 23 | 2-{[3-tert-butyl-1-(2,5-dimethylphenyl)-1H-pyrazol-5-yl]amino}-6-fluorobenzoic acid |
| 24 | 2-{[3-tert-butyl-1-(2,5-dimethylphenyl)-1H-pyrazol-5-yl]amino}-4-methylbenzoic acid |
| 25 | 2-{[3-tert-butyl-1-(2,5-dimethylphenyl)-1H-pyrazol-5-yl]amino}-5-methylbenzoic acid |
| 26 | 2-{[3-tert-butyl-1-(4-chlorophenyl)-1H-pyrazol-5-yl]amino}-4,5-dimethoxybenzoic acid |
| 27 | 2-{[3-tert-butyl-1-(2-methoxyphenyl)-1H-pyrazol-5-yl]amino}-5-methoxybenzoic acid |
| 28 | 4,5-dimethoxy-2-[(1-methyl-3-phenyl-1H-pyrazol-5-yl)amino]benzoic acid trifluoroacetate |
| 29 | 2-[(1,3-diphenyl-1H-pyrazol-5-yl)amino]-5-methoxybenzoic acid |
| 30 | 2-{[1-(2-methylphenyl)-3-phenyl-1H-pyrazol-5-yl]amino}benzoic acid |
| 31 | 4,5-dimethoxy-2-{[1-(2-methylphenyl)-3-phenyl-1H-pyrazol-5-yl]amino}benzoic acid |
| 32 | 5-methoxy-2-{[1-(2-methylphenyl)-3-phenyl-1H-pyrazol-5-yl]amino}benzoic acid |
| 33 | 2-{[1-(2,5-dimethylphenyl)-3-phenyl-1H-pyrazol-5-yl]amino}-4-fluorobenzoic acid |
| 34 | 2-{[1-(2,5-dimethylphenyl)-3-phenyl-1H-pyrazol-5-yl]amino}-6-fluorobenzoic acid |
| 35 | 2-{[1-(2,5-dimethylphenyl)-3-phenyl-1H-pyrazol-5-yl]amino}-4-methylbenzoic acid |
| 36 | 2-{[1-(2,5-dimethylphenyl)-3-phenyl-1H-pyrazol-5-yl]amino}-5-methylbenzoic acid |
| 37 | 2-{[1-(2,5-dimethylphenyl)-3-phenyl-1H-pyrazol-5-yl]amino}benzoic acid |
| 38 | 2-{[1-(2,5-dimethylphenyl)-3-phenyl-1H-pyrazol-5-yl]amino}-5-methoxybenzoic acid |
| 39 | 2-{[1-(2,5-dimethylphenyl)-3-phenyl-1H-pyrazol-5-yl]amino}-4,5-dimethoxybenzoic acid |
| 40 | 4-fluoro-2-{[1-(2-methylphenyl)-3-phenyl-1H-pyrazol-5-yl]amino}benzoic acid |
| 41 | 2-fluoro-6-{[1-(2-methylphenyl)-3-phenyl-1H-pyrazol-5-yl]amino}benzoic acid |
| 42 | 4-chloro-2-{[1-(2-methylphenyl)-3-phenyl-1H-pyrazol-5-yl]amino}benzoic acid |
| 43 | 5-methyl-2-{[1-(2-methylphenyl)-3-phenyl-1H-pyrazol-5-yl]amino}benzoic acid |
| 44 | 2-{[1-(2-ethylphenyl)-3-phenyl-1H-pyrazol-5-yl]amino}-5-methoxybenzoic acid |
| 45 | 2-{[1-(2-ethylphenyl)-3-phenyl-1H-pyrazol-5-yl]amino}-4,5-dimethoxybenzoic acid |
| 46 | 2-{[3-(4-fluorophenyl)-1-phenyl-1H-pyrazol-5-yl]amino}-5-methoxybenzoic acid |
| 47 | 2-{[3-(4-fluorophenyl)-1-(2-methylphenyl)-1H-pyrazol-5-yl]amino}-5-methoxybenzoic acid |
| 48 | 2-{[3-(4-methoxyphenyl)-1-(4-methylphenyl)-1H-pyrazol-5-yl]amino}benzoic acid |
| 49 | 2-{[1-(2-methylphenyl)-3-(4-methylphenyl)-1H-pyrazol-5-yl]amino}benzoic acid |

TABLE 1b-continued

| Ex. No. | IUPAC Name |
|---|---|
| 50 | 5-methoxy-2-{[1-(2-methylphenyl)-3-(4-methylphenyl)-1H-pyrazol-5-yl]amino}benzoic acid |
| 51 | 4,5-dimethoxy-2-{[1-(2-methylphenyl)-3-(4-methylphenyl)-1H-pyrazol-5-yl]amino}benzoic acid |
| 52 | 2-{[3-(4-methoxyphenyl)-1-(2-methylphenyl)-1H-pyrazol-5-yl]amino}benzoic acid |
| 53 | 5-methoxy-2-{[3-(4-methoxyphenyl)-1-(2-methylphenyl)-1H-pyrazol-5-yl]amino}benzoic acid |
| 54 | 2-{[3-(4-chlorophenyl)-1-(2-methylphenyl)-1H-pyrazol-5-yl]amino}-4,5-dimethoxybenzoic acid |
| 55 | 2-{[1,3-bis(2-methylphenyl)-1H-pyrazol-5-yl]amino}-5-methoxybenzoic acid |
| 56 | 4-fluoro-2-{[3-(4-fluorophenyl)-1-(2-methylphenyl)-1H-pyrazol-5-yl]amino}benzoic acid |
| 57 | 2-fluoro-6-{[3-(4-fluorophenyl)-1-(2-methylphenyl)-1H-pyrazol-5-yl]amino}benzoic acid |
| 58 | 2-{[3-(4-fluorophenyl)-1-(2-methylphenyl)-1H-pyrazol-5-yl]amino}-4-methylbenzoic acid |
| 59 | 2-{[3-(4-fluorophenyl)-1-(2-methylphenyl)-1H-pyrazol-5-yl]amino}-5-methylbenzoic acid |
| 60 | 2-{[1,3-bis(2-methylphenyl)-1H-pyrazol-5-yl]amino}benzoic acid |
| 61 | 4-fluoro-2-{[1-(2-methylphenyl)-3-(4-methylphenyl)-1H-pyrazol-5-yl]amino}benzoic acid |
| 62 | 2-fluoro-6-{[1-(2-methylphenyl)-3-(4-methylphenyl)-1H-pyrazol-5-yl]amino}benzoic acid |
| 63 | 4-chloro-2-{[1-(2-methylphenyl)-3-(4-methylphenyl)-1H-pyrazol-5-yl]amino}benzoic acid |
| 64 | 4-methyl-2-{[1-(2-methylphenyl)-3-(4-methylphenyl)-1H-pyrazol-5-yl]amino}benzoic acid |
| 65 | 5-methyl-2-{[1-(2-methylphenyl)-3-(4-methylphenyl)-1H-pyrazol-5-yl]amino}benzoic acid |
| 66 | 2-{[1-(2,5-dimethylphenyl)-3-(4-fluorophenyl)-1H-pyrazol-5-yl]amino}-4-fluorobenzoic acid |
| 67 | 2-{[1-(2,5-dimethylphenyl)-3-(4-fluorophenyl)-1H-pyrazol-5-yl]amino}-4-fluorobenzoic acid |
| 68 | 2-{[1-(2,5-dimethylphenyl)-3-(4-fluorophenyl)-1H-pyrazol-5-yl]amino}-6-fluorobenzoic acid |
| 69 | 2-{[1-(2,5-dimethylphenyl)-3-(4-fluorophenyl)-1H-pyrazol-5-yl]amino}-4-methylbenzoic acid |
| 70 | 2-{[1-(2,5-dimethylphenyl)-3-(4-fluorophenyl)-1H-pyrazol-5-yl]amino}-5-methylbenzoic acid |
| 71 | 2-{[1-(2,5-dimethylphenyl)-3-(4-fluorophenyl)-1H-pyrazol-5-yl]amino}-5-methoxybenzoic acid |
| 72 | 2-{[1-(2,5-dimethylphenyl)-3-(4-fluorophenyl)-1H-pyrazol-5-yl]amino}-4,5-dimethoxybenzoic acid |
| 73 | 2-{[1-(2-methylphenyl)-3-(3-methylphenyl)-1H-pyrazol-5-yl]amino}benzoic acid |
| 74 | 5-methoxy-2-{[1-(2-methylphenyl)-3-(3-methylphenyl)-1H-pyrazol-5-yl]amino}benzoic acid |
| 75 | 2-fluoro-6-{[4-(4-fluorophenyl)-3-methyl-1-(2-methylphenyl)-1H-pyrazol-5-yl]amino}benzoic acid |
| 76 | 2-{[3-tert-butyl-1-(5-fluoro-2-methylphenyl)-1H-pyrazol-5-yl]amino}-6-fluorobenzoic acid |
| 77 | 2-{[3-tert-butyl-1-(5-fluoro-2-methylphenyl)-1H-pyrazol-5-yl]amino}-4-fluorobenzoic acid |
| 78 | 2-{[3-tert-butyl-1-(2-methoxyphenyl)-1H-pyrazol-5-yl]amino}-4-fluorobenzoic acid |
| 79 | 2-{[3-tert-butyl-1-(2-methoxyphenyl)-1H-pyrazol-5-yl]amino}-5-methylbenzoic acid |
| 80 | 2-({3-tert-butyl-1-[2-(methylthio)phenyl]-1H-pyrazol-5-yl}amino)-5-methoxybenzoic acid |
| 81 | 2-{[3-tert-butyl-1-(2-ethoxyphenyl)-1H-pyrazol-5-yl]amino}benzoic acid |
| 82 | 2-{[3-tert-butyl-1-(2-ethoxyphenyl)-1H-pyrazol-5-yl]amino}-5-methoxybenzoic acid |
| 83 | 2-{[3-tert-butyl-1-(2-ethoxyphenyl)-1H-pyrazol-5-yl]amino}-5-methylbenzoic acid |
| 84 | 2-{[3-tert-butyl-1-(2-chlorophenyl)-1H-pyrazol-5-yl]amino}-5-methoxybenzoic acid |
| 85 | 2-{[3-tert-butyl-1-(2-chlorophenyl)-1H-pyrazol-5-yl]amino}-4-fluorobenzoic acid |
| 86 | 2-{[3-(4-fluoro-2-methylphenyl)-1-(2-methylphenyl)-1H-pyrazol-5-yl]amino}benzoic acid |
| 87 | 2-{[3-(4-fluoro-2-methylphenyl)-1-(2-methylphenyl)-1H-pyrazol-5-yl]amino}-5-methoxybenzoic acid |
| 88 | 2-{[1-(5-fluoro-2-methylphenyl)-3-phenyl-1H-pyrazol-5-yl]amino}benzoic acid |
| 89 | 2-{[1-(2-ethylphenyl)-3-(4-fluorophenyl)-1H-pyrazol-5-yl]amino}benzoic acid |

TABLE 1b-continued

| Ex. No. | IUPAC Name |
|---|---|
| 90 | 4-fluoro-2-{[3-(4-fluorophenyl)-1-(2-methoxyphenyl)-1H-pyrazol-5-yl]amino}benzoic acid |
| 91 | 2-{[1-(2-ethylphenyl)-3-(4-fluorophenyl)-1H-pyrazol-5-yl]amino}-5-methoxybenzoic acid |
| 92 | 2-{[3-(4-fluorophenyl)-1-(2-methoxyphenyl)-1H-pyrazol-5-yl]amino}-4,5-dimethoxybenzoic acid |
| 93 | 2-{[1-(5-fluoro-2-methylphenyl)-3-(4-fluorophenyl)-1H-pyrazol-5-yl]amino}-5-methoxybenzoic acid |
| 94 | 2-{[3-(4-fluorophenyl)-1-(2-methoxyphenyl)-1H-pyrazol-5-yl]amino}-5-methylbenzoic acid |
| 95 | 2-{[1-(5-fluoro-2-methylphenyl)-3-(4-fluorophenyl)-1H-pyrazol-5-yl]amino}-5-methylbenzoic acid |
| 96 | 2-{[3-(4-fluorophenyl)-1-(2-methoxyphenyl)-1H-pyrazol-5-yl]amino}-5-methoxybenzoic acid |
| 97 | 4-fluoro-2-{[3-(3-methoxyphenyl)-1-(2-methylphenyl)-1H-pyrazol-5-yl]amino}benzoic acid |
| 98 | 4,5-dimethoxy-2-{[3-(3-methoxyphenyl)-1-(2-methylphenyl)-1H-pyrazol-5-yl]amino}benzoic acid |
| 99 | 2-{[3-(3-methoxyphenyl)-1-(2-methylphenyl)-1H-pyrazol-5-yl]amino}benzoic acid |
| 100 | 5-methoxy-2-{[3-(3-methoxyphenyl)-1-(2-methylphenyl)-1H-pyrazol-5-yl]amino}benzoic acid |
| 101 | 2-{[3-(3-methoxyphenyl)-1-(2-methylphenyl)-1H-pyrazol-5-yl]amino}-5-methylbenzoic acid |
| 102 | 5-chloro-2-{[3-methyl-1-(2-methylphenyl)-4-pyridin-3-yl-1H-pyrazol-5-yl]amino}benzoic acid trifluoroacetate |
| 103 | 2-{[3-tert-butyl-4-methyl-1-(2-methylphenyl)-1H-pyrazol-5-yl]amino}benzoic acid |
| 104 | 2-{[3-tert-butyl-4-methyl-1-(2-methylphenyl)-1H-pyrazol-5-yl]amino}-5-methoxybenzoic acid |
| 105 | 2-{[3-(4-fluorophenyl)-4-methyl-1-(2-methylphenyl)-1H-pyrazol-5-yl]amino}-5-methoxybenzoic acid |
| 106 | 2-{[3-tert-butyl-1-(2-methoxyphenyl)-4-methyl-1H-pyrazol-5-yl]amino}benzoic acid |
| 107 | 2-{[3-tert-butyl-1-(2-methoxyphenyl)-4-methyl-1H-pyrazol-5-yl]amino}-5-methoxybenzoic acid |

EXAMPLE 108

Preparation of methyl 2-{[3-cyclopentyl-1-(2-methylphenyl)-1H-pyrazol-5-yl]amino}benzoate

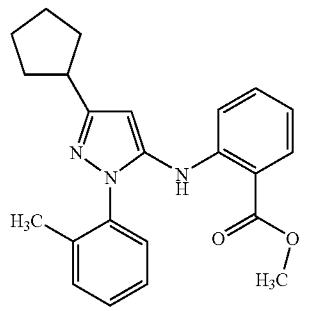

A mixture of 3-cyclopentyl-1-(2-methylphenyl)-1H-pyrazol-5-amine (Intermediate B, 400 mg, 1.66 mmol), methyl 2-bromobenzoate (297 mg, 1.38 mmol), cesium carbonate (630 mg, 1.93 mmol), BINAP (87 mg, 0.14 mmol), and $Pd_2(dba)_3$ (72 mg, 0.07 mmol) in anhydrous toluene (4 mL) was heated to 110° C. for 16 h under an argon atmosphere. The reaction mixture was cooled to rt, diluted with ethyl acetate, filtered, and concentrated under reduced pressure. The residue was purified by silica gel chromatography using EtOAc/Hex (1:8, v/v) as the eluent. The product was obtained as a light yellow oil (303 mg, 58%). ES-MS m/z 376.3 ($MH^+$); HPLC RT (min) 3.94.

EXAMPLE 109

Preparation of 2-{[3-cyclopentyl-1-(2-methylphenyl)-1H-pyrazol-5-yl]amino}benzoic acid

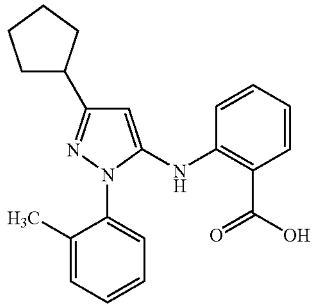

To a solution of methyl 2-{[3-cyclopentyl-1-(2-methylphenyl)-1H-pyrazol-5-yl]amino}benzoate (0.59 mmol, 220 mg) in MeOH (1.8 mL) was added THF (5.4 mL) and 1N aqueous NaOH (1.8 mL). The reaction was stirred at rt for 21 h. The organic solvents were removed under reduced pressure, the residue was diluted with water, and the aqueous solution extracted with diethylether (2×5 mL). The aqueous layer was acidified to pH=1 to 2 with 1N aqueous HCl. The mixture was extracted with ethyl acetate (3×5 mL). After removal of the solvent under reduced pressure, the product was obtained as a white solid (169 mg, 79%). $^1$H NMR (400 MHz, DMSO-$d_6$) δ 1.58-1.62 (m, 2H), 1.65-1.78 (m, 4H), 1.90-2.01 (m, 2H), 2.06 (s, 3H), 2.99-3.10 (m, 1H), 6.23 (s, 1H), 6.80 (t, 1H), 7.20-7.30 (m, 3H), 7.30-7.40 (m, 2H), 7.42-7.51 (m, 1H), 7.81 (d, 1H), 9.84 (s, 1H), 13.14 (s, 1H). ES-MS m/z 362.3 ($MH^+$), HPLC RT (min) 3.39.

The following analogs were synthesized using the method described above for Example 109.

In Table 2a, the locant of the $R^4$ group(s) is defined as shown.

TABLE 2a

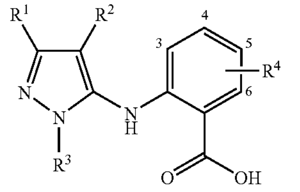

| Ex. No. | $R^1$ | $R^2$ | $R^3$ | $R^4$ | LC-MS RT (min) | LC-MS $[M + H]^+$ | Note* |
|---|---|---|---|---|---|---|---|
| 110 | t-Bu | H | Me | 5-Me | 3.31 | 288.1 | c |
| 111 | t-Bu | H | Ph | 5-OMe | 3.30 | 366.2 | I |
| 112 | t-Bu | H | 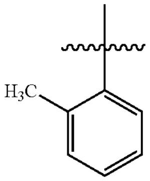 | 5-F | 3.90 | 368.2 | I |
| 113 | t-Bu | H | 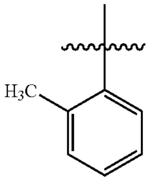 | 5-Me | 3.47 | 364.2 | I |
| 114 | t-Bu | H | 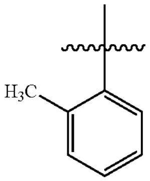 | 4-Me | 3.47 | 364.2 | I |
| 115 | t-Bu | H | 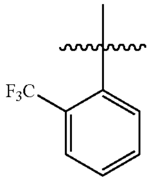 | 5-OMe | 3.44 | 434.2 | I |
| 116 | t-Bu | H | 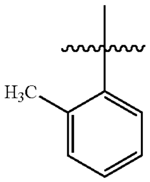 | 5-$OCHF_2$ | 3.51 | 416.2 | |

TABLE 2a-continued
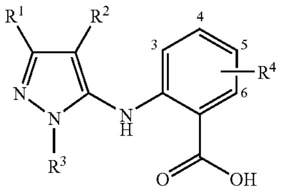
| Ex. No. | $R^1$ | $R^2$ | $R^3$ | $R^4$ | LC-MS RT (min) | LC-MS $[M + H]^+$ | Note* |
|---|---|---|---|---|---|---|---|
| 117 | t-Bu | H | 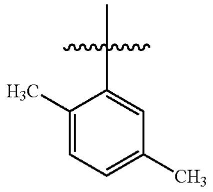 | 5-OMe | 3.54 | 394.2 | I |
| 118 | t-Bu | H | 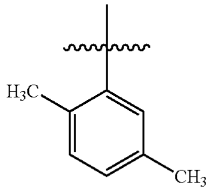 | — | 3.66 | 364.2 | I |
| 119 | t-Bu | H | 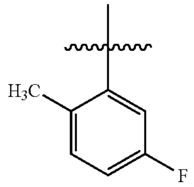 | 5-OMe | 3.45 | 398.2 | I |
| 120 | t-Bu | H | 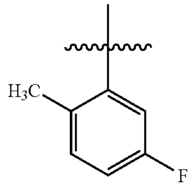 | — | 3.52 | 368.2 | I |
| 121 | t-Bu | H | 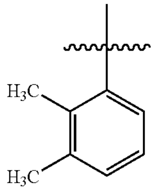 | — | 3.46 | 364.3 | I |
| 122 | t-Bu | H | 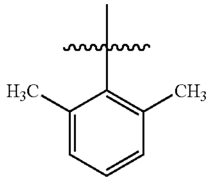 | — | 3.43 | 364.3 | I |

TABLE 2a-continued
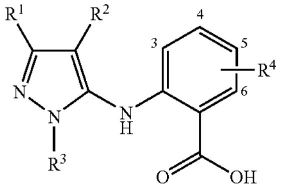
| Ex. No. | $R^1$ | $R^2$ | $R^3$ | $R^4$ | LC-MS RT (min) | LC-MS $[M + H]^+$ | Note* |
|---|---|---|---|---|---|---|---|
| 123 | 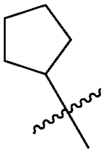 | H | 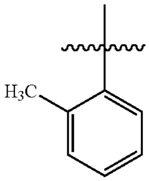 | 5-OMe | 3.27 | 391.9 | I |
| 124 | 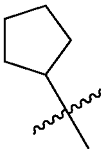 | H | 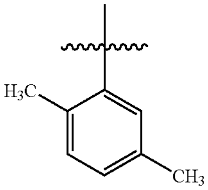 | 5-OMe | 3.40 | 406.3 | I |
| 125 | 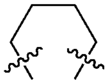 | | Ph | 5-OMe | 3.06 | 364.2 | I |
| 126 | Me | 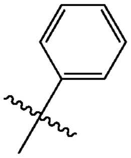 | Ph | 5-OMe | 3.66 | 400.2 | c |
| 127 | 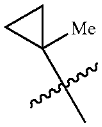 | H | 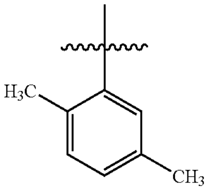 | 5-OMe | 3.43 | 392.2 | I |
| 128 | 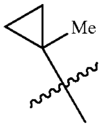 | H | 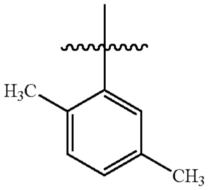 | — | 3.53 | 362.2 | I |
| 129 | 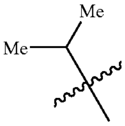 | H | 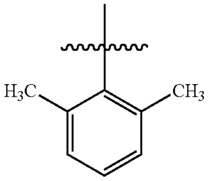 | — | 3.32 | 350.2 | I |

TABLE 2a-continued
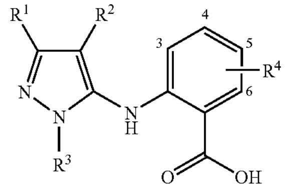
| Ex. No. | $R^1$ | $R^2$ | $R^3$ | $R^4$ | LC-MS RT (min) | LC-MS $[M + H]^+$ | Note* |
| --- | --- | --- | --- | --- | --- | --- | --- |
| 130 | 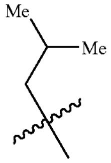 | H | 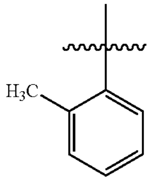 | 5-OMe | 3.22 | 380.3 | I |
| 131 | 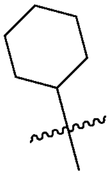 | H | 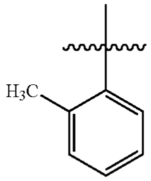 | — | 3.59 | 376.3 | I |
| 132 | 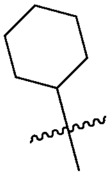 | H | 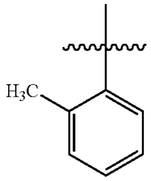 | 5-OMe | 3.47 | 406.3 | I |
| 133 | $CF_3$ | Ph | Me | 5-OMe | 3.21 | 392.2 | I |
| 134 | $CF_3$ | Ph | 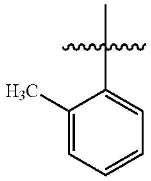 | 5-OMe | 3.7 | 468.2 | I |
| 135 | $CF_3$ | Ph | 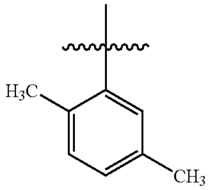 | 5-OMe | 3.82 | 482.2 | I |
| 136 | t-Bu | H | 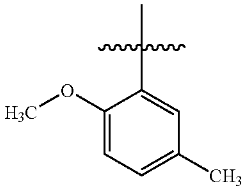 | — | 3.44 | 380.3 | I |

TABLE 2a-continued
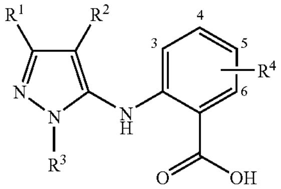
| Ex. No. | $R^1$ | $R^2$ | $R^3$ | $R^4$ | LC-MS RT (min) | LC-MS $[M + H]^+$ | Note* |
|---|---|---|---|---|---|---|---|
| 137 | t-Bu | H | 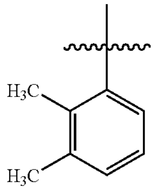 | 5-OMe | 3.33 | 394.3 | I |
| 138 | t-Bu | H | 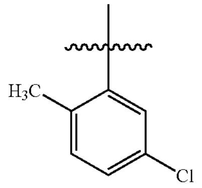 | — | 3.79 | 384.2 | I |
| 139 | t-Bu | H | 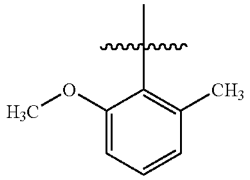 | — | 3.41 | 380.2 | I |
| 140 | t-Bu | H | 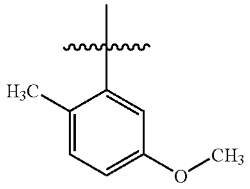 | 5-OMe | 3.32 | 410.3 | I |
| 141 | t-Bu | H | 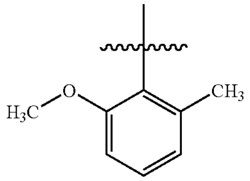 | 5-OMe | 3.27 | 410.2 | I |
| 142 | t-Bu | H | 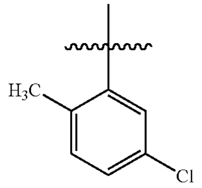 | 5-OMe | 3.62 | 414.4 | I |
| 143 | t-Bu | H | 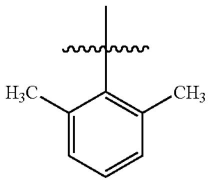 | 5-OMe | 3.3 | 394.4 | I |

TABLE 2a-continued
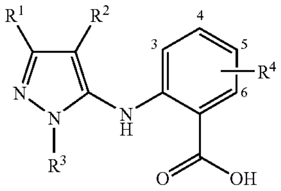
| Ex. No. | $R^1$ | $R^2$ | $R^3$ | $R^4$ | LC-MS RT (min) | LC-MS $[M + H]^+$ | Note* |
|---|---|---|---|---|---|---|---|
| 144 | Me | Ph | 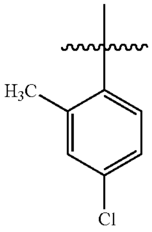 | 5-OMe | 3.53 | 448.1 | I |
| 145 | Me | Ph | 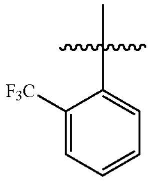 | 5-OMe | 3.29 | 468.2 | I |
| 146 | Me | Ph | 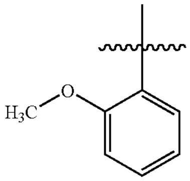 | 5-Me | 3.29 | 414.2 | I |
| 147 | Me | Ph | 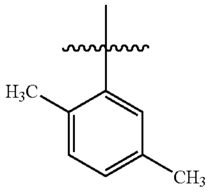 | 5-OMe | 3.38 | 428.3 | I |
| 148 | Me | Ph | 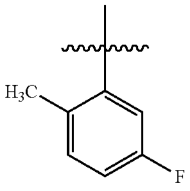 | 5-OMe | 3.31 | 432.2 | I |
| 149 | Me | Ph | 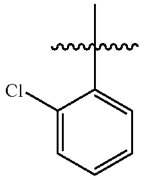 | 5-OMe | 3.29 | 434.1 | I |

TABLE 2a-continued

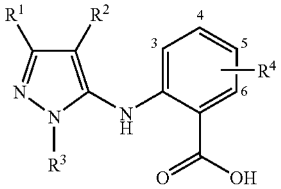

| Ex. No. | $R^1$ | $R^2$ | $R^3$ | $R^4$ | LC-MS RT (min) | LC-MS $[M + H]^+$ | Note* |
|---|---|---|---|---|---|---|---|
| 150 | 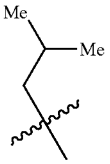 | H | 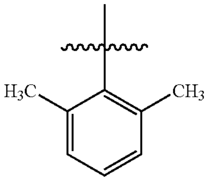 | — | 3.4 | 364.3 | I |
| 151 | 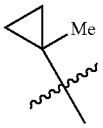 | H | 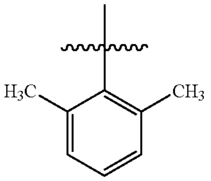 | 5-OMe | 3.23 | 392.3 | I |
| 152 | 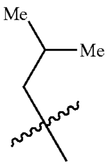 | H | 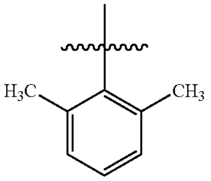 | 5-OMe | 3.28 | 394.3 | I |
| 153 | 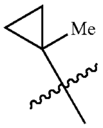 | H | 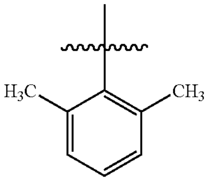 | — | 3.33 | 362.3 | |
| 154 | 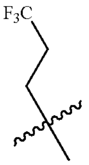 | H | 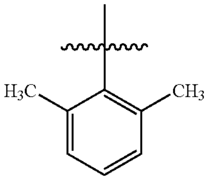 | 5-OMe | 3.37 | 434.2 | I |

*Note: Origin of the aminopyrazole used for the coupling reaction: c = commercial; I = using the method of Reaction Scheme I as previously described TABLE 2b

| Ex. No. | IUPAC Name |
|---|---|
| 110 | 2-[(3-tert-butyl-1-methyl-1H-pyrazol-5-yl)amino]-5-methylbenzoic acid |
| 111 | 2-[(3-tert-butyl-1-phenyl-1H-pyrazol-5-yl)amino]-5-methoxybenzoic acid |
| 112 | 2-{[3-tert-butyl-1-(2-methylphenyl)-1H-pyrazol-5-yl]amino}-5-fluorobenzoic acid |
| 113 | 2-{[3-tert-butyl-1-(2-methylphenyl)-1H-pyrazol-5-yl]amino}-5-methylbenzoic acid |
| 114 | 2-{[3-tert-butyl-1-(2-methylphenyl)-1H-pyrazol-5-yl]amino}-4-methylbenzoic acid |
| 115 | 2-({3-tert-butyl-1-[2-(trifluoromethyl)phenyl]-1H-pyrazol-5-yl}amino)-5-methoxybenzoic acid |
| 116 | 2-{[3-tert-butyl-1-(2-methylphenyl)-1H-pyrazol-5-yl]amino}-5- |

TABLE 2b-continued

| Ex. No. | IUPAC Name |
|---|---|
| | (difluoromethoxy)benzoic acid |
| 117 | 2-{[3-tert-butyl-1-(2,5-dimethylphenyl)-1H-pyrazol-5-yl]amino}-5-methoxybenzoic acid |
| 118 | 2-{[3-tert-butyl-1-(2,5-dimethylphenyl)-1H-pyrazol-5-yl]amino}benzoic acid |
| 119 | 2-{[3-tert-butyl-1-(5-fluoro-2-methylphenyl)-1H-pyrazol-5-yl]amino}-5-methoxybenzoic acid |
| 120 | 2-{[3-tert-butyl-1-(5-fluoro-2-methylphenyl)-1H-pyrazol-5-yl]amino}benzoic acid |
| 121 | 2-{[3-tert-butyl-1-(2,3-dimethylphenyl)-1H-pyrazol-5-yl]amino}benzoic acid |
| 122 | 2-{[3-tert-butyl-1-(2,6-dimethylphenyl)-1H-pyrazol-5-yl]amino}benzoic acid |
| 123 | 2-{[3-cyclopentyl-1-(2-methylphenyl)-1H-pyrazol-5-yl]amino}-5-methoxybenzoic acid |
| 124 | 2-{[3-cyclopentyl-1-(2,5-dimethylphenyl)-1H-pyrazol-5-yl]amino}-5 methoxybenzoic acid |
| 125 | 5-methoxy-2-[(2-phenyl-4,5,6,7-tetrahydro-2H-indazol-3-yl)amino]benzoic acid |
| 126 | 5-methoxy-2-[(3-methyl-1,4-diphenyl-1H-pyrazol-5-yl)amino]benzoic acid |
| 127 | 2-{[1-(2,5-dimethylphenyl)-3-(1-methylcyclopropyl)-1H-pyrazol-5-yl]amino}-5-methoxybenzoic acid |
| 128 | 2-{[1-(2,5-dimethylphenyl)-3-(1-methylcyclopropyl)-1H-pyrazol-5-yl]amino}benzoic acid |
| 129 | 2-{[1-(2,6-dimethylphenyl)-3-isopropyl-1H-pyrazol-5-yl]amino}benzoic acid |
| 130 | 2-{[3-isobutyl-1-(2-methylphenyl)-1H-pyrazol-5-yl]amino}-5-methoxybenzoic acid |
| 131 | 2-{[3-cyclohexyl-1-(2-methylphenyl)-1H-pyrazol-5-yl]amino}benzoic acid |
| 132 | 2-{[3-cyclohexyl-1-(2-methylphenyl)-1H-pyrazol-5-yl]amino}-5-methoxybenzoic acid |
| 133 | 5-methoxy-2-{[1-methyl-4-phenyl-3-(trifluoromethyl)-1H-pyrazol-5-yl]amino}benzoic acid |
| 134 | 5-methoxy-2-{[1-(2-methylphenyl)-4-phenyl-3-(trifluoromethyl)-1H-pyrazol-5-yl]amino}benzoic acid |
| 135 | 2-{[1-(2,5-dimethylphenyl)-4-phenyl-3-(trifluoromethyl)-1H-pyrazol-5-yl]amino}-5-methoxybenzoic acid |
| 136 | 2-{[3-tert-butyl-1-(2-methoxy-5-methylphenyl)-1H-pyrazol-5-yl]amino}benzoic acid |
| 137 | 2-{[3-tert-butyl-1-(2,3-dimethylphenyl)-1H-pyrazol-5-yl]amino}-5-methoxybenzoic acid |
| 138 | 2-{[3-tert-butyl-1-(5-chloro-2-methylphenyl)-1H-pyrazol-5-yl]amino}benzoic acid |
| 139 | 2-{[3-tert-butyl-1-(2-methoxy-6-methylphenyl)-1H-pyrazol-5-yl]amino}benzoic acid |
| 140 | 2-{[3-tert-butyl-1-(5-methoxy-2-methylphenyl)-1H-pyrazol-5-yl]amino}-5-methoxybenzoic acid |
| 141 | 2-{[3-tert-butyl-1-(2-methoxy-6-methylphenyl)-1H-pyrazol-5-yl]amino}-5-methoxybenzoic acid |
| 142 | 2-{[3-tert-butyl-1-(5-chloro-2-methylphenyl)-1H-pyrazol-5-yl]amino}-5-methoxybenzoic acid |
| 143 | 2-{[3-tert-butyl-1-(2,6-dimethylphenyl)-1H-pyrazol-5-yl]amino}-5-methoxybenzoic acid |
| 144 | 2-{[1-(4-chloro-2-methylphenyl)-3-methyl-4-phenyl-1H-pyrazol-5-yl]amino}-5-methoxybenzoic acid |
| 145 | 5-methoxy-2-({3-methyl-4-phenyl-1-[2-(trifluoromethyl)phenyl]-1H-pyrazol-5-yl}amino)benzoic acid |
| 146 | 2-{[1-(2-methoxyphenyl)-3-methyl-4-phenyl-1H-pyrazol-5-yl]amino}-5-methylbenzoic acid |
| 147 | 2-{[1-(2,5-dimethylphenyl)-3-methyl-4-phenyl-1H-pyrazol-5-yl]amino}-5-methoxybenzoic acid |
| 148 | 2-{[1-(5-fluoro-2-methylphenyl)-3-methyl-4-phenyl-1H-pyrazol-5-yl]amino}-5-methoxybenzoic acid |
| 149 | 2-{[1-(2-chlorophenyl)-3-methyl-4-phenyl-1H-pyrazol-5-yl]amino}-5-methoxybenzoic acid |
| 150 | 2-{[1-(2,6-dimethylphenyl)-3-isobutyl-1H-pyrazol-5-yl]amino}benzoic acid |
| 151 | 2-{[1-(2,6-dimethylphenyl)-3-(1-methylcyclopropyl)-1H-pyrazol-5-yl]amino}-5-methoxybenzoic acid |
| 152 | 2-{[1-(2,6-dimethylphenyl)-3-isobutyl-1H-pyrazol-5-yl]amino}-5-methoxybenzoic acid |
| 153 | 2-{[1-(2,6-dimethylphenyl)-3-(1-methylcyclopropyl)-1H-pyrazol-5-yl]amino}benzoic acid |
| 154 | 2-{[1-(2,6-dimethylphenyl)-3-(3,3,3-trifluoropropyl)-1H-pyrazol-5-yl]amino}-5-methoxybenzoic acid |

EXAMPLE 155

Preparation of methyl 2-[(3-tert-butyl-1-methyl-1H-pyrazol-5-yl)amino]-5-methoxybenzoate

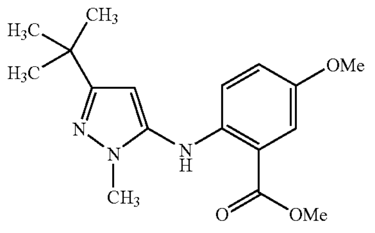

To a 100 mL oven dried flask, was added 5-amino-3-tert-butyl-1-methylpyrazole (2.00 g. 13.1 mmol), methyl 2-bromo-5-methoxybenzoate (2.67 g, 10.9 mmol), cesium carbonate (4.96 g, 15.2 mmol), $Pd_2(dba)_3$ (337 mg, 0.33 mmol), BINAP (338 mg, 0.54 mmol), and toluene (35 mL). The reaction mixture was degassed, placed under an $N_2$ atmosphere, and then stirred at 110° C. for 16 h. The reaction mixture was cooled to rt, and ethyl acetate (30 mL) was added. The mixture was filtered, the filter cake washed with EtOAc (10 mL), and the filtrate concentrated under reduced pressure. The residue was purified by silica gel flash chromatography (eluent: 10 to 30% EtOAc in hexane) to give the title compound as a light yellow oil (1.34 g, 38%). $^1$H NMR (400 MHz, $CDCl_3$) δ 1.28 (s, 9H), 3.63 (s, 3H), 3.78 (s, 3H), 3.94 (s, 3H), 5.97 (s, 1H), 6.82 (d, 1H), 7.10 (dd, 1H), 7.47 (d, 1H).

EXAMPLE 156

Preparation of methyl 2-[(4-bromo-3-tert-butyl-1-methyl-1H-pyrazol-5-yl)amino]-5-methoxybenzoate

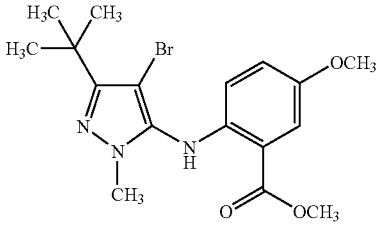

To a solution of 2-(5-tert-butyl-2-methyl-2H-pyrazol-3-ylamino)-5-methoxy-benzoic acid methyl ester (Example 155, 1.34 g, 4.22 mmol) in acetic acid (27 mL), was added dropwise a solution of $Br_2$ (6.74 g, 4.22 mmol) in acetic acid (5 mL). The reaction was stirred for 5 min, and then water (100 mL) was added. The aqueous phase was extracted with EtOAc, and the combined organic layers were washed with water, and then with $NaHCO_3$ (10% aqueous solution) 10 times. The organic layer was then dried ($Na_2SO_4$), filtered, and concentrated under reduced pressure. The residue was purified by silica gel flash chromatography (eluent: 5 to 10% EtOAc in hexane) to give the title compound as a light yellow solid. (1.49 g, 89%). $^1$H NMR (400 MHz, $CDCl_3$) δ 1.40 (s, 9H), 3.66 (s, 3H), 3.78 (s, 3H), 4.05 (s, 3H), 6.32 (d, 1H), 7.06 (dd, 1H), 7.48 (d, 1H).

EXAMPLE 157

Preparation of 2-{[3-tert-butyl-4-(4-methoxyphenyl)-1-methyl-1H-pyrazol-5-yl]amino}-5-methoxy-benzoic acid

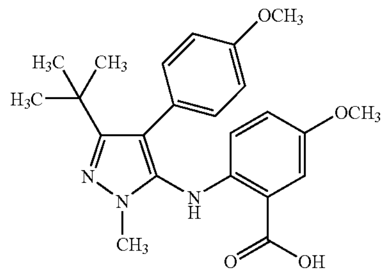

$CF_3COOH$

To a solution 2-(4-bromo-5-tert-butyl-2-methyl-2H-pyrazol-3-ylamino)-5-methoxybenzoic acid methyl ester (Example 96, 100 mg, 0.25 mmol), 4-methoxyphenylboronic acid (153.4 mg, 1.01 mmol), $PdCl_2(dppf).CH_2Cl_2$ (18.46 mg, 0.03 mmol) in a mixture of toluene (6.1 mL) and dioxane (1.22 mL) was added a 2M aqueous solution of sodium carbonate (1.22 mL, 2.44 mmol). A flow of Ar was passed through the reaction mixture for 15 min, and then the reaction was stirred at 75° C. for 18 h. The reaction mixture was then cooled to rt, and filtered through a plug of silica gel. The filtrate was concentrated under reduced pressure, and then the residue was dissolved in a mixture of THF (4 mL), MeOH (2 mL) and water (4 mL). Lithium hydroxide (60 mg, 2.52 mmol) was added, and the mixture was stirred at rt for 18 h. The reaction mixture was then concentrated and the residue purified by preparative HPLC to give the title compound (27.9 mg, 27%) as a white solid. $^1$H NMR (400 MHz, $CDCl_3$) δ 1.21 (s, 9H), 3.61 (s, 3H), 3.74 (s, 6H), 6.41 (d, 1H), 6.70 (d, 2H), 7.04 (dd, 1H), 7.09 (d, 2H), 7.39 (d, 1H). ES-MS m/z 410.2 ($MH^+$); HPLC RT (min) 3.66.

The following analogs, listed in Table 3a, were synthesized using the methods described above. Examples 162, 163, 173, 174, 182, 183, 186, and 187 were obtained as trifluoroacetic acid salts.

In Table 3a, the locant of the $R^4$ group(s) is defined as shown.

TABLE 3a
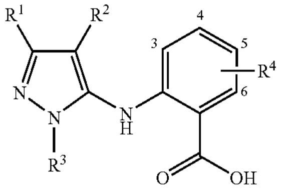
| Ex. No. | $R^1$ | $R^2$ | $R^3$ | $R^4$ | LC-MS RT (min) | LC-MS [M + H $^+$ | Note* |
|---|---|---|---|---|---|---|---|
| 158 | H | Ph | Ph | 5-OMe | 3.65 | 386.2 | c |
| 159 | H | 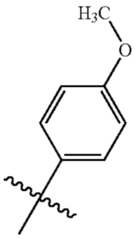 | Ph | 5-OMe | 3.62 | 416.2 | c |
| 160 | H | 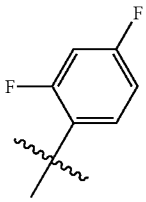 | Ph | 5-OMe | 3.77 | 422.1 | c |
| 161 | H | 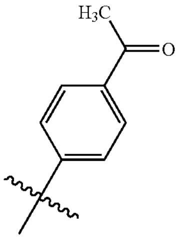 | Ph | 5-OMe | 3.51 | 428.2 | c |
| 162 | H | 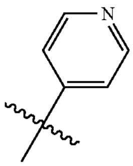 | Ph | 5-OMe | 2.62 | 388.2 | c |
| 163 | H | 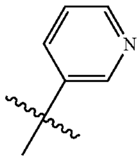 | Ph | 5-OMe | 2.63 | 388.2 | c |
| 164 | Me | Ph | 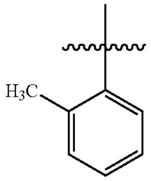 | 5-OMe | 3.71 | 414.2 | J |

TABLE 3a-continued
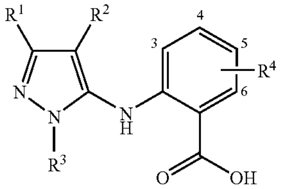
| Ex. No. | $R^1$ | $R^2$ | $R^3$ | $R^4$ | LC-MS RT (min) | LC-MS [M + H + | Note* |
|---|---|---|---|---|---|---|---|
| 165 | Me | 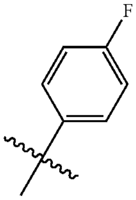 | 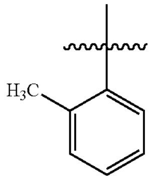 | 5-OMe | 3.75 | 432.2 | J |
| 166 | Me | 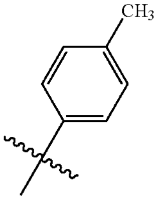 | 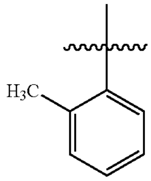 | 5-OMe | 3.84 | 428.2 | J |
| 167 | Me | 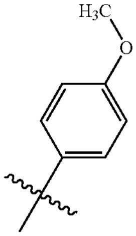 | 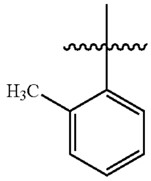 | 5-OMe | 3.67 | 444.2 | J |
| 168 | Me | 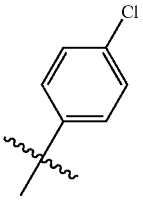 | 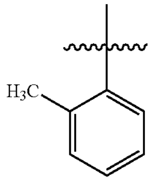 | 5-OMe | 3.92 | 448.2 | J |
| 169 | Me | 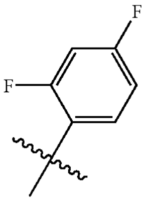 | 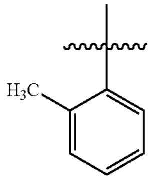 | 5-OMe | 3.30 | 450.2 | J |
| 170 | Me | 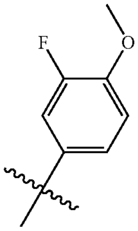 | 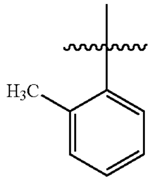 | 5-OMe | 3.22 | 462.2 | J |

TABLE 3a-continued
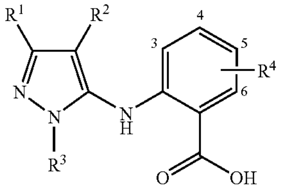
| Ex. No. | $R^1$ | $R^2$ | $R^3$ | $R^4$ | LC-MS RT (min) | LC-MS [M + H $^+$ | Note* |
|---|---|---|---|---|---|---|---|
| 171 | Me | 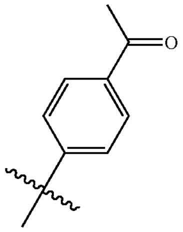 | 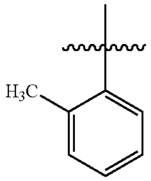 | 5-OMe | 3.07 | 456.2 | J |
| 172 | Me | 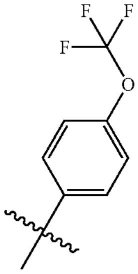 | 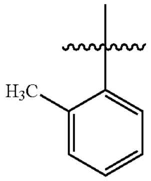 | 5-OMe | 3.57 | 498.2 | J |
| 173 | Me | 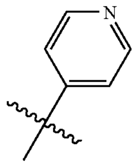 | 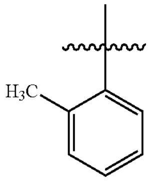 | 5-OMe | 2.65 | 415.2 | J |
| 174 | Me | 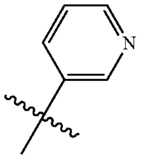 | 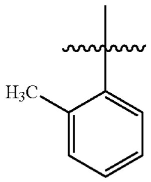 | 5-OMe | 2.71 | 415.2 | J |
| 175 | Me | 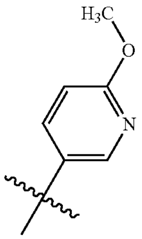 | 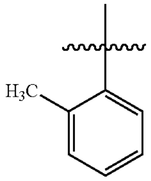 | 5-OMe | 2.96 | 445.1 | J |
| 176 | Me | 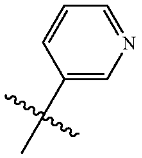 | 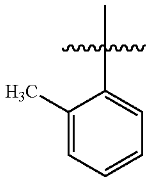 | 5-F | 2.75 | 403.2 | J |

TABLE 3a-continued
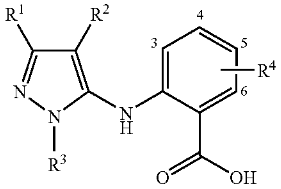
| Ex. No. | $R^1$ | $R^2$ | $R^3$ | $R^4$ | LC-MS RT (min) | LC-MS [M + H + | Note* |
|---|---|---|---|---|---|---|---|
| 177 | Me | 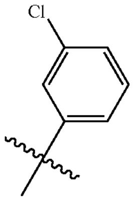 | 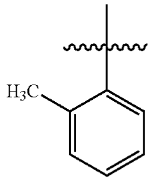 | 5-OMe | 3.52 | 448.2 | J |
| 178 | Me | 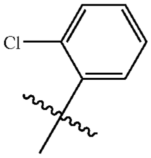 | 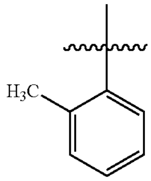 | 5-OMe | 3.31 | 447.9 | J |
| 179 | Me | 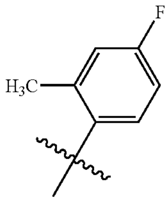 | 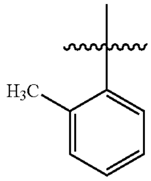 | 5-OMe | 3.44 | 446.2 | J |
| 180 | Me | 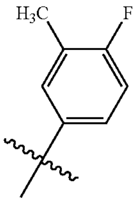 | 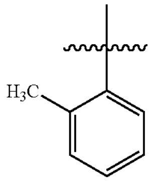 | 5-OMe | 3.50 | 446.2 | J |
| 181 | Me | 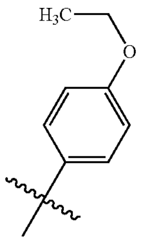 | 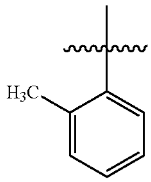 | 5-OMe | 3.45 | 458.2 | J |
| 182 | t-Bu | 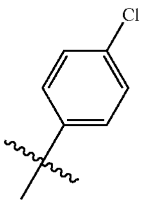 | Me | 5-OMe | 3.92 | 414.2 | c |
| 183 | t-Bu | Ph | Me | 5-OMe | 3.73 | 380.2 | c |

TABLE 3a-continued
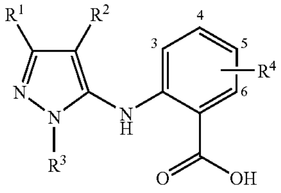
| Ex. No. | $R^1$ | $R^2$ | $R^3$ | $R^4$ | LC-MS RT (min) | LC-MS [M + H + | Note* |
|---|---|---|---|---|---|---|---|
| 184 | t-Bu | 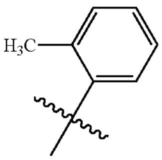 | Me | 5-OMe | 3.79 | 394.2 | c |
| 185 | t-Bu | 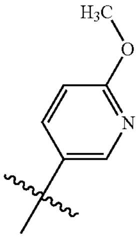 | Me | 5-OMe | 2.97 | 411.2 | c |
| 186 | t-Bu | 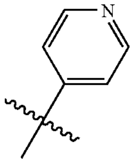 | Me | 5-OMe | 2.65 | 381.2 | c |
| 187 | t-Bu | 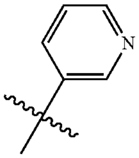 | Me | 5-OMe | 2.68 | 381.2 | c |
| 188 | t-Bu | 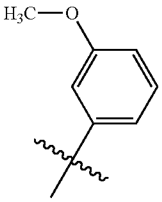 | Me | 5-OMe | 3.7 | 410.2 | c |
| 189 | t-Bu | 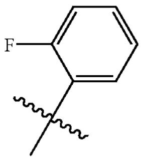 | Me | 5-Me | 3.92 | 382.2 | c |
| 190 | t-Bu | Ph | Me | 5-Me | 3.89 | 364.2 | c |

TABLE 3a-continued
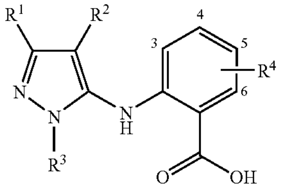
| Ex. No. | $R^1$ | $R^2$ | $R^3$ | $R^4$ | LC-MS RT (min) | LC-MS [M + H $^+$ | Note* |
|---|---|---|---|---|---|---|---|
| 191 | t-Bu | 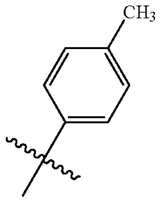 | Me | 5-OMe | 3.84 | 394.2 | c |
| 192 | t-Bu | 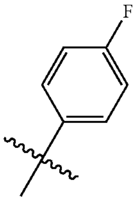 | Me | 5-Me | 3.93 | 382.2 | c |
| 193 | t-Bu | 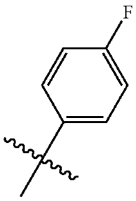 | Me | 5-OMe | 3.76 | 398.2 | c |
| 194 | t-Bu | 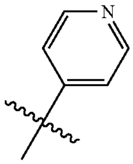 | Me | 5-Me | 2.76 | 365.2 | c |
| 195 | $CF_3$ | 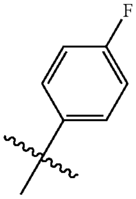 | 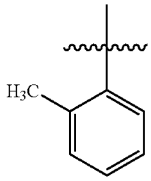 | 5-OMe | 3.77 | 486.2 | I |
| 196 | Et | 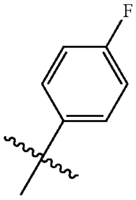 | 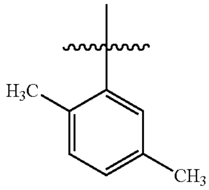 | 5-OMe | 3.68 | 460.2 | I |

TABLE 3a-continued
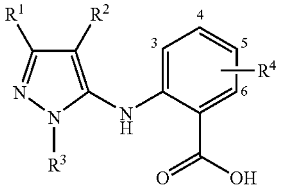
| Ex. No. | $R^1$ | $R^2$ | $R^3$ | $R^4$ | LC-MS RT (min) | LC-MS [M + H $^+$ | Note* |
|---|---|---|---|---|---|---|---|
| 197 | $CF_3$ | 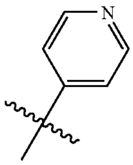 | 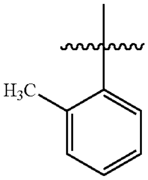 | 5-OMe | 2.68 | 469.2 | I |
| 198 | $CF_3$ | 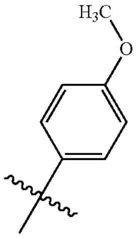 | 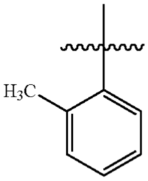 | 5-OMe | 3.7 | 498.2 | I |
| 199 | Et | 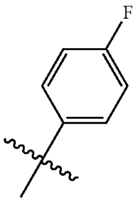 | 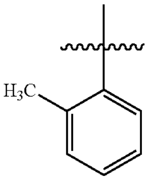 | 5-OMe | 3.56 | 446.2 | I |
| 200 | Et | Ph | 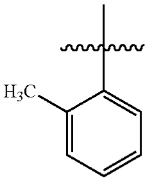 | 5-OMe | 3.52 | 428.2 | I |
| 201 | Et | Ph | 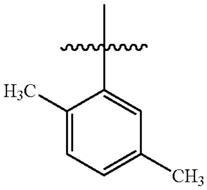 | 5-OMe | 3.64 | 442.2 | I |
| 202 | Et | 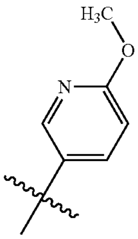 | 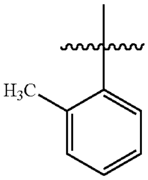 | 5-OMe | 3.27 | 459.2 | I |

TABLE 3a-continued
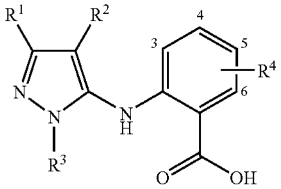
| Ex. No. | $R^1$ | $R^2$ | $R^3$ | $R^4$ | LC-MS RT (min) | LC-MS [M + H + | Note* |
|---|---|---|---|---|---|---|---|
| 203 | Et | 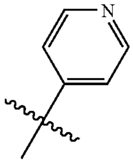 | 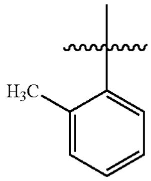 | 5-OMe | 2.38 | 429.2 | I |
| 204 | Et | 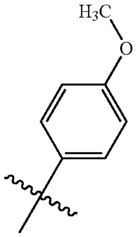 | 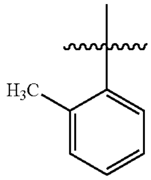 | 5-OMe | 3.48 | 458.2 | I |
| 205 | Et | 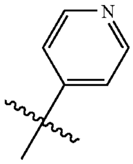 | 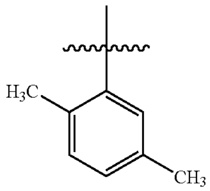 | 5-OMe | 2.5 | 443.2 | I |
| 206 | Et | 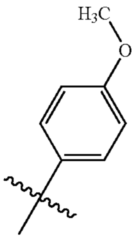 | 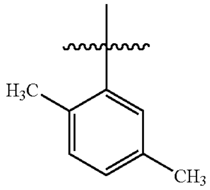 | 5-OMe | 3.59 | 472.2 | I |
| 207 | Me | 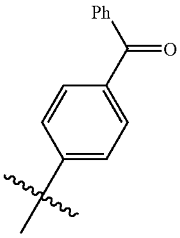 | 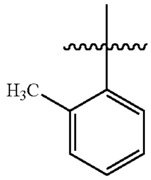 | 5-OMe | 3.59 | 518.2 | J |
| 208 | Me | 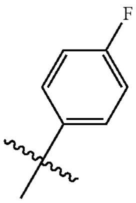 | 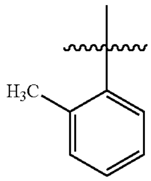 | 5-Me | 3.43 | 416.2 | J |

TABLE 3a-continued
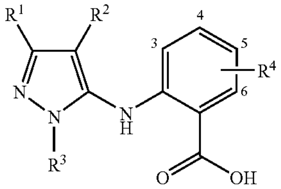
| Ex. No. | $R^1$ | $R^2$ | $R^3$ | $R^4$ | LC-MS RT (min) | LC-MS [M + H + | Note* |
|---|---|---|---|---|---|---|---|
| 209 | Me | 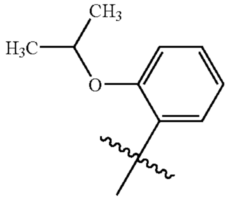 | 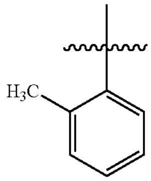 | 5-Me | 3.62 | 456.2 | J |
| 210 | Me | 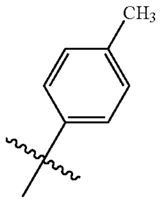 | 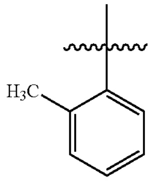 | 5-Me | 3.53 | 412.3 | J |
| 211 | Me | 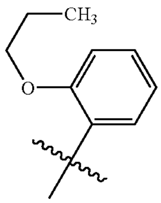 | 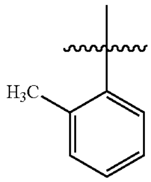 | 5-Me | 3.67 | 456.2 | J |
| 212 | Me | 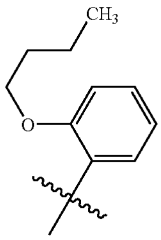 | 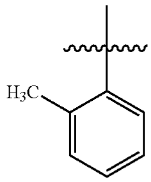 | 5-Me | 3.81 | 470.3 | J |
| 213 | Me | 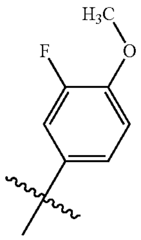 | 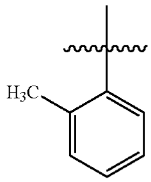 | 5-Me | 3.37 | 446.2 | J |
| 214 | Me | 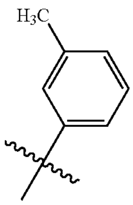 | 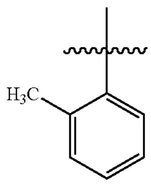 | 5-OMe | 3.33 | 428.2 | J |

TABLE 3a-continued
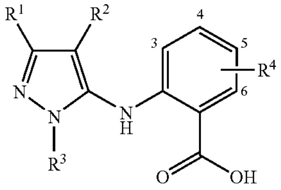
| Ex. No. | $R^1$ | $R^2$ | $R^3$ | $R^4$ | LC-MS RT (min) | LC-MS [M + H $^+$ | Note* |
|---|---|---|---|---|---|---|---|
| 215 | Me | 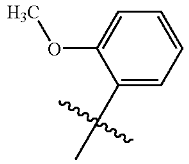 | 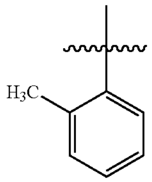 | 5-Me | 3.4 | 428.2 | J |
| 216 | Me | 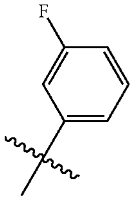 | 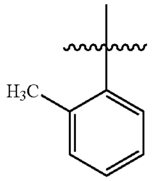 | 5-OMe | 3.27 | 432.2 | J |
| 217 | Me | 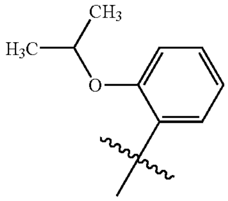 | 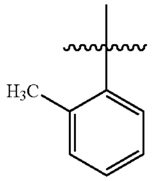 | 5-OMe | 3.37 | 472.3 | J |
| 218 | Me | 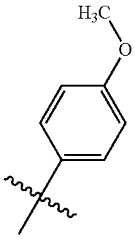 | 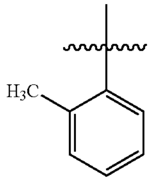 | 5-Me | 3.34 | 428.2 | J |
| 219 | Me | 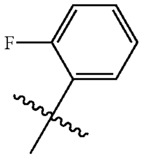 | 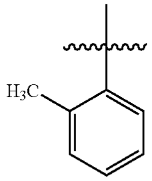 | 5-OMe | 3.22 | 432.2 | J |
| 220 | Me | 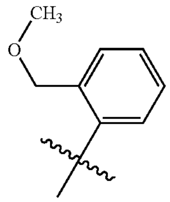 | 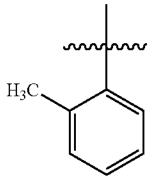 | 5-Me | 3.52 | 442.2 | J |

TABLE 3a-continued
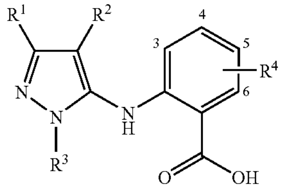
| Ex. No. | $R^1$ | $R^2$ | $R^3$ | $R^4$ | LC-MS RT (min) | LC-MS [M + H + | Note* |
|---|---|---|---|---|---|---|---|
| 221 | Me | 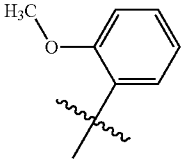 | 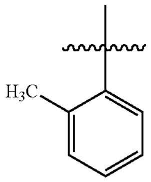 | 5-OMe | 3.26 | 444.2 | J |
| 222 | Me | 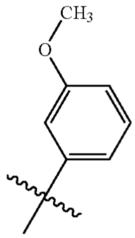 | 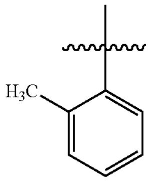 | 5-OMe | 3.2 | 444.2 | J |
| 223 | Me | 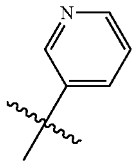 | 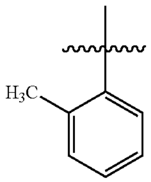 | 5-Me | 2.28 | 399.3 | J |
| 224 | Me | 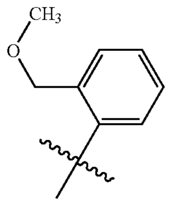 | 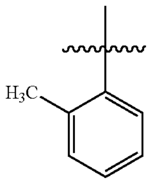 | 5-OMe | 3.25 | 458.3 | J |
| 225 | Me | 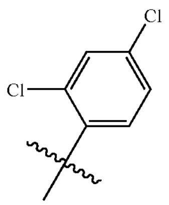 | 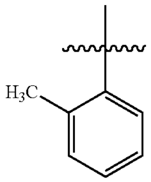 | 5-OMe | 4.02 | 482.2 | J |
| 226 | Me | 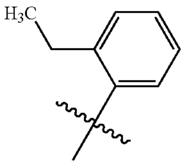 | 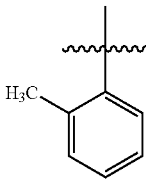 | 5-OMe | 3.87 | 442.3 | J |

TABLE 3a-continued
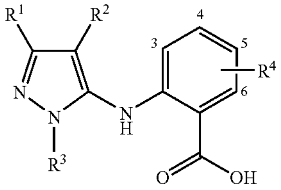
| Ex. No. | $R^1$ | $R^2$ | $R^3$ | $R^4$ | LC-MS RT (min) | LC-MS [M + H $^+$ | Note* |
|---|---|---|---|---|---|---|---|
| 227 | Me | 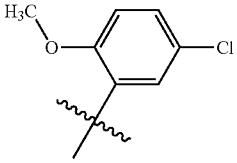 | 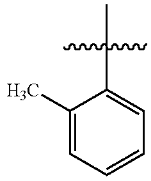 | 5-OMe | 3.81 | 478.2 | J |
| 228 | Me | 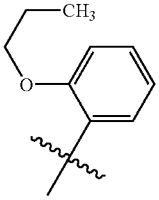 | 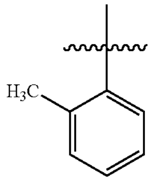 | 5-OMe | 3.89 | 472.3 | J |
| 229 | Me | Ph | 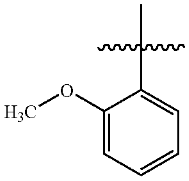 | 5-OMe | 3.1 | 430.2 | J |
| 230 | Me | 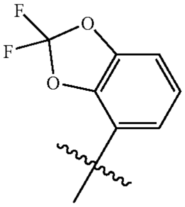 | 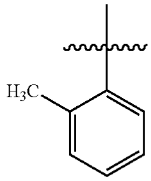 | 5-OMe | 3.91 | 494.2 | J |
| 231 | Me | 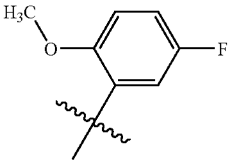 | 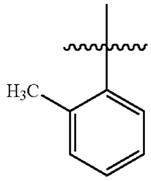 | 5-OMe | 3.67 | 462.2 | J |
| 232 | Me | 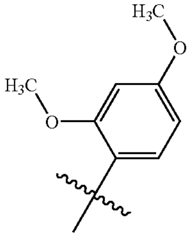 | 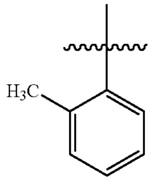 | 5-OMe | 3.59 | 474.2 | J |

TABLE 3a-continued

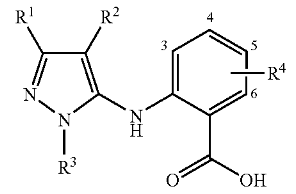

| Ex. No. | $R^1$ | $R^2$ | $R^3$ | $R^4$ | LC-MS RT (min) | LC-MS [M + H $^+$ | Note* |
|---|---|---|---|---|---|---|---|
| 233 | Me | 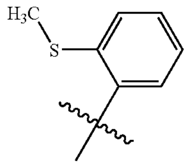 | 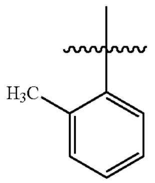 | 5-OMe | 3.74 | 460.2 | J |

*Note: Origin of the aminopyrazole used for the coupling reaction: c = commercial; I and J = using the methods of Reaction Schemes I and J as previously described TABLE 3b

| Ex. No. | IUPAC Name |
|---|---|
| 158 | 2-[(1,4-diphenyl-1H-pyrazol-5-yl)amino]-5-methoxybenzoic acid |
| 159 | 5-methoxy-2-{[4-(4-methoxyphenyl)-1-phenyl-1H-pyrazol-5-yl]amino}benzoic acid |
| 160 | 2-{[4-(2,4-difluorophenyl)-1-phenyl-1H-pyrazol-5-yl]amino}-5-methoxybenzoic acid |
| 161 | 2-{[4-(4-acetylphenyl)-1-phenyl-1H-pyrazol-5-yl]amino}-5-methoxybenzoic acid |
| 162 | 5-methoxy-2-[(1-phenyl-4-pyridin-4-yl-1H-pyrazol-5-yl)amino]benzoic acid trifluoroacetate |
| 163 | 5-methoxy-2-[(1-phenyl-4-pyridin-3-yl-1H-pyrazol-5-yl)amino]benzoic acid trifluoroacetate |
| 164 | 5-methoxy-2-{[3-methyl-1-(2-methylphenyl)-4-phenyl-1H-pyrazol-5-yl]amino}benzoic acid |
| 165 | 2-{[4-(4-fluorophenyl)-3-methyl-1-(2-methylphenyl)-1H-pyrazol-5-yl]amino}-5-methoxybenzoic acid |
| 166 | 5-methoxy-2-{[3-methyl-1-(2-methylphenyl)-4-(4-methylphenyl)-1H-pyrazol-5-yl]amino}benzoic acid |
| 167 | 5-methoxy-2-{[4-(4-methoxyphenyl)-3-methyl-1-(2-methylphenyl)-1H-pyrazol-5-yl]amino}benzoic acid |
| 168 | 2-{[4-(4-chlorophenyl)-3-methyl-1-(2-methylphenyl)-1H-pyrazol-5-yl]amino}-5-methoxybenzoic acid |
| 169 | 2-{[4-(2,4-difluorophenyl)-3-methyl-1-(2-methylphenyl)-1H-pyrazol-5-yl]amino}-5-methoxybenzoic acid |
| 170 | 2-{[4-(3-fluoro-4-methoxyphenyl)-3-methyl-1-(2-methylphenyl)-1H-pyrazol-5-yl]amino}-5-methoxybenzoic acid |
| 171 | 2-{[4-(4-acetylphenyl)-3-methyl-1-(2-methylphenyl)-1H-pyrazol-5-yl]amino}-5-methoxybenzoic acid |
| 172 | 5-methoxy-2-({3-methyl-1-(2-methylphenyl)-4-[4-(trifluoromethoxy)phenyl]-1H-pyrazol-5-yl}amino)benzoic acid |
| 173 | 5-methoxy-2-{[3-methyl-1-(2-methylphenyl)-4-pyridin-4-yl-1H-pyrazol-5-yl]amino}benzoic acid trifluoroacetate |
| 174 | 5-methoxy-2-{[3-methyl-1-(2-methylphenyl)-4-pyridin-3-yl-1H-pyrazol-5-yl]amino}benzoic acid trifluoroacetate |
| 175 | 5-methoxy-2-{[4-(6-methoxypyridin-3-yl)-3-methyl-1-(2-methylphenyl)-1H-pyrazol-5-yl]amino}benzoic acid |
| 176 | 5-fluoro-2-{[3-methyl-1-(2-methylphenyl)-4-pyridin-3-yl-1H-pyrazol-5-yl]amino}benzoic acid |
| 177 | 2-{[4-(3-chlorophenyl)-3-methyl-1-(2-methylphenyl)-1H-pyrazol-5-yl]amino}-5-methoxybenzoic acid |
| 178 | 2-{[4-(2-chlorophenyl)-3-methyl-1-(2-methylphenyl)-1H-pyrazol-5-yl]amino}-5-methoxybenzoic acid |
| 179 | 2-{[4-(4-fluoro-2-methylphenyl)-3-methyl-1-(2-methylphenyl)-1H-pyrazol-5-yl]amino}-5-methoxybenzoic acid |
| 180 | 2-{[4-(4-fluoro-3-methylphenyl)-3-methyl-1-(2-methylphenyl)-1H-pyrazol-5-yl]amino}-5-methoxybenzoic acid |
| 181 | 2-{[4-(4-ethoxyphenyl)-3-methyl-1-(2-methylphenyl)-1H-pyrazol-5-yl]amino}-5-methoxybenzoic acid |
| 182 | 2-{[3-tert-butyl-4-(4-chlorophenyl)-1-methyl-1H-pyrazol-5-yl]amino}-5- |

TABLE 3b-continued

| Ex. No. | IUPAC Name |
|---|---|
| | methoxybenzoic acid trifluoroacetate |
| 183 | 2-[(3-tert-butyl-1-methyl-4-phenyl-1H-pyrazol-5-yl)amino]-5-methoxybenzoic acid trifluoroacetate |
| 184 | 2-{[3-tert-butyl-1-methyl-4-(2-methylphenyl)-1H-pyrazol-5-yl]amino}-5-methoxybenzoic acid |
| 185 | 2-{[3-tert-butyl-4-(6-methoxypyridin-3-yl)-1-methyl-1H-pyrazol-5-yl]amino}-5-methoxybenzoic acid |
| 186 | 2-[(3-tert-butyl-1-methyl-4-pyridin-4-yl-1H-pyrazol-5-yl)amino]-5-methoxybenzoic acid trifluoroacetate |
| 187 | 2-[(3-tert-butyl-1-methyl-4-pyridin-3-yl-1H-pyrazol-5-yl)amino]-5-methoxybenzoic acid trifluoroacetate |
| 188 | 2-{[3-tert-butyl-4-(3-methoxyphenyl)-1-methyl-1H-pyrazol-5-yl]amino}-5-methoxybenzoic acid |
| 189 | 2-{[3-tert-butyl-4-(2-fluorophenyl)-1-methyl-1H-pyrazol-5-yl]amino}-5-methylbenzoic acid |
| 190 | 2-[(3-tert-butyl-1-methyl-4-phenyl-1H-pyrazol-5-yl)amino]-5-methylbenzoic acid |
| 191 | 2-{[3-tert-butyl-1-methyl-4-(4-methylphenyl)-1H-pyrazol-5-yl]amino}-5-methoxybenzoic acid |
| 192 | 2-{[3-tert-butyl-4-(4-fluorophenyl)-1-methyl-1H-pyrazol-5-yl]amino}-5-methylbenzoic acid |
| 193 | 2-{[3-tert-butyl-4-(4-fluorophenyl)-1-methyl-1H-pyrazol-5-yl]amino}-5-methoxybenzoic acid |
| 194 | 2-[(3-tert-butyl-1-methyl-4-pyridin-4-yl-1H-pyrazol-5-yl)amino]-5-methylbenzoic acid |
| 195 | 2-{[4-(4-fluorophenyl)-1-(2-methylphenyl)-3-(trifluoromethyl)-1H-pyrazol-5-yl]amino}-5-methoxybenzoic acid |
| 196 | 2-{[1-(2,5-dimethylphenyl)-3-ethyl-4-(4-fluorophenyl)-1H-pyrazol-5-yl]amino}-5-methoxybenzoic acid |
| 197 | 5-methoxy-2-{[1-(2-methylphenyl)-4-pyridin-4-yl-3-(trifluoromethyl)-1H-pyrazol-5-yl]amino}benzoic acid |
| 198 | 5-methoxy-2-{[4-(4-methoxyphenyl)-1-(2-methylphenyl)-3-(trifluoromethyl)-1H-pyrazol-5-yl]amino}benzoic acid |
| 199 | 2-{[3-ethyl-4-(4-fluorophenyl)-1-(2-methylphenyl)-1H-pyrazol-5-yl]amino}-5-methoxybenzoic acid |
| 200 | 2-{[3-ethyl-1-(2-methylphenyl)-4-phenyl-1H-pyrazol-5-yl]amino}-5-methoxybenzoic acid |
| 201 | 2-{[1-(2,5-dimethylphenyl)-3-ethyl-4-phenyl-1H-pyrazol-5-yl]amino}-5-methoxybenzoic acid |
| 202 | 2-{[3-ethyl-4-(6-methoxypyridin-3-yl)-1-(2-methylphenyl)-1H-pyrazol-5-yl]amino}-5-methoxybenzoic acid |
| 203 | 2-{[3-ethyl-1-(2-methylphenyl)-4-pyridin-4-yl-1H-pyrazol-5-yl]amino}-5-methoxybenzoic acid |
| 204 | 2-{[3-ethyl-4-(4-methoxyphenyl)-1-(2-methylphenyl)-1H-pyrazol-5-yl]amino}-5-methoxybenzoic acid |
| 205 | 2-{[1-(2,5-dimethylphenyl)-3-ethyl-4-pyridin-4-yl-1H-pyrazol-5-yl]amino}-5-methoxybenzoic acid |
| 206 | 2-{[1-(2,5-dimethylphenyl)-3-ethyl-4-(4-methoxyphenyl)-1H-pyrazol-5-yl]amino}-5-methoxybenzoic acid |
| 207 | 2-{[4-(4-benzoylphenyl)-3-methyl-1-(2-methylphenyl)-1H-pyrazol-5-yl]amino}-5-methoxybenzoic acid |
| 208 | 2-{[4-(4-fluorophenyl)-3-methyl-1-(2-methylphenyl)-1H-pyrazol-5-yl]amino}-5-methylbenzoic acid |
| 209 | 2-{[4-(2-isopropoxyphenyl)-3-methyl-1-(2-methylphenyl)-1H-pyrazol-5-yl]amino}-5-methylbenzoic acid |
| 210 | 5-methyl-2-{[3-methyl-1-(2-methylphenyl)-4-(4-methylphenyl)-1H-pyrazol-5-yl]amino}benzoic acid |
| 211 | 5-methyl-2-{[3-methyl-1-(2-methylphenyl)-4-(2-propoxyphenyl)-1H-pyrazol-5-yl]amino}benzoic acid |
| 212 | 2-{[4-(2-butoxyphenyl)-3-methyl-1-(2-methylphenyl)-1H-pyrazol-5-yl]amino}-5-methylbenzoic acid |
| 213 | 2-{[4-(3-fluoro-4-methoxyphenyl)-3-methyl-1-(2-methylphenyl)-1H-pyrazol-5-yl]amino}-5-methylbenzoic acid |
| 214 | 5-methoxy-2-{[3-methyl-1-(2-methylphenyl)-4-(3-methylphenyl)-1H-pyrazol-5-yl]amino}benzoic acid |
| 215 | 2-{[4-(2-methoxyphenyl)-3-methyl-1-(2-methylphenyl)-1H-pyrazol-5-yl]amino}-5-methylbenzoic acid |
| 216 | 2-{[4-(3-fluorophenyl)-3-methyl-1-(2-methylphenyl)-1H-pyrazol-5-yl]amino}-5-methoxybenzoic acid |
| 217 | 2-{[4-(2-isopropoxyphenyl)-3-methyl-1-(2-methylphenyl)-1H-pyrazol-5-yl]amino}-5-methoxybenzoic acid |
| 218 | 2-{[4-(4-methoxyphenyl)-3-methyl-1-(2-methylphenyl)-1H-pyrazol-5-yl]amino}-5-methylbenzoic acid |
| 219 | 2-{[4-(2-fluorophenyl)-3-methyl-1-(2-methylphenyl)-1H-pyrazol-5-yl]amino}-5-methoxybenzoic acid |
| 220 | 2-{[4-(2-ethoxyphenyl)-3-methyl-1-(2-methylphenyl)-1H-pyrazol-5-yl]amino}-5-methylbenzoic acid |

TABLE 3b-continued

| Ex. No. | IUPAC Name |
|---|---|
| 221 | 5-methoxy-2-{[4-(2-methoxyphenyl)-3-methyl-1-(2-methylphenyl)-1H-pyrazol-5-yl]amino}benzoic acid |
| 222 | 5-methoxy-2-{[4-(3-methoxyphenyl)-3-methyl-1-(2-methylphenyl)-1H-pyrazol-5-yl]amino}benzoic acid |
| 223 | 5-methyl-2-{[3-methyl-1-(2-methylphenyl)-4-pyridin-3-yl-1H-pyrazol-5-yl]amino}benzoic acid |
| 224 | 2-{[4-(2-ethoxyphenyl)-3-methyl-1-(2-methylphenyl)-1H-pyrazol-5-yl]amino}-5-methoxybenzoic acid |
| 225 | 2-{[4-(2,4-dichlorophenyl)-3-methyl-1-(2-methylphenyl)-1H-pyrazol-5-yl]amino}-5-methoxybenzoic acid |
| 226 | 2-{[4-(2-ethylphenyl)-3-methyl-1-(2-methylphenyl)-1H-pyrazol-5-yl]amino}-5-methoxybenzoic acid |
| 227 | 2-{[4-(5-chloro-2-methoxyphenyl)-3-methyl-1-(2-methylphenyl)-1H-pyrazol-5-yl]amino}-5-methoxybenzoic acid |
| 228 | 5-methoxy-2-{[3-methyl-1-(2-methylphenyl)-4-(2-propoxyphenyl)-1H-pyrazol-5-yl]amino}benzoic acid |
| 229 | 5-methoxy-2-{[1-(2-methoxyphenyl)-3-methyl-4-phenyl-1H-pyrazol-5-yl]amino}benzoic acid |
| 230 | 2-{[4-(2,2-difluoro-1,3-benzodioxol-4-yl)-3-methyl-1-(2-methylphenyl)-1H-pyrazol-5-yl]amino}-5-methoxybenzoic acid |
| 231 | 2-{[4-(5-fluoro-2-methoxyphenyl)-3-methyl-1-(2-methylphenyl)-1H-pyrazol-5-yl]amino}-5-methoxybenzoic acid |
| 232 | 2-{[4-(2,4-dimethoxyphenyl)-3-methyl-1-(2-methylphenyl)-1H-pyrazol-5-yl]amino}-5-methoxybenzoic acid |
| 233 | 5-methoxy-2-({3-methyl-1-(2-methylphenyl)-4-[2-(methylthio)phenyl]-1H-pyrazol-5-yl}amino)benzoic acid |

EXAMPLE 234

Preparation of methyl 5-bromo-2-{[(3-tert-butyl-1-(2-methylphenyl)-1H-pyrazol-5-yl]amino}benzoate

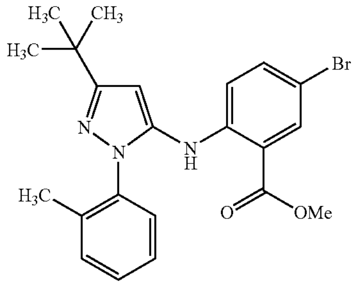

To a dried 25 mL flask was introduced 3-tert-butyl-1-(2-methylphenyl)-1H-pyrazol-5-amine (Intermediate C, 220 mg, 0.96 mmol), methyl 2,5-dibromobenzoate (235 mg, 0.80 mmol), $Pd_2(dba)_3$ (36.6 mg, 0.04 mmol), BINAP (49.8 mg, 0.08 mmol), and $Cs_2CO_3$ (365 mg, 1.12 mmol). The flask was degassed followed by addition of toluene (1 mL), and the mixture was then heated to 110° C. for 20 h. The mixture was cooled to rt, and diluted with ethyl acetate. The solid was filtered off, and the solvent was removed under reduced pressure. The residue was redissolved in methanol/THF (4:1, v/v) and filtered though a $C_8$-silica plug. HPLC purification using a gradient elution from 10% to 90% acetonitrile in water afforded 110 mg (31%) of the title compound. $^1$H NMR (300 MHz, $CD_2Cl_2$) δ 9.21 (s, 1H), 7.41 (d, 1H), 7.20-7.30 (m, 5H), 7.10 (d, 1H), 6.09 (s, 1H), 3.72 (s, 3H), 2.04 (s, 3H), 1.30 (s, 9H). ES-MS m/z 444.1 ($MH^+$); HPLC RT (min) 4.30.

EXAMPLE 235

Preparation of methyl 2-{[3-tert-butyl-1-(2-methylphenyl)-1H-pyrazol-5-yl]amino}-5-ethylbenzoate

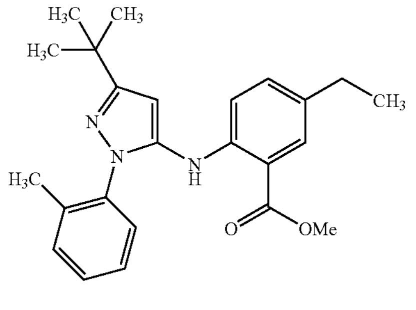

To a mixture of methyl 5-bromo-2-{[3-tert-butyl-1-(2-methylphenyl)-1H-pyrazol-5-yl]amino}benzoate (Example 234, 1.15 g, 4.13 mmol), ethylboronic acid (1.16 g, 15.7 mmol), and $Pd(dppf)Cl_2.CH_2Cl_2$ (114 mg, 0.16 mmol) was added toluene (20 mL) and dioxane (5 mL). The resulting solution was degassed under nitrogen for 30 min, followed by addition of sodium bicarbonate (2 M aq solution, 15 mL). The mixture was then heated to 85° C. for 16 h. The reaction mixture was allowed to cool to rt. The solvent was removed under reduced pressure, and the residue was purified by silica gel flash chromatography using 0 to 10% ethyl acetate in hexanes to afford 606 mg (61%) of the title compound. $^1$H NMR (300 MHz, $CD_2Cl_2$) δ 9.17 (s, 1H), 7.68 (s, 1H), 7.22-7.33 (m, 6H), 6.08 (s, 1H), 3.70 (s, 3H), 2.51 (q, 2H), 2.05 (s, 3H), 1.30 (s, 9H), 1.14 (t, 3H). ES-MS m/z 392.2 ($MH^+$); HPLC RT (min) 4.62.

EXAMPLE 236

Preparation of 2-{[3-tert-butyl-1-(2-methylphenyl)-1H-pyrazol-5-yl]amino}-5-ethylbenzoic acid

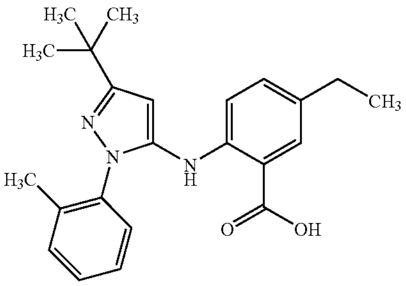

To a solution of methyl 2-{[3-tert-butyl-1-(2-methylphenyl)-1H-pyrazol-5-yl]amino}-5-ethylbenzoate (Example 235, 115 mg, 0.29 mmol) in a mixture of methanol (1 mL) and THF (1 mL) was added lithium hydroxide monohydrate (123 mg, 2.94 mmol) in water (2 mL), and the mixture was heated to 40° C. for 1 h. The reaction mixture was then cooled to rt, and the pH of the solution was adjusted to 5 using 0.5 N aq HCl. The solvent was removed under reduced pressure, and the residue was subjected to HPLC purification using gradient elution from 10% to 90% acetonitrile in water to afford 109.6 mg (99%) of the title compound. $^1$H NMR (300 $MH_z$, $CD_2Cl_2$) δ 9.28 (s, 1H), 7.76 (s, 1H), 7.26-7.37 (m, 6H), 6.15 (s, 1H), 2.60 (q, 2H), 2.08 (s, 3H), 1.37 (s, 9H), 1.23 (t, 3H). ES-MS m/z 378.3 ($MH^+$); HPLC RT (min) 3.64.

The following analogs were synthesized using the method described above for Example 236.

TABLE 4a

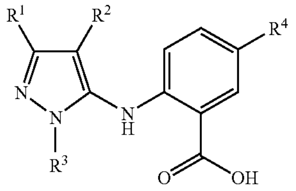

| Ex. No. | $R^1$ | $R^2$ | $R^3$ | $R^4$ | LC-MS RT (min) | LC-MS $[M + H]^+$ | Note* |
|---|---|---|---|---|---|---|---|
| 237 | Ph | H | 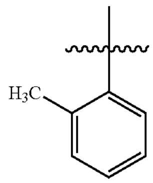 | Et | 3.77 | 397.8 | J |
| 238 | 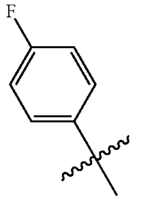 | H | 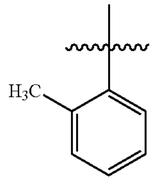 | Et | 4.28 | 416.2 | J |
| 239 | 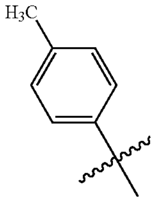 | H | 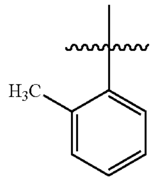 | Et | 3.92 | 411.8 | J |
| 240 | Ph | H | 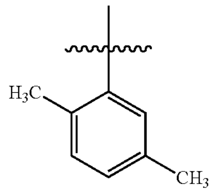 | Et | 3.9 | 411.8 | J |

TABLE 4a-continued

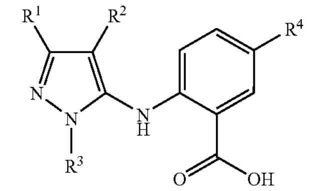

| Ex. No. | $R^1$ | $R^2$ | $R^3$ | $R^4$ | LC-MS RT (min) | LC-MS $[M + H]^+$ | Note* |
|---|---|---|---|---|---|---|---|
| 241 | 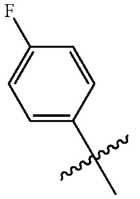 | H | 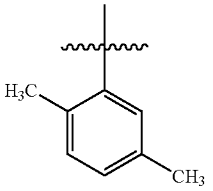 | Et | 3.96 | 429.8 | J |

*Note: Origin of the aminopyrazole used for the coupling reaction: c = commercial; J = using the method of Reaction Scheme J as previously described.

TABLE 4b

| Ex. No. | IUPAC Name |
|---|---|
| 237 | 5-ethyl-2-{[1-(2-methylphenyl)-3-phenyl-1H-pyrazol-5-yl]amino}benzoic acid |
| 238 | 5-ethyl-2-{[3-(4-fluorophenyl)-1-(2-methylphenyl)-1H-pyrazol-5-yl]amino}benzoic acid |
| 239 | 5-ethyl-2-{[1-(2-methylphenyl)-3-(4-methylphenyl)-1H-pyrazol-5-yl]amino}benzoic acid |
| 240 | 2-{[1-(2,5-dimethylphenyl)-3-phenyl-1H-pyrazol-5-yl]amino}-5-ethylbenzoic acid |
| 241 | 2-{[1-(2,5-dimethylphenyl)-3-(4-fluorophenyl)-1H-pyrazol-5-yl]amino}-5-ethylbenzoic acid |

EXAMPLE 242

Preparation of methyl 2-{[3-tert-butyl-1-(2-methylphenyl)-1H-pyrazol-5-yl]amino}-4-chlorobenzoate

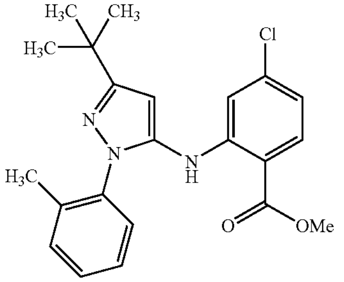

This compound was prepared using the procedure described in Example 234 and Intermediate C and methyl 2-bromo-4-chlorobenzoate as starting materials. $^1$H NMR (300 MHz, $CD_2Cl_2$) δ 9.33 (s, 1H), 7.84 (d, 1H), 7.20-7.30 (m, 4H), 7.15 (s, 1H), 6.68 (d, 1H), 6.13 (s, 1H), 3.72 (s, 3H), 2.06 (s, 3H), 1.31 (s, 9H). ES-MS m/z 398.3 $(MH)^+$; HPLC RT (min) 4.27.

EXAMPLE 243

Preparation of methyl 2-{[3-tert-butyl-1-(2-methylphenyl)-1H-pyrazol-5-yl]amino}-4-ethylbenzoate

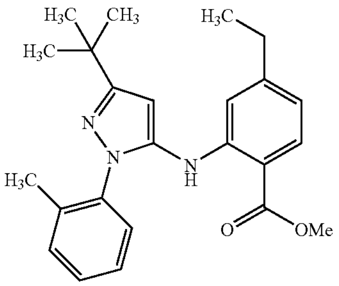

To a mixture of methyl 2-{[3-tert-butyl-1-(2-methylphenyl)-1H-pyrazol-5-yl]amino}-4-chlorobenzoate (Example 242, 50 mg, 0.13 mmol), ethylboronic acid (18.56 mg, 0.26 mmol), $Pd_2(dba)_3$ (5.8 mg, 0.006 mmol), tris(tert-butyl) phosphine (2.54 mg, 0.013 mmol), and potassium fluoride (14.6 mg, 0.25 mmol) was added dioxane (1 mL). The resulting solution was degassed under argon for 30 min and then heated to 110° C. for 16 h. The reaction mixture was then cooled to rt. The residue was diluted with ethyl acetate and filtered through a silica gel plug. The solvent was removed under reduced pressure, and the crude product was purified by HPLC purification using gradient elution from 30 to 100% acetonitrile in water to afford 39.8 mg (81%) of the title compound. $^1H$ NMR (300 MHz, $CD_2Cl_2$) δ 9.23 (s, 1H), 7.74 (d, 1H), 7.23-7.29 (m, 4H), 7.03 (s, 1H), 6.57 (d, 1H), 6.09 (s, 1H), 3.69 (s, 3H), 2.55 (q, 2H), 2.06 (s, 3H), 1.30 (s, 9H), 1.15 (t, 3H). ES-MS m/z 392.2 ($MH^+$); HPLC RT (min) 4.65.

EXAMPLE 244

Preparation of 2-{[3-tert-butyl-1-(2-methylphenyl)-1H-pyrazol-5-yl]amino}-4-ethylbenzoic acid

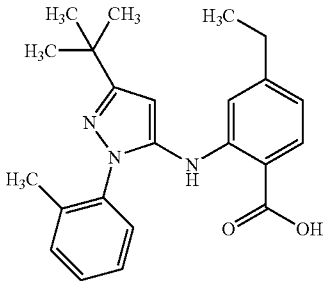

This compound was prepared from Example 243 using the hydrolysis procedure described in Example 236. $^1H$ NMR (300 $MH_z$, $CD_2Cl_2$) δ 9.45 (s, 1H), 7.81 (d, 1H), 7.20-7.35 (m, 4H), 7.09 (s, 1H), 6.68 (d, 1H), 6.13 (s, 1H), 2.61 (q, 2H), 2.03 (s, 3H), 1.33 (s, 9H), 1.19 (t, 3H). ES-MS m/z 378.2 ($MH^+$); HPLC RT (min) 4.12.

EXAMPLE 245

Preparation of 2-[(3-tert-butyl-1-methyl-1H-pyrazol-5-yl)amino]-4-pyrimidin-5-ylbenzoic acid

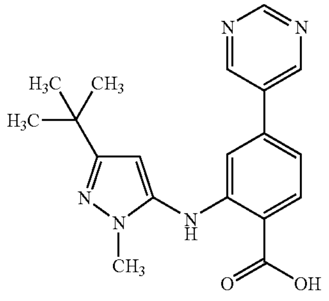

Using the method described for Example 244, the title compound was similarly prepared; ES-MS m/z 352.2 ($MH^+$); HPLC RT (min) 2.94.

EXAMPLE 246

Preparation of methyl 2-{[3-tert-butyl-1-(2-methylphenyl)-1H-pyrazol-5-yl]amino}-4-fluorobenzoate

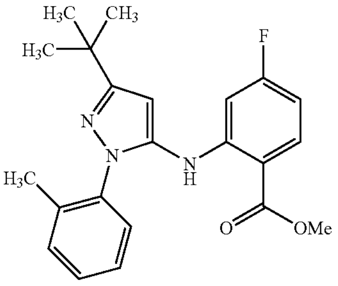

To a dried 25 mL flask was introduced 3-tert-butyl-1-(2-methylphenyl)-1H-pyrazol-5-amine (Intermediate C, 110 mg, 0.48 mmol), methyl 2-bromo-4-fluorobenzoate (93.1 mg, 0.40 mmol), $Pd_2(dba)_3$ (18.3 mg, 0.02 mmol), BINAP (24.9 mg, 0.04 mmol), and $Cs_2CO_3$ (182 mg, 0.56 mmol). The flask was degassed followed by the addition of toluene (1 mL), and the mixture was heated to 110° C. for 20 h. The mixture was then cooled to rt, and diluted with ethyl acetate. The solid was filtered off, and the solvent was removed under reduced pressure. The residue was redissolved in methanol/THF (4:1, v/v) and filtered through a $C_8$-silica plug. HPLC purification using gradient elution from 30% to 90% acetonitrile in water afforded 136.2 mg (89%) of the title compound. $^1H$ NMR (300 MHz, $CD_2Cl_2$) δ 9.42 (s, 1H), 7.85 (dd, 1H), 7.21-7.30 (m, 4H), 6.86 (dd, 1H), 6.44 (dt, 1H), 6.11 (s, 1H), 3.70 (s, 3H), 2.04 (s, 3H), 1.30 (s, 9H). ES-MS m/z 381.9 ($MH^+$); HPLC RT (min) 4.50.

EXAMPLE 247

Preparation of 2-{[3-tert-butyl-1-(2-methylphenyl)-1H-pyrazol-5-yl]amino}-4-(1H-imidazol-1-yl)benzoic acid

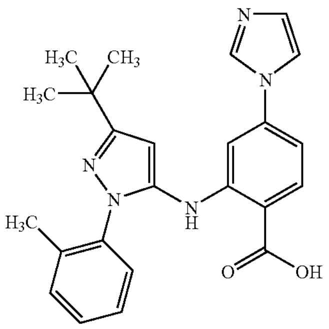

To a mixture of methyl 2-{[3-tert-butyl-1-(2-methylphenyl)-1H-pyrazol-5-yl]amino}-4-fluorobenzoate (Example 246, 50 mg, 0.13 mmol), imidazole (17.8 mg, 0.26 mmol), and potassium carbonate (90.6 mg, 0.66 mmol) was added DMF (1 mL). The mixture was then heated to 110° C. for 16 h. The reaction mixture was allowed to cool to rt. The solvent was removed under reduced pressure, and the crude was purified by HPLC purification using gradient elution from 10 to 80% acetonitrile in water to afford 13.8 mg (25%) of the title compound. $^1$H NMR (300 MHz, $CD_3OD$) δ 9.48 (t, 1H), 8.15 (d, 1H), 8.07 (t, 1H), 7.76 (t, 1H), 7.52 (d, 1H), 7.28-7.42 (m, 4H), 7.10 (dd, 1H), 6.48 (s, 1H), 2.06 (s, 3H), 1.35 (s, 9H). ES-MS m/z 416.2 ($MH^+$); HPLC RT (min) 2.21.

EXAMPLE 248

Preparation of 2-{[3-tert-butyl-1-(2-methylphenyl)-1H-pyrazol-5-yl]amino}-4-fluorobenzoic acid

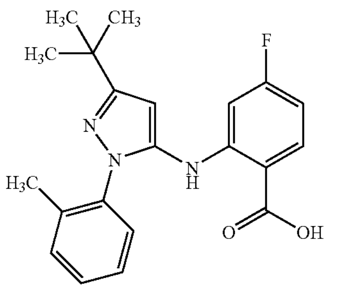

This compound was prepared from Example 246 using the hydrolysis procedure described in Example 236. $^1$H NMR (300 MHz, $CD_2Cl_2$) δ 9.49 (s, 1H), 7.89 (dd, 1H), 7.19-7.32 (m, 4H), 6.91 (dd, 1H), 6.47 (dt, 1H), 6.13 (s, 1H), 2.01 (s, 3H), 1.31 (s, 9H). ES-MS m/z 368.1 ($MH^+$); HPLC RT (min) 4.01.

EXAMPLE 249

Preparation of 2-{[3-tert-butyl-1-(2-methylphenyl)-1H-pyrazol-5-yl]amino}-4-(dimethylamino)benzoic acid

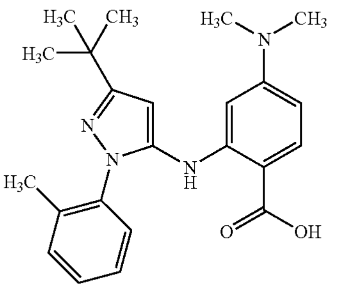

To a solution of 2-{[3-tert-butyl-1-(2-methylphenyl)-1H-pyrazol-5-yl]amino}-4-fluorobenzoic acid (Example 248, 35 mg, 0.09 mmol) in THF (1 mL) at −40° C. was added $LiNMe_2$ (0.19 mL, 1 M in hexanes) under nitrogen. The mixture was then stirred at this temperature for 30 min, and then gradually warmed to rt over a 4 h period. The pH of the solution was adjusted to pH 5, and the mixture was extracted with ethyl acetate. The organic layer was washed with brine, dried over $Na_2SO_4$, and concentrated under reduced pressure. The crude was purified by HPLC using gradient elution from 10 to 80% acetonitrile in water to afford 5.7 mg (15%) of the title compound. $^1$H NMR (300 MHz, $CD_2Cl_2$) δ 9.55 (s, 1H), 7.73 (d, 1H), 7.22-7.35 (m, 4H), 6.44 (d, 1H), 6.18 (dd, 1H), 6.15 (s, 1H), 3.00 (s, 6H), 2.04 (s, 3H), 1.32 (s, 9H). ES-MS m/z 393.2 ($MH^{30}$ ); HPLC RT (min) 2.84.

The examples shown in Table 5a were prepared by Buchwald-type coupling which was followed by a Suzuki reaction, bromination ($R^2$), a second Suzuki reaction, and hydrolysis. All reaction steps have been described in previous examples.

TABLE 5a

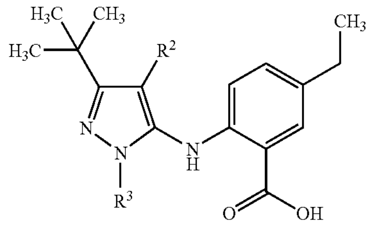

| Ex. No. | $R^2$ | LC-MS RT (min) | LC-MS $[M+H]^+$ |
|---|---|---|---|
| 250 | 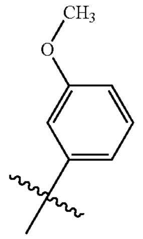 | 3.99 | 408.3 |
| 251 | 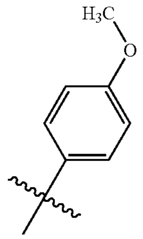 | 3.96 | 408.2 |
| 252 | Ph | 4.02 | 378.2 |
| 253 | 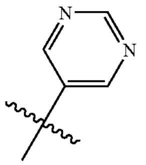 | 3.40 | 380.2 |
| 254 | 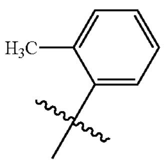 | 4.02 | 392.3 |
| 255 | 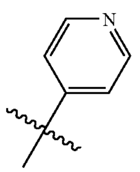 | 2.70 | 379.2 |

TABLE 5b

| Ex. No. | IUPAC Name |
|---|---|
| 250 | 2-{[3-tert-butyl-4-(3-methoxyphenyl)-1-methyl-1H-pyrazol-5-yl]amino}-5-ethylbenzoic acid |
| 251 | 2-{[3-tert-butyl-4-(4-methoxyphenyl)-1-methyl-1H-pyrazol-5-yl]amino}-5-ethylbenzoic acid |
| 252 | 2-[(3-tert-butyl-1-methyl-4-phenyl-1H-pyrazol-5-yl)amino]-5-ethylbenzoic acid |
| 253 | 2-[(3-tert-butyl-1-methyl-4-pyrimidin-5-yl-1H-pyrazol-5-yl)amino]-5-ethylbenzoic acid |
| 254 | 2-{[3-tert-butyl-1-methyl-4-(2-methylphenyl)-1H-pyrazol-5-yl]amino}-5-ethylbenzoic acid |
| 255 | 2-[(3-tert-butyl-1-methyl-4-pyridin-4-yl-1H-pyrazol-5-yl)amino]-5-ethylbenzoic acid trifluoroacetate |

The following examples represent carboxylic acid esters that were made using an Ullmann-type coupling reaction, followed by an esterification step.

EXAMPLE 256

Preparation of isopropyl 5-methoxy-2-[(1-phenyl-1H-pyrazol-5-yl)amino]benzoate

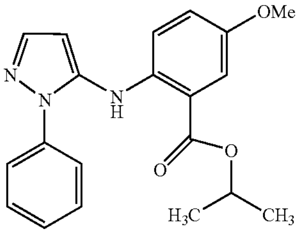

Step 1: Preparation of 5-methoxy-2-[(1-phenyl-1H-pyrazol-5-yl)amino] benzoic acid

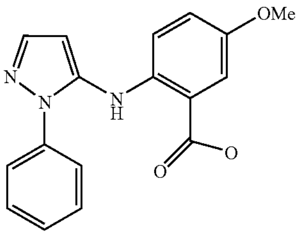

A mixture of 2-bromo-5-methoxy benzoic acid (1.31 g, 5.7 mmol), potassium carbonate (859 mg, 6.2 mmol), 5-amino-1-phenyl-pyrazole (900 mg, 5.7 mmol), and copper (II) acetate (21 mg, 0.11 mmol) in DMF (12 mL) was heated (150° C.) in a sealed tube for 16 h. After cooling, the reaction mixture was diluted with water (5 mL), and then acidified to pH 4 with acetic acid. The mixture was extracted with dichloromethane (3×10 mL), and then the combined organic extracts were washed with water (2×10 mL), dried over $Na_2SO_4$, filtered, and concentrated under reduced pressure. HPLC purification of the residue (YMC propack C18 column, 150×20 mm ID, 30%-80% acetonitrile in water gradient) afforded 5-methoxy-2-[(1-phenyl-1H-pyrazol-5-yl)amino] benzoic acid (450 mg, 26%) as a pale yellow solid: $^1$H NMR (300 MHz, DMSO-$d_6$) δ 13.33 (br s, 1H), 9.62 (br s, 1H), 7.64 (d, 1H), 7.34-7.58 (m, 6H), 7.00-7.11 (m, 2H), 6.30 (d, 1H), 3.69 (s, 3H); ES-MS m/z 310.1 (MH$^+$); HPLC RT (min) 2.74.

Step 2: Preparation of isopropyl 5-methoxy-2-[(1-phenyl-1H-pyrazol-5-yl)amino]benzoate

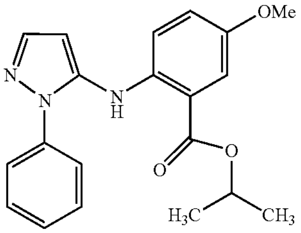

Cesium carbonate (105 mg, 0.19 mmol) and 2-iodopropane (18 mg, 0.11 mmol) were added to a solution of the intermediate 5-methoxy-2-[(1-phenyl-1H-pyrazol-5-yl) amino] benzoic acid (30 mg, 0.10 mmol) in DMF (4 mL). The mixture was stirred at rt for 16 h. The reaction was quenched with water (5 mL) and then extracted with dichloromethane (3×5 mL). The combined organic layers were washed with water (5 mL), dried over $Na_2SO_4$, filtered, and concentrated under reduced pressure. HPLC purification of the residue (YMC propack C18 column, 150×20 mm ID, 30%-80% acetonitrile in water gradient) afforded the desired product as a white solid (20 mg, 59%). $^1$H NMR (300 MHz, DMSO-$d_6$) δ 9.07 (s, 1H), 7.65 (d, 1H), 6.96-7.56 (m, 9H), 6.29 (dd, 1H), 5.06 (q, 1H), 3.69 (s, 3H), 1.24 (d, 6H); ES-MS m/z 352.1 (MH$^+$); HPLC RT (min) 3.53.

The following analogs were made using the method described above. The aminopyrazole used in the coupling reactions was commercially available.

TABLE 6a

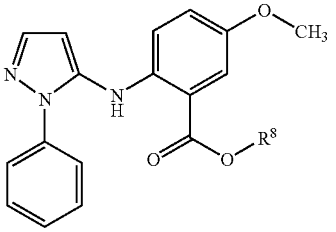

| Ex. No. | $R^8$ | LC-MS RT (min) | LC-MS [M + H]$^+$ |
|---|---|---|---|
| 257 | Bn | 3.68 | 400.1 |
| 258 | Me | 3.15 | 324.1 |
| 259 | Et | 3.31 | 338.3 |
| 260 | i-Bu | 3.75 | 366.2 |
| 261 | 4-MeOBn | 3.68 | 430.1 |

TABLE 6b

| Ex. No. | IUPAC Name |
|---|---|
| 257 | Benzyl 5-methoxy-2-[(1-phenyl-1H-pyrazol-5-yl)amino]benzoate |
| 258 | Methyl 5-methoxy-2-[(1-phenyl-1H-pyrazol-5-yl)amino]benzoate |
| 259 | Ethyl 5-methoxy-2-[(1-phenyl-1H-pyrazol-5-yl)amino]benzoate |

TABLE 6b-continued

| Ex. No. | IUPAC Name |
|---|---|
| 260 | Isobutyl 5-methoxy-2-[(1-phenyl-1H-pyrazol-5-yl)amino]benzoate |
| 261 | 4-Methoxybenzyl 5-methoxy-2-[(1-phenyl-1H-pyrazol-5-yl)amino]benzoate |

The following compounds were synthesized by using the procedure described in Example 108.

In Table 7a, the locant of the $R^4$ group(s) is defined as shown.

TABLE 7a

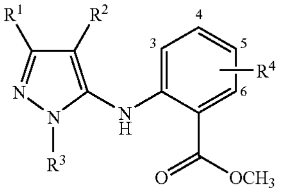

| Ex. No. | $R^1$ | $R^2$ | $R^3$ | $R^4$ | LC-MS RT (min) | LC-MS $[M + H]^+$ | Note* |
|---|---|---|---|---|---|---|---|
| 262 | H | H | 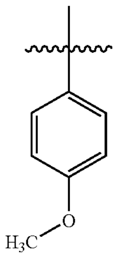 | 5-OMe | 3.57 | 354.1 | c |
| 263 | H | H | 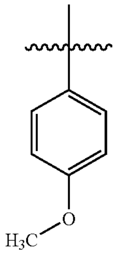 | — | 3.11 | 324.2 | c |
| 264 | Me | H | Ph | 5-OMe | 3.12 | 338.1 | c |
| 265 | t-Bu | H | $CH_2CF_3$ | 5-OMe | 3.85 | 386.1 | I |
| 266 | t-Bu | H | Me | 5-Me | 3.27 | 302.2 | c |
| 267 | t-Bu | H | Me | 3-Me | 2.66 | 302.2 | c |
| 268 | cyclopropyl | H | Ph | 5-OMe | 3.39 | 364.2 | c |
| 269 | Me | Me | Ph | 5-OMe | 3.32 | 352.2 | I |
| 270 | 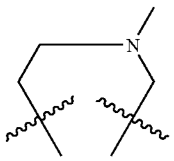 | | Ph | 5-OMe | 2.07 | 393.2 | I |
| 271 | 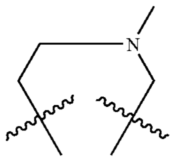 | | Ph | — | 2.05 | 363.2 | I |

TABLE 7a-continued

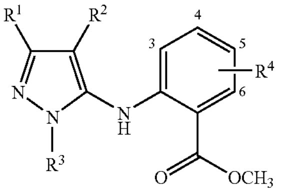

| Ex. No. | $R^1$ | $R^2$ | $R^3$ | $R^4$ | LC-MS RT (min) | LC-MS $[M + H]^+$ | Note* |
|---|---|---|---|---|---|---|---|
| 272 | 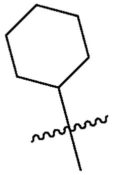 | H | 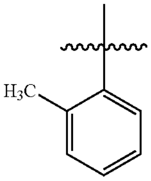 | 5-OMe | 3.95 | 420.4 | I |
| 273 | 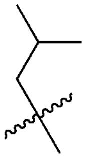 | H | 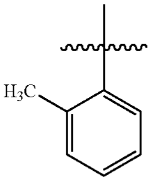 | 5-OMe | 3.77 | 394.2 | I |
| 274 | t-Bu | H | 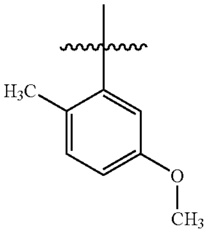 | 5-OMe | 3.78 | 424.3 | I |
| 275 | t-Bu | H | 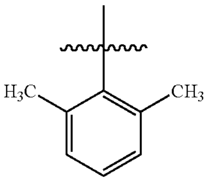 | 5-OMe | 4.24 | 408.3 | I |

*Note: Origin of the aminopyrazole used for the coupling reaction: c = commercial; I = using the methods of Reaction Scheme I as previously described.

TABLE 7b

| Ex. No. | IUPAC Name |
|---|---|
| 262 | Methyl 5-methoxy-2-{[1-(4-methoxyphenyl)-1H-pyrazol-5-yl]amino}benzoate |
| 263 | Methyl 2-{[1-(4-methoxyphenyl)-1H-pyrazol-5-yl]amino}benzoate |
| 264 | Methyl 5-methoxy-2-[(3-methyl-1-phenyl-1H-pyrazol-5-yl)amino]benzoate |
| 265 | Methyl 2-{[3-tert-butyl-1-(2,2,2-trifluoroethyl)-1H-pyrazol-5-yl]amino}-5-methoxybenzoate |
| 266 | Methyl 2-[(3-tert-butyl-1-methyl-1H-pyrazol-5-yl)amino]-5-methylbenzoate |
| 267 | Methyl 2-[(3-tert-butyl-1-methyl-1H-pyrazol-5-yl)amino]-3-methylbenzoate |
| 268 | Methyl 2-[(3-cyclopropyl-1-phenyl-1H-pyrazol-5-yl)amino]-5-methoxybenzoate |
| 269 | Methyl 2-[(3,4-dimethyl-1-phenyl-1H-pyrazol-5-yl)amino]-5-methoxybenzoate |
| 270 | Methyl 5-methoxy-2-[(5-methyl-2-phenyl-4,5,6,7-tetrahydro-2H-pyrazolo[4,3-c]pyridin-3-yl)amino]benzoate |
| 271 | Methyl 2-[(5-methyl-2-phenyl-4,5,6,7-tetrahydro-2H-pyrazolo[4,3-c]pyridin-3-yl)amino]benzoate |

TABLE 7b-continued

| Ex. No. | IUPAC Name |
|---|---|
| 272 | Methyl 2-{[3-cyclohexyl-1-(2-methylphenyl)-1H-pyrazol-5-yl]amino}-5-methoxybenzoate |
| 273 | Methyl 2-{[3-isobutyl-1-(2-methylphenyl)-1H-pyrazol-5-yl]amino}-5-methoxybenzoate |
| 274 | Methyl 2-{[3-tert-butyl-1-(5-methoxy-2-methylphenyl)-1H-pyrazol-5-yl]amino}-5-methoxybenzoate |
| 275 | Methyl 2-{[3-tert-butyl-1-(2,6-dimethylphenyl)-1H-pyrazol-5-yl]amino}-5-methoxybenzoate |

The following analogs were synthesized from a Cl precursor synthesized in a similar fashion as Example 242 using a similar procedure as described in Example 243. The boronic acids used were commercially available.

TABLE 8a

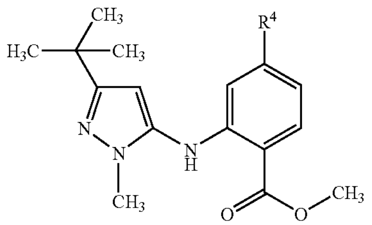

| Ex. No. | $R^4$ | LC-MS RT (min) | LC-MS $[M + H]^+$ |
|---|---|---|---|
| 276 | 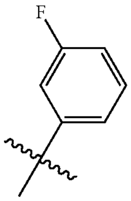 | 3.78 | 382.2 |
| 277 | 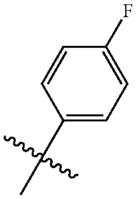 | 3.77 | 382.1 |
| 278 | 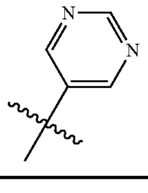 | 2.83 | 386.2 |

TABLE 8b

| Ex. No. | IUPAC Name |
|---|---|
| 276 | Methyl 3-[(3-tert-butyl-1-methyl-1H-pyrazol-5-yl)amino]-3'-fluorobiphenyl-4-carboxylate |
| 277 | Methyl 3-[(3-tert-butyl-1-methyl-1H-pyrazol-5-yl)amino]-4'-fluorobiphenyl-4-carboxylate |
| 278 | Methyl 2-[(3-tert-butyl-1-methyl-1H-pyrazol-5-yl)amino]-4-pyrimidin-5-ylbenzoate |

The following examples represent carboxylic acid amides that were made using an Ullmann-type coupling reaction.

EXAMPLE 279

Preparation of 2-{[3-methyl-1-(2-methylphenyl)-1H-pyrazol-5-yl]amino}benzamide

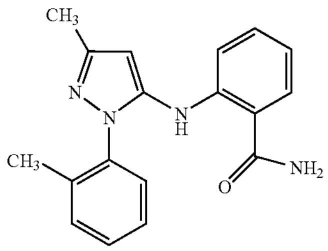

A mixture of 3-methyl-1-(2-methylphenyl)-1H-pyrazol-5-amine (Intermediate F, 1.00 g, 5.3 mmol), 2-bromobenzamide (1.07 g, 5.3 mmol), potassium carbonate (0.89 g, 6.4 mmol), and copper (II) acetate (39 mg, 0.2 mmol) in DMF (20 mL) was heated (150° C.) in a sealed tube for 18 h. After cooling, the solution was adjusted to pH=4 using glacial acetic acid. The reaction mixture was extracted with dichloromethane (3×20 mL), and then the combined organic extracts were washed with brine, dried over anhydrous magnesium sulfate, filtered, and concentrated in vacuo. Flash chromatography of the residue over silica gel using 33-50% ethyl acetate/hexane afforded a yellow solid that was washed with diethyl ether to give 2-{[3-methyl-1-(2-methylphenyl)-1H-pyrazol-5-yl]amino}benzamide (350 mg, 21%) as a white solid. $^1H$ NMR (300 MHz, DMSO-$d_6$) δ 10.48 (s, 1H), 8.01 (s, 1H), 7.67 (dd, 1H), 7.32 (m, 7H), 6.77 (ddd, 1H), 6.08 (s, 1H), 2.19 (s, 3H), 2.00 (s, 3H); ES-MS m/z 307.1 ($MH^+$); HPLC RT (min) 2.41.

The following analogs were made using the method described above for Example 279.

In Table 9a, the locant of the $R^4$ group(s) is defined as shown.

TABLE 9a

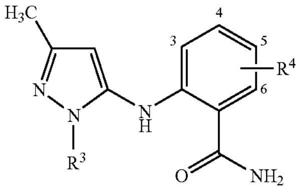

| Ex. No. | $R^3$ | $R^4$ | LC-MS RT (min) | LC-MS $[M + H]^+$ | Note* |
|---|---|---|---|---|---|
| 280 | 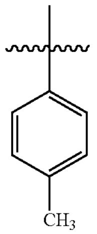 | — | 2.54 | 307.1 | c |
| 281 | 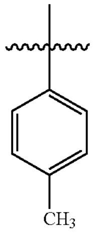 | 5-OMe | 2.54 | 337.1 | c |
| 282 | 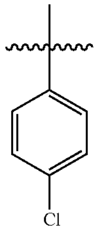 | — | 2.8 | 327.1 | c |
| 283 | 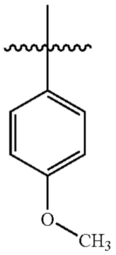 | — | 2.41 | 323.1 | J |

*Note: Origin of the aminopyrazole used for the coupling reaction: c = commercial; J = using the method of Reaction Scheme J as previously described.

TABLE 9b

| Ex. No. | IUPAC Name |
|---|---|
| 280 | 2-{[3-methyl-1-(4-methylphenyl)-1H-pyrazol-5-yl]amino}benzamide |
| 281 | 5-methoxy-2-{[3-methyl-1-(4-methylphenyl)-1H-pyrazol-5-yl]amino}benzamide |
| 282 | 2-{[1-(4-chlorophenyl)-3-methyl-1H-pyrazol-5-yl]amino}benzamide |
| 283 | 2-{[1-(4-methoxyphenyl)-3-methyl-1H-pyrazol-5-yl]amino}benzamide |

The following examples represent carboxylic acid $1^0$ amides that were made from their corresponding carboxylic acids derived from Ullmann-type coupling.

EXAMPLE 284

Preparation of 2-{[3-tert-butyl-1-(2-methylphenyl)-1H-pyrazol-5-yl]amino}-5-methoxybenzamide

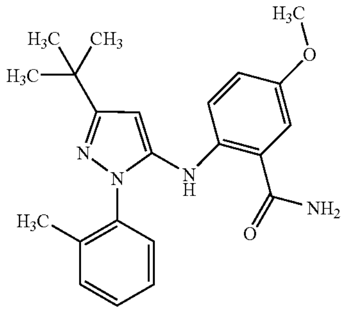

To a solution of 2-{[3-tert-butyl-1-(2-methylphenyl)-1H-pyrazol-5-yl]amino}-5-methoxybenzoic acid (Example 4) (130 mg, 0.34 mmol) in DMF (5 mL) were added ammonium chloride (22 mg, 0.41 mmol), 1-(3-dimethylaminopropyl)-3-ethylcarbodiimide hydrochloride (79 mg, 0.41 mmol), HOBT hydrate (56 mg, 0.41 mmol), and triethylamine (0.17 mL, 1.20 mmol). The reaction mixture was stirred for 16 h and then concentrated under reduced pressure. The residue was purified by HPLC (45-90% acetonitrile in water) to afford the product (63 mg, 49%) as a white solid. $^1H$ NMR (400 MHz, DMSO-$d_6$) δ 1.26 (s, 9H), 1.97 (s, 3H), 3.71 (s, 3H), 6.03 (s, 1H), 7.04 (dd, 1H), 7.24-7.37 (m, 6H), 7.44 (s, 1H), 8.05 (s, 1H), 10.01 (s, 1H); ES-MS m/z 379.3 ($MH^+$); HPLC RT (min) 2.83.

The following analogs appearing in Tables 10a, 10b, 11a, and 11b were synthesized using the sequence described above for Example 284.

In Table 10a, the locant of the $R^4$ group(s) is defined as shown.

TABLE 10a
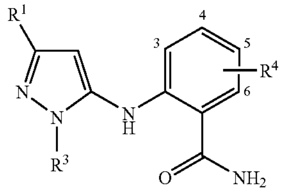
| Ex. No. | $R^1$ | $R^3$ | $R^4$ | LC-MS RT (min) | LC-MS $[M + H]^+$ | Note* |
|---|---|---|---|---|---|---|
| 285 | Me | 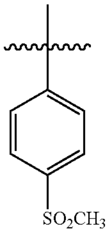 | 5-OMe | 2.39 | 401.1 | J |
| 286 | Me | 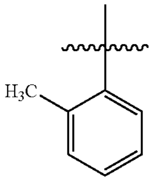 | 5-OMe | 2.31 | 337.2 | J |
| 287 | t-Bu | i-Pr | 4,5-di-OMe | 2.63 | 361.2 | I |
| 288 | t-Bu | 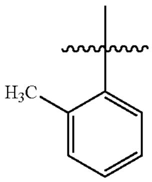 | 4,5-di-OMe | 2.78 | 409.2 | I |
| 289 | t-Bu | 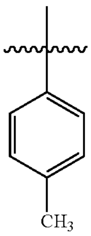 | — | 3.17 | 349.2 | I |
| 290 | t-Bu | 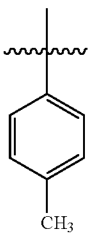 | 5-OMe | 3.08 | 379.3 | I |
| 291 | t-Bu | 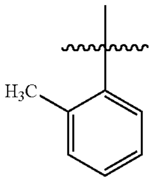 | — | 2.92 | 349.2 | I |

TABLE 10a-continued
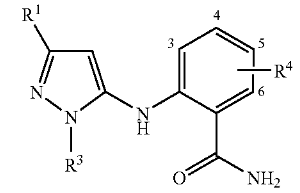
| Ex. No. | $R^1$ | $R^3$ | $R^4$ | LC-MS RT (min) | LC-MS $[M + H]^+$ | Note* |
|---|---|---|---|---|---|---|
| 292 | t-Bu | 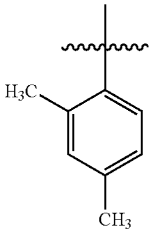 | — | 3.22 | 363.2 | I |
| 293 | t-Bu | 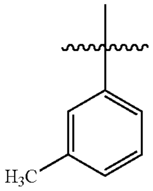 | — | 3.38 | 349.2 | I |
| 294 | t-Bu | 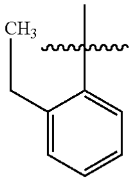 | 4,5-di-OMe | 3.12 | 423.2 | I |
| 295 | t-Bu | 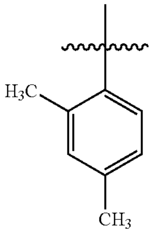 | 5-OMe | 3.10 | 393.2 | I |
| 296 | t-Bu | 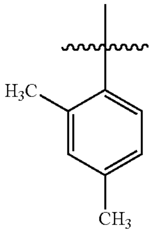 | 4,5-di-OMe | 3.06 | 423.2 | I |
| 297 | Ph | Ph | 5-OMe | 3.2 | 385.2 | c |

TABLE 10a-continued

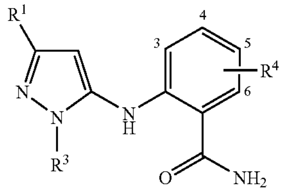

| Ex. No. | $R^1$ | $R^3$ | $R^4$ | LC-MS RT (min) | LC-MS $[M + H]^+$ | Note* |
|---|---|---|---|---|---|---|
| 298 | Ph | 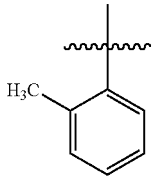 | — | 3.18 | 369.2 | J |
| 299 | 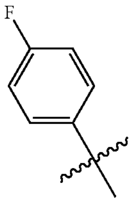 | 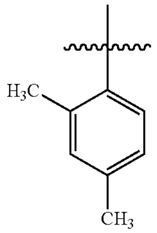 | — | 3.56 | 401.2 | J |
| 300 | t-Bu | 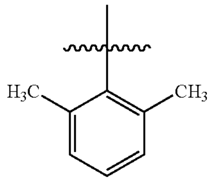 | — | 3.12 | 363.2 | I |

*Note: Origin of the aminopyrazole used for the coupling reaction: c = commercial; I, J = using the methods of Reaction Schemes I or J as previously described TABLE 10b

| Ex. No. | IUPAC Name |
|---|---|
| 285 | 5-methoxy-2-({3-methyl-1-[4-(methylsulfonyl)phenyl]-1H-pyrazol-5-yl}amino)benzamide |
| 286 | 5-methoxy-2-{[3-methyl-1-(2-methylphenyl)-1H-pyrazol-5-yl]amino}benzamide |
| 287 | 2-[(3-tert-butyl-1-isopropyl-1H-pyrazol-5-yl)amino]-4,5-dimethoxybenzamide |
| 288 | 2-{[3-tert-butyl-1-(2-methylphenyl)-1H-pyrazol-5-yl]amino}-4,5-dimethoxybenzamide |
| 289 | 2-{[3-tert-butyl-1-(4-methylphenyl)-1H-pyrazol-5-yl]amino}benzamide |
| 290 | 2-{[3-tert-butyl-1-(4-methylphenyl)-1H-pyrazol-5-yl]amino}-5-methoxybenzamide |
| 291 | 2-{[3-tert-butyl-1-(2-methylphenyl)-1H-pyrazol-5-yl]amino}benzamide |
| 292 | 2-{[3-tert-butyl-1-(2,4-dimethylphenyl)-1H-pyrazol-5-yl]amino}benzamide |
| 293 | 2-{[3-tert-butyl-1-(3-methylphenyl)-1H-pyrazol-5-yl]amino}benzamide |
| 294 | 2-{[3-tert-butyl-1-(2-ethylphenyl)-1H-pyrazol-5-yl]amino}-4,5-dimethoxybenzamide |
| 295 | 2-{[3-tert-butyl-1-(2,4-dimethylphenyl)-1H-pyrazol-5-yl]amino}-5-methoxybenzamide |
| 296 | 2-{[3-tert-butyl-1-(2,4-dimethylphenyl)-1H-pyrazol-5-yl]amino}-4,5-dimethoxybenzamide |
| 297 | 2-[(1,3-diphenyl-1H-pyrazol-5-yl)amino]-5-methoxybenzamide |
| 298 | 2-{[1-(2-methylphenyl)-3-phenyl-1H-pyrazol-5-yl]amino}benzamide |
| 299 | 2-{[1-(2,4-dimethylphenyl)-3-(4-fluorophenyl)-1H-pyrazol-5-yl]amino}benzamide |
| 300 | 2-{[3-tert-butyl-1-(2,6-dimethylphenyl)-1H-pyrazol-5-yl]amino}benzamide |

The following examples represent primary amides that are derived from a sequence consisting of Buchwald-type coupling, hydrolysis, and amide formation.

In Table 11a, the locant of the $R^4$ group(s) is defined as shown.

TABLE 11a
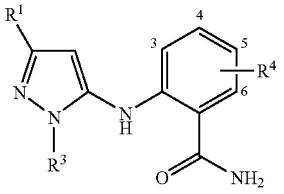
| Ex. No. | $R^1$ | $R^3$ | $R^4$ | LC-MS RT (min) | LC-MS $[M + H]^+$ | Note* |
|---|---|---|---|---|---|---|
| 301 | H | 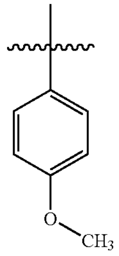 | 5-OMe | 2.58 | 339.1 | c |
| 302 | t-Bu | Bn | — | 3.02 | 349.2 | I |
| 303 | t-Bu | 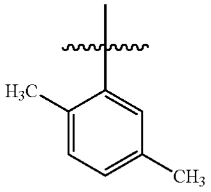 | 5-OMe | 3.02 | 393.2 | I |
| 304 | t-Bu | Ph | — | 3.23 | 335.1 | I |
| 305 | t-Bu | Ph | 5-OMe | 2.98 | 365.2 | I |
| 306 | t-Bu | 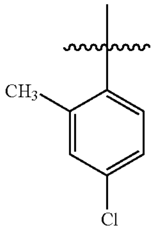 | — | 3.35 | 383.2 | I |
| 307 | $CF_3$ | 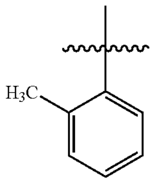 | — | 3.14 | 361.1 | I |
*Note: Origin of the aminopyrazole used for the coupling reaction: c = commercial; I = using the method of Reaction Scheme I as previously described.

TABLE 11b

| Ex. No. | IUPAC Name |
| --- | --- |
| 301 | 5-methoxy-2-{[1-(4-methoxyphenyl)-1H-pyrazol-5-yl]amino}benzamide |
| 302 | 2-[(1-benzyl-3-tert-butyl-1H-pyrazol-5-yl)amino]benzamide |
| 303 | 2-{[3-tert-butyl-1-(2,5-dimethylphenyl)-1H-pyrazol-5-yl]amino}-5-methoxybenzamide |
| 304 | 2-[(3-tert-butyl-1-phenyl-1H-pyrazol-5-yl)amino]benzamide |
| 305 | 2-[(3-tert-butyl-1-phenyl-1H-pyrazol-5-yl)amino]-5-methoxybenzamide |
| 306 | 2-{[3-tert-butyl-1-(4-chloro-2-methylphenyl)-1H-pyrazol-5-yl]amino}benzamide |
| 307 | 2-{[1-(2-methylphenyl)-3-(trifluoromethyl)-1H-pyrazol-5-yl]amino}benzamide |

The following examples represent secondary and tertiary amides derived from a sequence consisting of Ullmann-type coupling and subsequent amide formation.

EXAMPLE 308

Preparation of N-benzyl-5-methoxy-2-[(1-phenyl-1H-pyrazol-5-yl)amino]benzamide

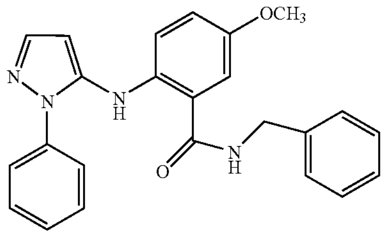

A mixture of 5-methoxy-2-[(1-phenyl-1H-pyrazol-5-yl)amino]benzoic acid (made by Ullmann reaction as described in Example 1, 42.0 mg, 0.14 mmol), benzylamine hydrochloride (23.4 mg, 0.16 mmol), EDCI (31.2 mg, 0.16 mmol), HOBT (22.0 mg, 0.16 mmol), and triethylamine (0.066 mL, 0.48 mmol) in DMF (3 mL) was stirred at rt for 16 h. The reaction was quenched with water (20 mL) and extracted with ethyl acetate (10 mL). The organic layer was washed with brine, dried over $Na_2SO_4$, filtered, and concentrated under reduced pressure. Flash chromatography of the residue over silica gel, using 20% ethyl acetate/hexane, gave the title compound (16.1 mg, 30%) as a white solid. $^1H$ NMR (300 MHz, DMSO-$d_6$) δ 9.72 (s, 1H), 9.14 (t, 1H), 7.57 (d, 1H), 7.38-7.51 (m, 4H), 7.16-7.36 (m, 7H), 6.96-7.06 (m, 2H), 6.15 (s, 1H), 4.37 (d, 2H), 3.70 (s, 3H); ES-MS m/z 399.1 ($MH^+$), HPLC RT (min) 3.72.

The following compounds appearing in Tables 12a, 12b, 13a, and 13b were prepared using the method described above for Example 308.

In Table 12a, the locant of the $R^4$ group(s) is defined as shown.

TABLE 12a

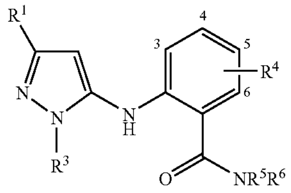

| Ex. No. | $R^1$ | $R^3$ | $R^4$ | $R^5$ | $R^6$ | LC-MS RT (min) | LC-MS $[M + H]^+$ | Note* |
| --- | --- | --- | --- | --- | --- | --- | --- | --- |
| 309 | H | Ph | 5-OMe | Et | Et | 3.24 | 365.1 | c |
| 310 | H | Ph | 5-SMe | Me | H | 2.82 | 339.1 | c |
| 311 | H | Ph | 5-SMe | Et | H | 3.02 | 353.1 | c |
| 312 | H | Ph | 5-SMe | i-Pr | H | 3.19 | 367.1 | c |
| 313 | H | Ph | 5-SMe | Et | Et | 3.00 | 381.1 | c |
| 314 | H | Ph | 5-SMe | 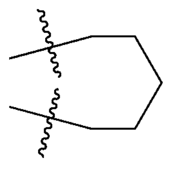 | | 3.54 | 393.1 | c |

TABLE 12a-continued
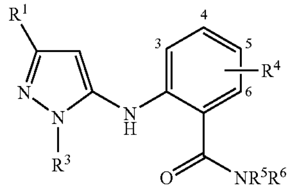
| Ex. No. | $R^1$ | $R^3$ | $R^4$ | $R^5$ | $R^6$ | LC-MS RT (min) | LC-MS $[M + H]^+$ | Note* |
|---|---|---|---|---|---|---|---|---|
| 315 | H | Ph | 5-SMe | 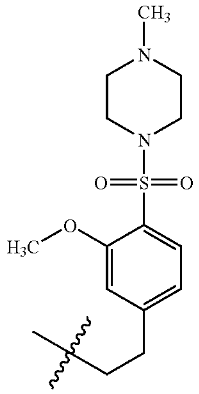 | H | 2.89 | 621.2 | c |
| 316 | Me | 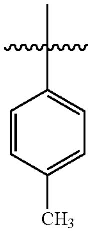 | — | i-Pr | H | 3.01 | 349.3 | c |
| 317 | Me | 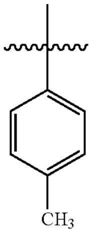 | — | Ph | H | 3.32 | 383.2 | c |
| 318 | Me | 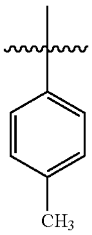 | 5-OMe | Me | H | 2.64 | 351.1 | c |

TABLE 12a-continued
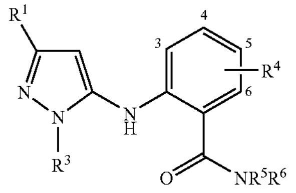
| Ex. No. | $R^1$ | $R^3$ | $R^4$ | $R^5$ | $R^6$ | LC-MS RT (min) | LC-MS $[M + H]^+$ | Note* |
|---|---|---|---|---|---|---|---|---|
| 319 | Me | 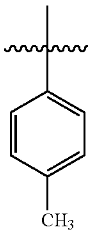 | 5-OMe | Et | H | 2.80 | 365.1 | c |
| 320 | Me | 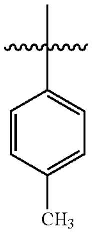 | 5-OMe | i-Pr | H | 2.95 | 379.1 | c |
| 321 | Me | 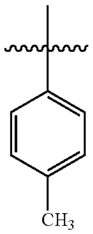 | 5-OMe | Ph | H | 3.26 | 413.1 | c |
| 322 | Me | 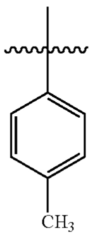 | — | 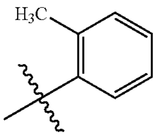 | H | 3.31 | 397.1 | c |
| 323 | Me | 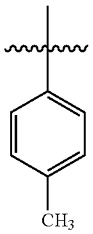 | — | 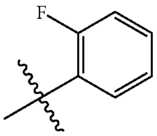 | H | 3.38 | 401.2 | c |

TABLE 12a-continued

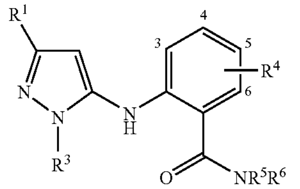

| Ex. No. | $R^1$ | $R^3$ | $R^4$ | $R^5$ | $R^6$ | LC-MS RT (min) | LC-MS $[M + H]^+$ | Note* |
|---|---|---|---|---|---|---|---|---|
| 324 | Me | 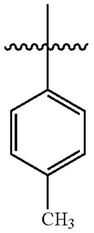 | — | 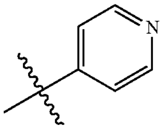 | H | 2.68 | 384.1 | c |
| 325 | Me | 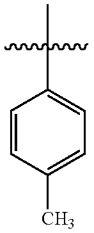 | — | 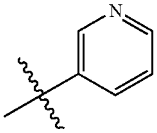 | H | 2.78 | 384.1 | c |

*Origin of the aminopyrazole used for the coupling reaction: c = commercial

TABLE 12b

| Ex. No. | IUPAC Name |
|---|---|
| 309 | N,N-diethyl-5-methoxy-2-[(1-phenyl-1H-pyrazol-5-yl)amino]benzamide |
| 310 | N-methyl-5-(methylthio)-2-[(1-phenyl-1H-pyrazol-5-yl)amino]benzamide |
| 311 | N-ethyl-5-(methylthio)-2-[(1-phenyl-1H-pyrazol-5-yl)amino]benzamide |
| 312 | N-isopropyl-5-(methylthio)-2-[(1-phenyl-1H-pyrazol-5-yl)amino]benzamide |
| 313 | N,N-diethyl-5-(methylthio)-2-[(1-phenyl-1H-pyrazol-5-yl)amino]benzamide |
| 314 | N-[4-(methylthio)-2-(piperidin-1-ylcarbonyl)phenyl]-1-phenyl-1H-pyrazol-5-amine |
| 315 | N-(2-{3-methoxy-4-[(4-methylpiperazin-1-yl)sulfonyl]phenyl}ethyl)-5-(methylthio)-2-[(1-phenyl-1H-pyrazol-5-yl)amino]benzamide |
| 316 | N-isopropyl-2-{[3-methyl-1-(4-methylphenyl)-1H-pyrazol-5-yl]amino}benzamide |
| 317 | 2-{[3-methyl-1-(4-methylphenyl)-1H-pyrazol-5-yl]amino}-N-phenylbenzamide |
| 318 | 5-methoxy-N-methyl-2-{[3-methyl-1-(4-methylphenyl)-1H-pyrazol-5-yl]amino}benzamide |
| 319 | N-ethyl-5-methoxy-2-{[3-methyl-1-(4-methylphenyl)-1H-pyrazol-5-yl]amino}benzamide |
| 320 | N-isopropyl-5-methoxy-2-{[3-methyl-1-(4-methylphenyl)-1H-pyrazol-5-yl]amino}benzamide |
| 321 | 5-methoxy-2-{[3-methyl-1-(4-methylphenyl)-1H-pyrazol-5-yl]amino}-N-phenylbenzamide |
| 322 | 2-{[3-methyl-1-(4-methylphenyl)-1H-pyrazol-5-yl]amino}-N-(2-methylphenyl)benzamide |
| 323 | N-(2-fluorophenyl)-2-{[3-methyl-1-(4-methylphenyl)-1H-pyrazol-5-yl]amino}benzamide |

TABLE 12b-continued

| Ex. No. | IUPAC Name |
|---|---|
| 324 | 2-{[3-methyl-1-(4-methylphenyl)-1H-pyrazol-5-yl]amino}-N-pyridin-4-ylbenzamide |
| 325 | 2-{[3-methyl-1-(4-methylphenyl)-1H-pyrazol-5-yl]amino}-N-pyridin-3-ylbenzamide |

The following examples represent secondary and tertiary amides derived from a sequence consisting of Buchwald-type coupling, hydrolysis and subsequent amide formation.

TABLE 13a

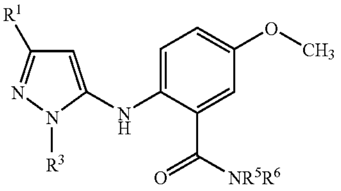

| Ex. No. | $R^1$ | $R^3$ | $R^5$ | $R^6$ | LC-MS RT (min) | LC-MS $[M + H]^+$ |
|---|---|---|---|---|---|---|
| 326 | Me | Ph | i-Pr | H | 2.80 | 365.1 |
| 327 | Ph | Ph | $(CH_2)_2OH$ | H | 3.56 | 429.2 |

TABLE 13b

| Ex. No. | IUPAC Name |
|---|---|
| 326 | N-isopropyl-5-methoxy-2-[(3-methyl-1-phenyl-1H-pyrazol-5-yl)amino]benzamide |
| 327 | 2-[(1,3-diphenyl-1H-pyrazol-5-yl)amino]-N-(2-hydroxyethyl)-5-methoxybenzamide |

The following examples represent N-acylsulfonamides derived from the coupling of a carboxylic acid precursor with a sulfonamide.

EXAMPLE 328

Preparation of 2-[(1,3-diphenyl-1H-pyrazol-5-yl)amino]-5-methoxy-N-[(2-methylphenyl)sulfonyl]benzamide

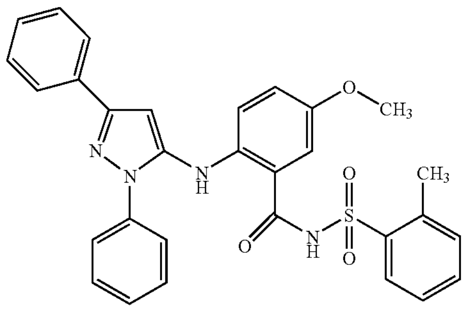

To a solution of 2-[(1,3-diphenyl-1H-pyrazol-5-yl)amino]-5-methoxybenzoic acid (Example 29) (100 mg, 0.26 mmol) in dichloromethane (3 mL) were added o-toluenesulfonamide (53.3 mg, 0.31 mmol), EDCI (99.47 mg, 0.52 mmol), DMAP (63.40 mg, 0.52 mmol), and triethylamine (0.127 mL, 0.91 mmol). The reaction mixture was stirred for 2 h, and then diluted with dichloromethane (10 mL) and water (20 mL). The organic phase was separated and then washed with brine, dried ($Na_2SO_4$), filtered, and concentrated under reduced pressure. The residue was purified by silica gel flash chromatography using 90% EtOAc/hexane, to afford the product (13.9 mg, 10.0%) as a white solid. $^1H$ NMR (300 MHz, DMSO-$d_6$) δ 2.56 (s, 3H), 3.74 (s, 3H) 6.67 (s, 1H), 7.03 (dd, 2H), 7.26-7.60 (m, 14H), 7.84 (dd, 2H), 7.94 (d, 1H). ES-MS m/z 539.1 ($MH^+$); HPLC RT (min) 3.71.

The following compounds were synthesized using the same method as Example 328.

TABLE 14a

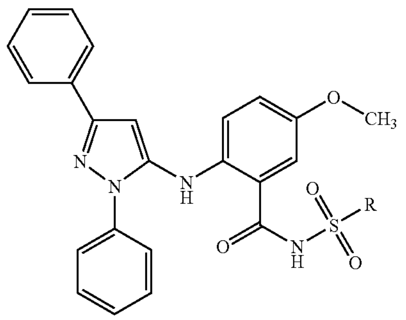

| Ex. No. | R | LC-MS RT (min) | LC-MS $[M + H]^+$ |
|---|---|---|---|
| 329 | 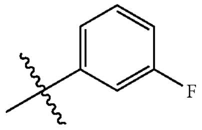 | 3.70 | 543.2 |
| 330 | 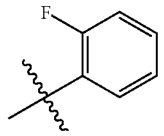 | 3.61 | 543.2 |

TABLE 14b

| Ex. No. | IUPAC Name |
|---|---|
| 329 | 2-[(1,3-diphenyl-1H-pyrazol-5-yl)amino]-N-[(3-fluorophenyl) sulfonyl]-5-methoxybenzamide |
| 330 | 2-[(1,3-diphenyl-1H-pyrazol-5-yl)amino]-N-[(2-fluorophenyl)sulfonyl]-5-methoxybenzamide |

The following examples represent oxadiazoles derived from a transformation of the carboxylic acid group into an oxadiazole moiety.

EXAMPLE 331

Preparation of N-[4-methoxy-2-(3-methyl-1,2,4-oxadiazol-5-yl)phenyl]-3-methyl-1-phenyl-1H-pyrazol-5-amine

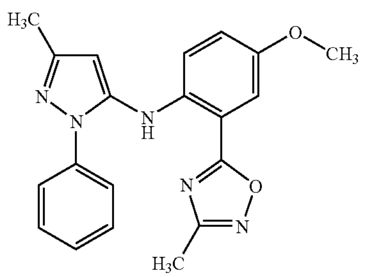

Step 1: Preparation of N-hydroxy-acetamidine

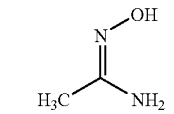

To a solution of hydroxylamine (2.21 g, 67 mmol) in water (5 mL) was added acetonitrile (3.5 mL, 2.75 g, 67 mmol). Ethanol was added dropwise until a clear solution resulted. The mixture was cooled to 0° C., and sodium ethoxide (21.7 g of a 21% solution in ethanol, 67 mmol) was added. After completion of the addition, the reaction mixture was warmed to 35° C. and stirred at that temperature for 3 days. The reaction mixture was then cooled to rt, and the solid residue (NaCl) was removed by filtration and washed with acetonitrile. The filtrate and the washings were combined, the solvents partially evaporated in vacuo, and conc HCl was added until the pH was ~1.0. The solvents were then evaporated until a yellow residue appeared. This residue was dissolved in hot EtOH and reprecipitated by adding diethylether. Needle-like crystals appeared from the solution which were filtered off. The filtrate was saved and kept in the freezer for several days to get a second crop. The product was obtained as colorless crystals (1.12 g, 15%). $^1$H NMR (400 MHz, DMSO-$d_6$). δ 2.09 (s, 3H), 8.45 (br, s, 1H), 10.64-10.90 (br, 1H), 12.2-12.5 (br, 1H).

Step 2: Preparation of N-[(1Z)-N-hydroxyethanimidoyl]-5-methoxy-2-[(3-methyl-1-phenyl-1H-pyrazol-5-yl)amino]benzamide

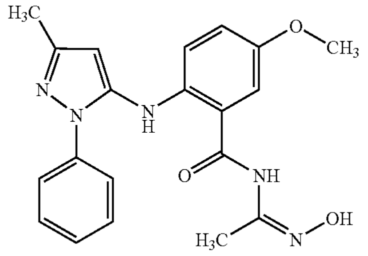

To a mixture of 2-[(3-methyl-1-phenyl-1H-pyrazol-5-yl) amino]benzoic acid (400 mg, 1.04 mmol) (prepared by the sequence of Buchwald-type coupling and hydrolysis, similar to Examples 108 and 109), HOAT (186 mg, 1.39 mmol), and EDCI (263 mg, 1.39 mmol) in DMF (7 mL) at −20° C. was added triethylamine (0.45 mL, 3.25 mmol). After stirring at that temperature for 15 min, N-hydroxy-acetamidine (305 mg, 2.78 mmol) was added, and the temperature was slowly raised to rt. Stirring was continued for 16 h, the solvent was evaporated in vacuo and the residue was partitioned between water and EtOAc. The layers were separated, and the aqueous layer was extracted with EtOAc. The combined organic layers were washed successively with 5% citric acid, saturated aqueous $Na_2CO_3$ solution and brine, dried ($MgSO_4$), filtered, and concentrated to give 147 mg of a crude solid. This solid was used in the next step with no further purification. ES-MS m/z 380.1 ($MH^+$); HPLC RT (min) 2.53.

Step 3: Preparation of N-[4-methoxy-2-(3-methyl-1,2,4-oxadiazol-5-yl)phenyl]-3-methyl-1-phenyl-1H-pyrazol-5-amine

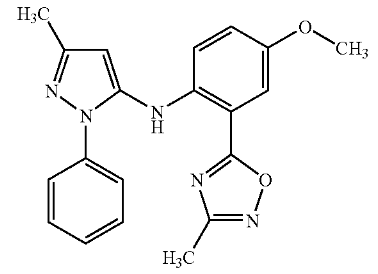

To a solution of the crude N-[(1Z)-N-hydroxyethanimidoyl]-2-[(3-methyl-1-phenyl-1H-pyrazol-5-yl)amino]benzamide (257 mg, 0.41 mmol) in THF (3 mL) was added (methoxycarbonylsulfamoyl)triethylammonium hydroxide (Burgess reagent) (145 mg, 0.61 mmol). The flask was flushed with argon and refluxed for 3 h under argon. The reaction mixture was the cooled to rt, filtered through a small plug of silica gel, and the plug was eluted with EtOAc. The filtrate was concentrated under reduced pressure, and the residue purified by preparative TLC on silica gel using EtOAc/Hex (1:2, v/v) to give the title product as a solid (5.5 mg, 4% overall). $^1$H NMR (400 MHz, $CD_3CN$). δ 2.30 (s, 3H), 2.32 (s, 3H), 3.82 (s, 3H), 6.16 (s, 1H), 7.09 (dd, 1H), 7.21 (d, 1H), 7.38-7.42 (m, 1H), 7.42-7.50 (m, 3H), 7.50-7.58 (m, 2H), 9.46 (br, s, 1H). ES-MS m/z 362.2 ($MH^+$); HPLC RT (min) 3.28.

EXAMPLE 332

Preparation of N-[4-methoxy-2-(5-methyl-1,2,4-oxadiazol-3-yl)phenyl]-1phenyl-1H-pyrazol-5-amine

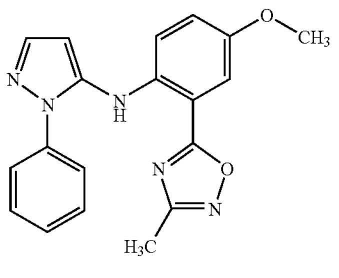

Using the method described for Example 331, the title compound was similarly prepared; ES-MS m/z 348.3 ($MH^+$); HPLC RT (min) 3.25.

The following examples represent sulfonamides made by coupling of a suitable dibenzylsulfonamide precursor with a 5-aminopyrazole which is followed by deprotection of the two benzyl groups.

EXAMPLE 333

Preparation of 2-{[3-tert-butyl-1-(2-methylphenyl)-1H-pyrazol-5-yl]amino}benzenesulfonamide

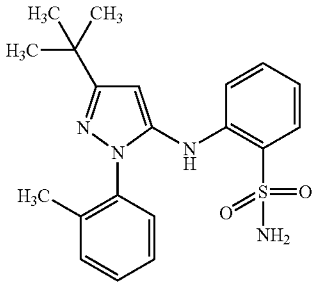

Step 1: Preparation of N,N-dibenzyl-2-bromobenzenesulfonamide

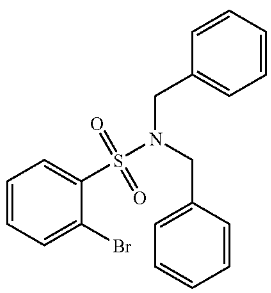

2-Bromobenzenesulfonyl chloride (1.0 g, 3.91 mmol) and triethylamine (455 mg, 0.63 mL, 4.5 mmol) were dissolved in THF (15 mL), and the mixture was cooled to 10° C. Dibenzylamine (849 mg, 0.83 mL, 4.3 mmol) was then added dropwise. The cooling bath was removed, and the reaction mixture was stirred for 10 h at rt and then an additional 6 h at 60° C. After cooling to rt, the solvent was removed under reduced pressure, and ethyl acetate was added. The organic layer was successively washed with 1N HCl, water, semi-saturated aq $Na_2CO_3$ solution, water, and brine. After drying with $Na_2SO_4$ and filtration, the solvent was removed under reduced pressure to afford the title compound as off-white crystals (1.44 g, 88%). $^1$H NMR (400 MHz, $CDCl_3$) δ 4.42 (s, 4H), 7.08 (m, 4H), 7.27 (m, 6H), 7.41 (m, 2H), 7.78 (d, 1H), 8.19 (d, 1H).

Step 2: Preparation of N,N-dibenzyl-2-{[3-tert-butyl-1-(2-methylphenyl)-1H-pyrazol-5-yl]amino}benzenesulfonamide

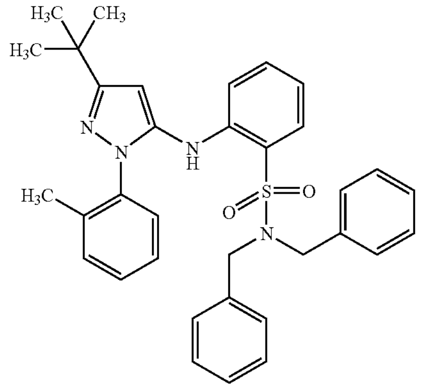

N,N-Dibenzyl-2-bromobenzenesulfonamide (from Step 1, 333 mg, 0.80 mmol), 3-tert-butyl-1-(2-methylphenyl)-1H-pyrazol-5-amine (Intermediate C), cesium carbonate (365 mg, 1.12 mmol), $Pd_2dba_3$ (41.4 mg, 0.04 mmol), and BINAP (49.8 mg, 0.08 mmol) were dissolved in toluene (7 mL) under nitrogen, and the flask was heated at 110° C. for 20 h. The reaction mixture was cooled to rt, and the solid residue removed by filtration. The solvent was removed under reduced pressure and the residue purified via silica gel flash chromatography using EtOAc/hexane (1:12, v/v) to afford the title compound as a viscous oil (348 mg, 77%). $^1$H NMR (400 MHz, $CDCl_3$) δ 1.40 (s, 9H), 2.03 (s, 3H), 3.99 (s, 4H), 6.10 (s, 1H), 6.88 (m, 4H), 7.07 (m, 1H), 7.10-7.27 (m, 10H), 7.38 (d, 1H), 7.47 (t, 1H), 7.71 (s, 1H), 7.77 (d, 1H). ES-MS m/z 565.4 $(MH)^+$; HPLC RT (min) 4.37.

Step 3. Preparation of 2-{[3-tert-butyl-1-(2-methylphenyl)-1H-pyrazol-5-yl]amino}benzenesulfonamide

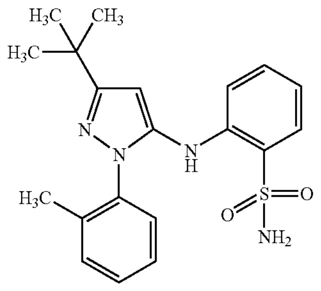

N,N-Dibenzyl-2-{[3-tert-butyl-1-(2-methylphenyl)-1H-pyrazol-5-yl]amino}benzene-sulfonamide (from Step 2, 240 mg, 0.42 mmol) was added to conc $H_2SO_4$ (3 mL), and the mixture was vigorously stirred for 20 min. The mixture was poured onto ice, and conc NaOH solution was added until a pH of ~7.5 was reached. The aqueous layer was extracted 2× with EtOAc, and the combined organic layers were dried with $Na_2SO_4$, filtered, and concentrated under reduced pressure. Purification by silica gel flash chromatography using EtOAc/hexane (1:3, v/v) afforded the title compound as a white solid (104 mg, 64%). $^1$H NMR (δ 400 MHz, $CD_2Cl_2$) 61.39 (s, 9H), 2.09 (s, 3H), 4.50 (br, 2H), 6.20 (s, 1H), 7.94 (t, 1H), 7.23 (m, 4H), 7.34 (m, 2H), 7.45 (t, 1H), 7.73 (d, 1H). ES-MS m/z 385.2 ($MH^+$); HPLC RT (min) 3.11.

EXAMPLE 334

Preparation of 2-{[1-(2-methylphenyl)-3-(trifluoromethyl)-1H-pyrazol-5-yl]amino}benzenesulfonamide

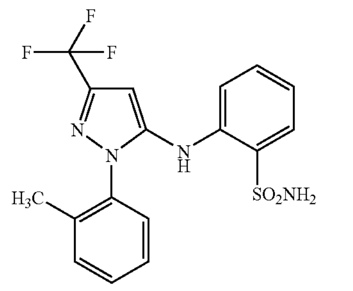

Using the method described for Example 333, the title compound was similarly prepared; ES-MS m/z 397.1 ($MH^+$); HPLC RT (min) 3.18.

EXAMPLE 335

Preparation of 2-{[4-iodo-1-(2-methylphenyl)-3-(4-methylphenyl)-1H-pyrazol-5-yl]amino}-5-methylbenzoic acid

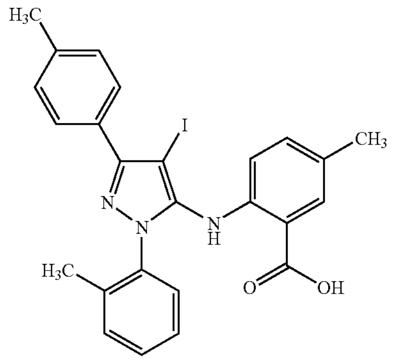

To a solution of 5-methyl-2-{[1-(2-methylphenyl)-3-(4-methylphenyl)-1H-pyrazol-5-yl]amino}benzoic acid (Example 65), (49.5 mg, 0.13 mmol) in AcOH/DCM (1:1, v/v) (2 mL) was added a solution of NIS (28 mg, 0.13 mmol) in DCM (1 mL). The reaction was stirred at rt for 3 h. Water (1 mL) was added to the reaction mixture. The water layer was extracted with DCM (2 mL), and the combined organic layers were washed with sodium sulfite and brine, and concentrated under reduced pressure. The crude product was subjected to HPLC purification with a gradient elution from 30% to 95% acetonitrile in water to afford 9.1 mg (14%) of the title compound. $^1$H NMR (300 MHz, $CD_2Cl_2$) δ 8.88 (s, 1H), 7.85 (d, 2H), 7.74 (s, 1H), 7.18-7.32 (m, 7H), 6.58 (d, 1H), 2.41 (s, 3H), 2.25 (s, 3H), 2.21 (s, 3H). ES-MS m/z 524.1 ($MH^+$); HPLC RT (min) 4.35.

EXAMPLE 336

Preparation of 2-{[3-tert-butyl-4-fluoro-1-(2-methylphenyl)-1H-pyrazol-5-yl]amino}-5-methoxybenzoic acid

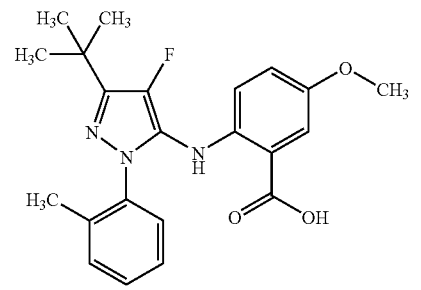

To a solution of 2-{[3-tert-butyl-1-(2-methylphenyl)-1H-pyrazol-5-yl]amino}-5-methoxybenzoic acid (Example 4), (49 mg, 0.13 mmol) in $CH_3CN$ (1 mL) was added [(1-(chloromethyl)4-fluoro-1,4-diazoniabicyclo[2.2.2]octane bis(tetrafluoroborate)] (SELECTFLUOR®) (46 mg, 0.13 mmol), and the mixture was stirred at rt for 16 h. The solid was filtered off and the filtrate was subjected to HPLC purification with a gradient elution from 10% to 90% acetonitrile in water to afford 4 mg (8%) of the desired product. $^1$H NMR (300 MHz, $CD_2Cl_2$) δ 8.62 (s, 1H), 7.40 (d, 1H), 7.16-7.35 (m, 4H), 7.05 (dd, 1H), 7.76 (dd, 1H), 3.75 (s, 3H), 2.12 (s, 3H), 1.40 (s, 9H). ES-MS m/z 398.2 ($MH^+$); HPLC RT (min) 4.06.

EXAMPLE 337

Preparation of methyl 5-methoxy-2-{methyl[3-methyl-1-(2-methylphenyl)-4-phenyl-1H-pyrazol-5-yl]amino}benzoate

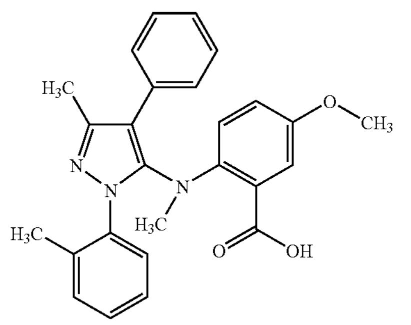

Step 1: Preparation of methyl 5-methoxy-2-{methyl [3-methyl-1-(2-methylphenyl)$_4$-phenyl-1H-pyrazol-5-yl]amino}benzoate

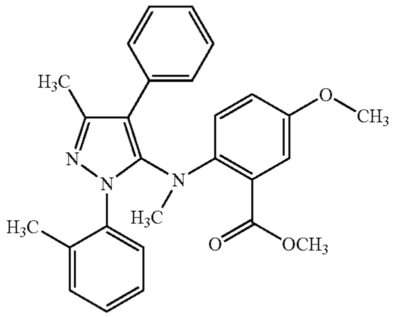

To a suspension of NaH (60% dispersion in mineral oil; 0.28 g, 7 mmol) in DMF (10 mL) at rt was added a solution of methyl 5-methoxy-2-{[3-methyl-1-(2-methylphenyl)-4-phenyl-1H-pyrazol-5-yl]amino}benzoate (1.495 g, 3.5 mmol) in DMF (15 mL) dropwise. The mixture was stirred for 0.5 h, and then iodomethane (0.88 mL, 14 mmol) was added. The reaction mixture was stirred at rt for 1 h. Water (100 mL) was cautiously added, and the mixture was extracted with ethyl acetate (25 mL×3). The combined organic phases were washed with a saturated solution of sodium bicarbonate (50 mL), dried ($Na_2SO_4$), filtered, and concentrated under reduced pressure. The residue was purified by silica gel flash chromatography (EtOAc/hexanes 1:12) to afford the title compound (1.18 g, 68%) as a pale yellow solid. $^1$H NMR (400 MHz, acetone-$d_6$) δ 2.1 (s, 3H), 2.3 (s, 3H), 2.9 (s, 3H), 3.65 (s, 3H), 3.7 (s, 3H), 6.87-6.92 (m, 2H), 6.94-6.98 (m, 1H), 7.03-7.09 (m, 1H), 7.15-7.27 (m, 4H), 7.30-7.36 (m, 2H), 7.39-7.43 (m, 2H). ES-MS m/z 442.3 (MH$^+$); HPLC RT (min) 3.96.

Step 2: Preparation of 5-methoxy-2-{methyl[3-methyl-1-(2-methylphenyl)-4-phenyl-1H-pyrazol-5-yl] amino}benzoic acid

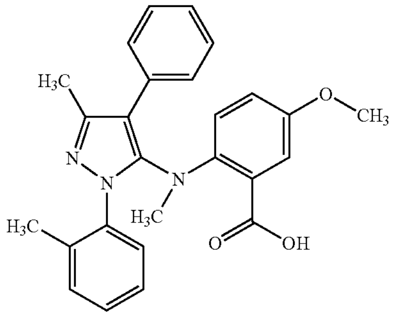

To a solution of the compound of step 1 (60 mg, 0.129 mmol) in a mixture of THF (4 mL), water (4 mL), and MeOH (2 mL), was added LiOH (32 mg, 1.32 mmol). The reaction mixture was vigorously stirred for 24 h, after which it was concentrated under reduced pressure, and diluted with water (10 mL). The solution was then acidified to pH ~1 using 1 N HCl, and then extracted with $CH_2Cl_2$ (3×20 mL). The combined organic layers were dried ($Na_2SO_4$), filtered, and concentrated under reduced pressure. The residue was then purified by preparative HPLC to afford the title compound (32 mg, 58%) as a white solid. $^1$H NMR (400 MHz, acetone-$d_6$) δ 2.12 (s, 3H), 2.23 (s, 3H), 2.9 (s, 3H), 3.74 (s, 3H), 6.87-6.90 (m, 2H), 6.92-6.98 (m, 1H), 7.03-7.11 (m, 1H), 7.16-7.27 (m, 4H), 7.30-7.36 (m, 2H), 7.40-7.45 (m, 2H); ES-MS m/z 428.3 (MH$^+$); HPLC RT (min) 3.54.

EXAMPLE 338

Preparation of 2-[[3-tert-butyl-1-(2,6-dimethylphenyl)-1H-pyrazol-5-yl](methyl)amino]-5-methoxybenzoic acid

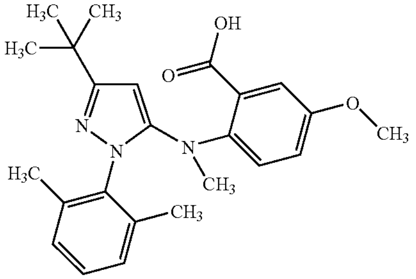

This compound was prepared using the procedure as described in Example 337. $^1$H NMR (400 MHz, $CD_3OD$) δ 1.40 (s, 9H), 1.95 (s, 6H), 3.26 (s, 3H), 3.74 (s, 3H), 6.81 (dd, 1H), 6.93 (m, 4H), 7.13 (m, 1H), 7.26 (d, 1H). ES-MS m/z 408.3 (MH$^+$); HPLC RT (min) 2.65.

Using the procedures as described in Examples 108 and 109, the following compounds can be made. The aminopyrazoles used in the coupling reactions can be made as described for Intermediate B starting from commercially available carboxylic acid methyl or ethyl esters.

TABLE 15

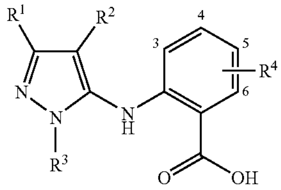

| Ex. No. | $R^1$ | $R^2$ | $R^3$ | $R^4$ | IUPAC name |
|---|---|---|---|---|---|
| 339 | 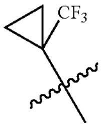 | H | 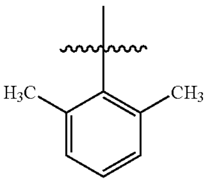 | 5-OMe | 2-({1-(2,6-dimethylphenyl)-3-[1-(trifluoromethyl)cyclopropyl]-1H-pyrazol-5-yl}amino)-5-methoxybenzoic acid |
| 340 | 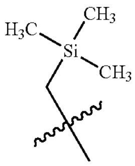 | H | 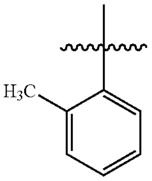 | 5-OMe | 5-methoxy-2-({1-(2-methylphenyl)-3-[(trimethylsilyl)methyl]-1H-pyrazol-5-yl}amino)benzoic acid |
| 341 | 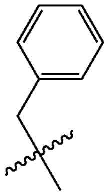 | H | 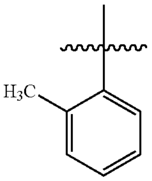 | 5-OMe | 2-{[3-benzyl-1-(2-methylphenyl)-1H-pyrazol-5-yl]amino}-5-methoxybenzoic acid |
| 342 | 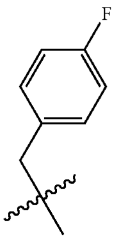 | H | 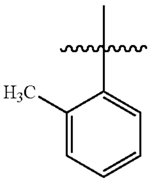 | 5-OMe | 2-{[3-(4-fluorobenzyl)-1-(2-methylphenyl)-1H-pyrazol-5-yl]amino}-5-methoxybenzoic acid |
| 343 | 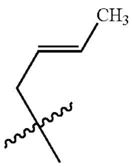 | H | 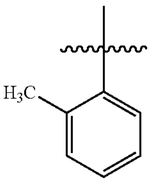 | 5-OMe | 2-{[3-[(2E)-but-2-en-1-yl]-1-(2-methylphenyl)-1H-pyrazol-5-yl]amino}-5-methoxybenzoic acid |
| 344 | 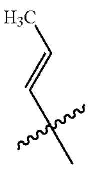 | H | 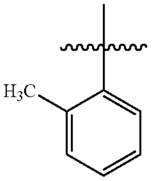 | 5-OMe | 5-methoxy-2-({1-(2-methylphenyl)-3-[(1E)-prop-1-en-1-yl]-1H-pyrazol-5-yl}amino)benzoic acid |

TABLE 15-continued

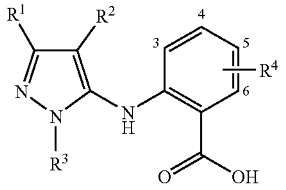

| Ex. No. | $R^1$ | $R^2$ | $R^3$ | $R^4$ | IUPAC name |
|---|---|---|---|---|---|
| 345 | 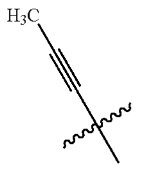 | H | 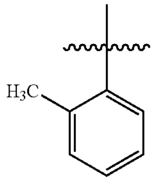 | 5-OMe | 5-methoxy-2-{[1-(2-methylphenyl)-3-prop-1-yn-1-yl-1H-pyrazol-5-yl]amino}benzoic acid |

The compounds of the present invention may be employed in the treatment of diabetes, including both type 1 and type 2 diabetes (non-insulin dependent diabetes mellitus). Such treatment may also delay the onset of diabetes and diabetic complications. The compounds may be used to prevent subjects with impaired glucose tolerance from proceeding to develop type 2 diabetes. Other diseases and conditions that may be treated or prevented using compounds of the invention in methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The compounds of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease.

The compounds of the present invention may also be useful for treating physiological disorders related to, for example, cell differentiation to produce lipid accumulating cells, regulation of insulin sensitivity and blood glucose levels, which are involved in, for example, abnormal pancreatic beta-cell function, insulin secreting tumors and/or autoimmune hypoglycemia due to autoantibodies to insulin, autoantibodies to the insulin receptor, or autoantibodies that are stimulatory to beta-cells), macrophage differentiation which leads to the formation of atherosclerotic plaques, inflammatory response, carcinogenesis, hyperplasia, adipocyte gene expression, adipocyte differentiation, reduction in the pancreatic beta-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Compounds of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, β-adrenergic agents, α-interferon and drugs used to treat HIV infection.

The compounds of the present invention may be used alone or in combination with additional therapies and/or compounds known to those skilled in the art in the treatment of diabetes and related disorders. Alternatively, the methods and compounds described herein may be used, partially or completely, in combination therapy.

The compounds of the invention may also be administered in combination with other known therapies for the treatment of diabetes, including PPAR agonists, sulfonylurea drugs, non-sulfonylurea secretagogues, α-glucosidase inhibitors, insulin sensitizers, insulin secretagogues, hepatic glucose output lowering compounds, insulin and anti-obesity drugs. Such therapies may be administered prior to, concurrently with or following administration of the compounds of the invention. Insulin includes both long and short acting forms and formulations of insulin. PPAR agonist may include agonists of any of the PPAR subunits or combinations thereof. For example, PPAR agonist may include agonists of PPAR-α, PPAR-γ, PPAR-δ or any combination of two or three of the subunits of PPAR. PPAR agonists include, for example, rosiglitazone and pioglitazone. Sulfonylurea drugs include, for example, glyburide, glimepiride, chlorpropamide, and glipizide. α-glucosidase inhibitors that may be useful in treating diabetes when administered with a compound of the invention include acarbose, miglitol and voglibose. Insulin sensitizers that may be useful in treating diabetes include thiazolidinediones and non-thiazolidinediones. Hepatic glucose output lowering compounds that may be useful in treating diabetes when administered with a compound of the invention include metformin, such as Glucophage and Glucophage XR. Insulin secretagogues that may be useful in treating diabetes when administered with a compound of the invention include sulfonylurea and non-sulfonylurea drugs: GLP-1, GIP, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, compounds of the invention are used in combination with insulin secretagogues to increase the sensitivity of pancreatic beta-cells to the insulin secretagogue.

Compounds of the invention may also be used in methods of the invention in combination with anti-obesity drugs. Anti-obesity drugs include β-3 agonists, CB-1 antagonists, appetite suppressants, such as, for example, sibutramine (Meridia), and lipase inhibitors, such as, for example, orlistat (Xenical).

Compounds of the invention may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Compounds of the invention may also be used in combination with anti-hypertensive drugs, such as, for example, β-blockers and ACE inhibitors.

Such co-therapies may be administered in any combination of two or more drugs (e.g., a compound of the invention in combination with an insulin sensitizer and an anti-obesity drug). Such co-therapies may be administered in the form of pharmaceutical compositions, as described above.

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

Based on well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient (e.g., compounds) to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.0001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a therapeutically effective amount of a compound. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A therapeutically effective amount of a compound is that amount which produces a result or exerts an influence on the particular condition being treated. The compounds described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug (e.g., compound) with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC—CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., $20^{th}$ edition, 2000).

The following examples are presented to illustrate the invention described herein, but should not be construed as limiting the scope of the invention in any way.

Capsule Formulation

| A capsule formula is prepared from: | |
|---|---|
| Compound of this invention | 10 mg |
| Starch | 109 mg |
| Magnesium stearate | 1 mg |

The components are blended, passed through an appropriate mesh sieve, and filled into hard gelatin capsules.

Tablet Formulation

| A tablet is prepared from: | |
|---|---|
| Compound of this invention | 25 mg |
| Cellulose, microcrystalline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A mg/mL solution of the desired compound of this invention is made using sterile, injectable water, and the pH is adjusted if necessary. The solution is diluted for administration with sterile 5% dextrose and is administered as an IV infusion.

Intramuscular Suspension

The following intramuscular suspension is prepared:

-continued

| | |
|---|---|
| Compound of this invention | 50 μg/mL |
| Sodium carboxymethylcellulose | 5 mg/mL |
| TWEEN 80 | 4 mg/mL |
| Sodium chloride | 9 mg/mL |
| Benzyl alcohol | 9 mg/mL |

The suspension is administered intramuscularly.

Hard Shell Capsules

A large number of unit capsules are prepared by filling standard two-piece hard galantine capsules each with powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into molten gelatin to form soft gelatin capsules containing the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin, and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

BIOLOGICAL EVALUATION

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia, the following assays may be used.

In Vitro Assay

Insulin Secretion from INS-1 Cells

INS-1 cells were isolated from X-ray induced rat insulinoma (Asfari, et al., Endocrinology 130:167, 1992). INS-1 cells were seeded at 30,000 cells per well in Biocoat Collagen1 Cellware 96-well plates and incubated for 4-5 days. The cells were then treated for 2 days with complete media (RPMI 1640, 10% Fetal Bovine Serum, 100 μg/mL Penicillin/Streptomycin, 0.5 mM sodium pyruvate, 10 mM HEPES, and 50 μM beta-mercaptoethanol) adjusted to 3 mM glucose. After the two-day treatment, the cells were washed with Krebs-Ringer-Bicarbonate-HEPES (KRBH) containing 3 mM glucose. The cells were then incubated for 30 min in the same buffer. The cells were incubated for an additional 2 h in the presence of the desired concentration of glucose and compounds. The supernatants were harvested.

To determine the amount of insulin secreted, the supernatants were mixed with anti-insulin antibody and a tracer amount of $^{125}$I-insulin in phosphate buffered saline containing 0.5% bovine serum albumin. Protein A coated SPA (scintillation proximity assay) beads were added. The plates were incubated for 5-20 h and counted on a scintillation counter to measure insulin levels. Activity for compounds at a given concentration was expressed as a fold-stimulation of insulin secretion relative to controls.

The compounds of the invention (measured at 10 μM) were found to be active in the INS-1 assay.

Insulin Secretion from Dispersed Rat Islet Cells

Insulin secretion of dispersed rat islets mediated by a number of compounds of the present invention was measured as follows. Islets of Langerhans, isolated from male Sprague-Dawley rats (200-250 g), were digested using collagenase. The dispersed islet cells were treated with trypsin, seeded into 96 V-bottom plates, and pelleted. The cells were then cultured overnight in media with or without compounds of this invention. The media was aspirated, and the cells were pre-incubated with Krebs-Ringer-HEPES buffer containing 3 mM glucose for 30 minutes at 37° C. The pre-incubation buffer was removed, and the cells were incubated at 37° C. with Krebs-Ringer-HEPES buffer containing the appropriate glucose concentration (e.g., 8 mM) with or without compounds for an appropriate time. In some studies, an appropriate concentration of GLP-1 or forskolin was also included. A portion of the supernatant was removed and its insulin content was measured by SPA. The results were expressed as "fold over control" (FOC).

In Vivo Assay

Effect of Compounds on Intraperitoneal Glucose Tolerance in Rats

The in vivo activities of the compounds of this invention when administered via oral gavage were examined in rats. Rats fasted overnight were given an oral dose of vehicle control or compound. Three hours later, basal blood glucose was measured, and the rats were given 2 g/kg of glucose intraperitoneally. Blood glucose was measured again after 15, 30, and 60 min. A representative compound of this invention significantly reduced blood glucose levels relative to the vehicle following the IPGTT (Intraperitoneal Glucose Tolerance Test).

Target Identification

Use of Formula (I) Compounds to Identify Biological Targets

Compounds of Formula (I) of the current invention are also useful for identifying their associated biological target (s) (e.g., nucleic acids, peptides, polypeptides, proteins, carbohydrates, lipids, or other molecules) effecting the functional response of insulin secretion. Such targets, or protein molecules that are modulated by the compounds of present invention can be identified by several means.

For example, one such method of target identification can be accomplished, by photoaffinity labeling techniques well-known in the art. In such a procedure, compounds of Formula (I) that contain a photoactive group, such as a benzoylphenyl group, are prepared and additionally labeled with a radioactive isotope such as tritium. As an example, a suitable Formula (I) compound useful for such experiments is a radioactively tagged derivative of the benzophenone analog described in Example 207. The preparation of such a compound is shown in Reaction Scheme M below, starting from the compound of Formula (X). The chloro-containing starting material may be made using a procedure similar to that described for Example 142. In stepwise fashion, this starting material is functionalized with a benzoyl group and allowed to undergo a tritium-halogen exchange reaction, to provide a probe molecule of Formula (XIII). The methods for replacement of a chlorine atom by tritium are well know in the art and may be done without affecting the integrity of the keto group of the benzophenone moiety (e.g., Mesange, et al. Bioconj. Chem. 13:766-772, 2002; Held, et al., Labelled Compd. Radiopharm. 39:501-508, 1997; Kaspersen, et al., Rec. Trav. Chim. Pays-Bas 112:191-199, 1993; Hergert, et al., Pharmazie 38:28-29, 1983).

This probe molecule is then allowed to come in contact with pancreatic beta-cell lysate homogenate (or any biological sample, such as a sample obtained from an organism (e.g., mammal) or from components (e.g., cells, biological tissue or fluid) of an organism, cell line or tissue culture sample; or the sample may be a sample derived from a patient including, but are not limited to, tissue or cells therefrom) containing the suspected target(s), incubated for a period of time sufficient to effect association of the probe molecule with the target protein, then the mixture is irradiated with light at the wavelength of the photoactive group of the probe molecule. The protein and probe molecule that become covalently bound as a result of the irradiation is then purified using standard methods, facilitated by the radioactivity of probe/target complex as a means to differentiate it from the rest of the lysate mixture. Identification of the purified protein (the probe/target complex) is then conducted using methods well described in the art (see, e.g., Dorman, et al., Tibtech. 18:64-77, 2000).

Reaction Scheme M

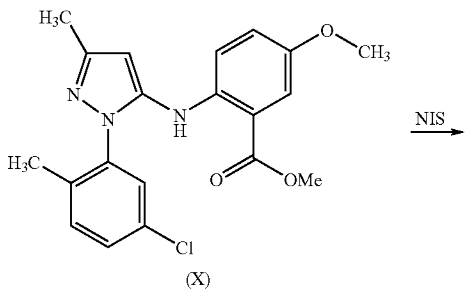

(X)

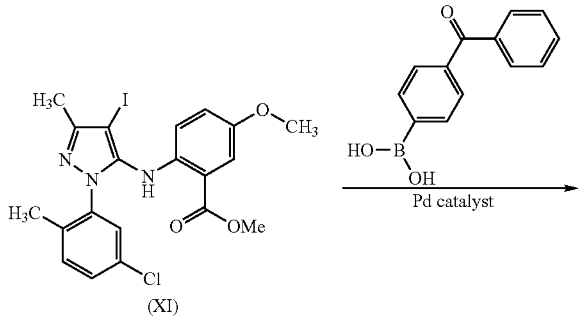

(XI)

-continued

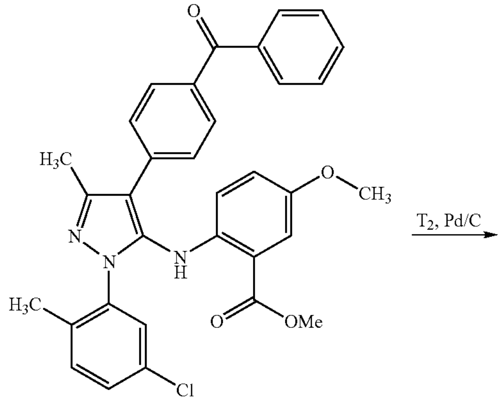

(XII)

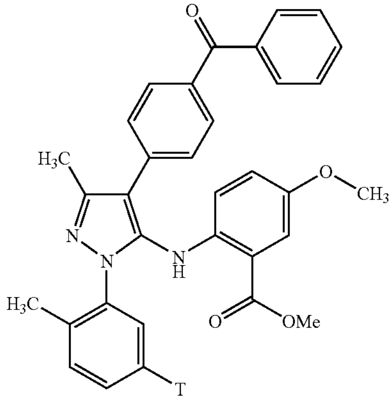

(XIII)

Another method using the compounds of Formula (I) to identify the biological target effecting the functional response of insulin secretion is the so called drug "pull-down" experiments (see, e.g., Graves, et al., Rec. Prog. Horm. Res. 58:1-24, 2003). Formula (I) compounds containing functional groups that are suitable for chemical coupling (e.g., carboxylic acid groups, amino groups, alcohol groups) may be coupled to a commercially available polymer (resins) containing a suitably reactive linker group. For example, polymeric beads containing an amino linker may be allowed to react with a Formula (I) compound where X=COOH to form an amide, said amide being bound to the polymeric beads and thus, immobilized. The polymeric beads containing immobilized Formula (I) compound may then be used as bait for appropriate pancreatic beta-cell tissue lysates, by allowing the polymer beads to come in contact with the lysate, incubating for a period of time sufficient for the target proteins to form a complex with the polymer, removing the unbound protein material from the polymer, and cleaving of the bound protein from the polymer. Thus, purified protein target(s) of interest may then be identified by mass spectrometric analysis using techniques well know in the art (see, e.g., Kim, et al., Biochem. Mol. Biol. 36:299-304, 2003.

All publications and patents mentioned in the above specification are incorporated herein by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims. Those skilled in the art will recognize, or be able to ascertain using no more than routine experimentation, many equivalents to the specific embodiments of the invention described herein. Such equivalents are intended to be encompassed by the following claims.

We claim:

1. A compound of Formula (I)

(I)

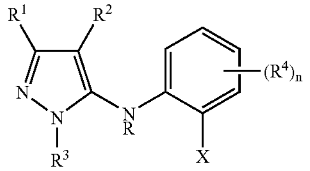

wherein

R is H or $(C_1\text{-}C_6)$alkyl;

$R^1$ is H, $(C_1\text{-}C_6)$alkyl optionally substituted with one substituent selected from the group consisting of $(C_1\text{-}C_4)$ alkoxy, phenyl optionally substituted with halo, and [tri$(C_1\text{-}C_4)$alkyl]silyl, $(C_3\text{-}C_6)$alkenyl, $(C_3\text{-}C_6)$alkynyl, $(C_3\text{-}C_6)$cycloalkyl optionally substituted with up to two substituents selected from the group consisting of $(C_1\text{-}C_3)$alkyl, $CF_3$, and halo, $(C_1\text{-}C_3)$haloalkyl, or phenyl optionally substituted with up to four substituents selected from the group consisting of halo, $(C_1\text{-}C_6)$alkyl optionally substituted with one $(C_1\text{-}C_4)$ alkoxy, $(C_1\text{-}C_6)$alkoxy, $(C_1\text{-}C_3)$haloalkyl, $(C_1\text{-}C_3)$haloalkoxy, $NR^8R^8$, cyano, and $(C_1\text{-}C_6)$alkylthio;

$R^2$ is H, halo, $(C_1\text{-}C_6)$alkyl optionally substituted with one $(C_1\text{-}C_4)$ alkoxy, $(C_3\text{-}C_6)$cycloalkyl optionally substituted with up to two substituents selected from the group consisting of $(C_1\text{-}C_3)$alkyl and halo, $(C_1\text{-}C_3)$haloalkyl, phenyl optionally substituted with up to four substituents selected from the group consisting of $(C_1\text{-}C_6)$alkyl optionally substituted with one $(C_1\text{-}C_4)$ alkoxy, $(C_1\text{-}C_6)$alkoxy, hydroxy, $NR^8R^8$, cyano, $(C_1\text{-}C_6)$alkylthio, halo, $CO_2R^8$,
$(C_1-C_3)$haloalkoxy,
$(C_1-C_4)$acyl, and
benzoyl, or
tetrahydronaphthyl, or indanyl, each of which may be optionally substituted with up to two substituents selected from the group consisting of $(C_1-C_6)$alkoxy, or
$(C_1-C_6)$alkythio, halo, and $(C_1-C_6)$alkyl optionally substituted with one $(C_1-C_4)$alkoxy;
$R^3$ is $(C_1-C_6)$alkyl,
$(C_3-C_6)$cycloalkyl,
benzyl optionally substituted on the aryl ring with up to four substituents selected from the group consisting of
$(C_1-C_6)$alkyl optionally substituted with one $(C_1-C_4)$ alkoxy,
halo,
$(C_1-C_3)$haloalkyl,
$(C_1-C_6)$alkoxy,
$(C_1-C_3)$haloalkoxy,
$NR^8R^8$,
cyano,
$(C_1-C_6)$alkylthio, and
$SO_2(C_1-C_3)$alkyl,
$(C_2-C_3)$haloalkyl, or
phenyl optionally substituted with up to four substituents selected from the group consisting of
$(C_1-C_6)$alkyl optionally substituted with one $(C_1-C_4)$ alkoxy,
halo,
$(C_1-C_3)$haloalkyl,
$(C_1-C_6)$alkoxy,
$(C_1-C_3)$haloalkoxy
$NR^8R^8$,
cyano,
$(C_1-C_6)$alkylthio, and
$SO_2(C_1-C_3)$alkyl;
$R^4$ is $(C_1-C_6)$alkyl optionally substituted with one $(C_1-C_4)$alkoxy,
$(C_1-C_6)$alkoxy,
$(C_1-C_6)$alkylthio,
$(C_1-C_3)$haloalkyl,
$(C_1-C_3)$haloalkoxy,
halo,
$NR^8R^8$,
or
phenyl optionally substituted with up to four substituents selected from the group consisting of
halo,
$(C_1-C_6)$alkyl optionally substituted with one $(C_1-C_4)$ alkoxy,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio;
n=0, 1, 2, or 3;
X is $CO_2R^8$, or $CONR^5R^6$;
$R^5$ is H,
$(C_1-C_6)$alkyl,
$(C_2-C_6)$alkyl substituted with $OR^6$,
benzyl optionally substituted on the aryl ring with up to four substituents selected from the group consisting of
halo, $(C_1-C_6)$alkyl optionally substituted with one $(C_1-C_4)$ alkoxy,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio,
phenyl optionally substituted with up to four substituents selected from the group consisting of
$(C_1-C_6)$alkyl optionally substituted with one $(C_1-C_4)$ alkoxy,
halo,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio,
or
$SO_2$-phenyl said phenyl optionally substituted with up to four substituents selected from the group consisting of
halo
$(C_1-C_6)$alkyl optionally substituted with one $(C_1-C_4)$ alkoxy,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio;
$R^6$ is H or $(C_1-C_6)$alkyl;
$R^7$ is H or methyl;
$R^8$ is H,
$(C_1-C_6)$alkyl,
benzyl optionally substituted on the aryl ring with up to four substituents selected from the group consisting of
halo,
$(C_1-C_6)$alkyl optionally substituted with one $(C_1-C_4)$ alkoxy,
$(C_1-C_3)$alkoxy,
$(C_1-C_3)$haloalkyl,
$(C_1-C_3)$haloalkoxy,
cyano, and
$(C_1-C_6)$alkylthio,
or
phenyl optionally substituted with up to four substituents selected from the group consisting of
$(C_1-C_6)$alkyl optionally substituted with one $(C_1-C_4)$ alkoxy,
halo,
$(C_1-C_6)$alkoxy,
$(C_1-C_3)$haloalkyl,
$(C_1-C_3)$haloalkoxy,
cyano, and
$(C_1-C_6)$alkylthio;
and pharmaceutically acceptable salts thereof;
provided that when R and $R^2$ are H and X is $CO_2H$, then $R_1$ is not H, methyl, or ethyl, and further provided that the Formula (I) compound is not

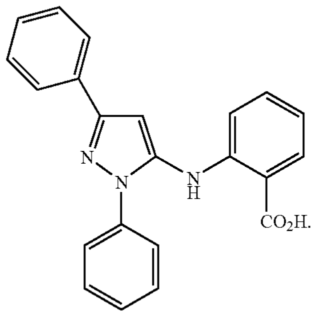

2. The compound of claim 1, wherein $R^1$ is phenyl optionally substituted with up to four substituents selected from the group consisting of
halo,
$(C_1-C_6)$alkyl optionally substituted with one $(C_1-C_4)$ alkoxy,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio;

and

R, $R^2$, $R^3$, $R^4$, $R^5$, $R^6$, $R^7$, $R^8$, X, and n are as defined in claim 1.

3. The compound of claim 1, wherein $R^2$ is
phenyl optionally substituted with up to four substituents selected from the group consisting of
$(C_1-C_6)$alkyl optionally substituted with one $(C_1-C_4)$ alkoxy,
$(C_1-C_6)$alkoxy,
hydroxy,
$NR^8R^8$,
cyano,
$(C_1-C_6)$alkylthio,
halo,
$CO_2R^8$,
$(C_1-C_3)$haloalkoxy,
$(C_1-C_4)$acyl, and
benzoyl;

and

R, $R^1$, $R^3$, $R^4$, $R^5$, $R^6$, $R^7$, $R^8$, X, and n are as defined in claim 1.

4. The compound of claim 1, wherein

X is $CO_2R^8$;

and

R, $R^1$, $R^2$, $R^3$, $R^4$, $R^8$, and n are as defined in claim 1.

5. The compound of claim 1, wherein $R^1$ is phenyl optionally substituted with up to four substituents selected from the group consisting of
halo,
$(C_1-C_6)$alkyl optionally substituted with one $(C_1-C_4)$ alkoxy,
$(C_1-C_6)$alkoxy,
$(C_1-C_3)$haloalkyl,
$(C_1-C_3)$haloalkoxy,
$NR^8R^8$,
cyano, and
$(C_1-C_6)$alkylthio;

$R^2$ is H,
halo,
$(C_1-C_6)$alkyl optionally substituted with one $(C_1-C_4)$ alkoxy,
$(C_3-C_6)$cycloalkyl optionally substituted with up to two substituents selected from the group consisting of $(C_1-C_3)$alkyl and halo, or
$(C_1-C_3)$haloalkyl;

and

R, $R^3$, $R^4$, $R^5$, $R^6$, $R^7$, $R^8$, X, and n are as defined in claim 1.

6. The compound of claim 1, wherein $R^1$ is H,
$(C_1-C_6)$alkyl optionally substituted with one substituent selected from the group consisting of $(C_1-C_4)$ alkoxy, phenyl optionally substituted with halo, and [tri$(C_1-C_4)$alkyl]silyl,
$(C_3-C_6)$alkenyl,
$(C_3-C_6)$alkynyl,
$(C_3-C_6)$cycloalkyl optionally substituted with up to two substituents selected from the group consisting of $(C_1-C_3)$alkyl, $CF_3$, and halo, or
$(C_1-C_3)$haloalkyl;

$R^2$ is H,
halo,
$(C_1-C_6)$alkyl optionally substituted with one $(C_1-C_4)$ alkoxy,
$(C_3-C_6)$cycloalkyl optionally substituted with up to two substituents selected from the group consisting of $(C_1-C_3)$alkyl and halo, or
$(C_1-C_3)$haloalkyl;

and

R, $R^3$, $R^4$, $R^5$, $R^6$, $R^7$, $R^8$, X, and n are as defined in claim 1.

7. The compound of claim 1, wherein $R^1$ is H,
$(C_1-C_6)$alkyl optionally substituted with one substituent selected from the group consisting of $(C_1-C_4)$ alkoxy, phenyl optionally substituted with halo, and [tri$(C_1-C_4)$alkyl]silyl,
$(C_3-C_6)$alkenyl,
$(C_3-C_6)$alkynyl,
$(C_3-C_6)$cycloalkyl optionally substituted with up to two substituents selected from the group consisting of $(C_1-C_3)$alkyl, $CF_3$, and halo, or
$(C_1-C_3)$haloalkyl;

$R^2$ is
phenyl optionally substituted with up to four substituents selected from the group consisting of
$(C_1-C_6)$alkyl optionally substituted with one $(C_1-C_4)$ alkoxy,
$(C_1-C_6)$alkoxy,
hydroxy,
$NR^8R^8$,
cyano,
$(C_1-C_6)$alkylthio,
halo,
$CO_2R^8$,
$(C_1-C_3)$haloalkoxy,
$(C_1-C_4)$acyl, and
benzoyl;

and

R, $R^3$, $R^4$, $R^5$, $R^6$, $R^7$, $R^8$, X, and n are as defined in claim 1.

8. The compound of claim 1, wherein $R^1$ is phenyl optionally substituted with up to four substituents selected from the group consisting of
halo, ($C_1$-$C_6$)alkyl optionally substituted with one ($C_1$-$C_4$) alkoxy, ($C_1$-$C_6$)alkoxy, ($C_1$-$C_3$)haloalkyl, ($C_1$-$C_3$)haloalkoxy, $NR^8R^8$, cyano, and ($C_1$-$C_6$)alkylthio;

$R^2$ is H, halo, ($C_1$-$C_6$)alkyl optionally substituted with one ($C_1$-$C_4$) alkoxy, ($C_3$-$C_6$)cycloalkyl optionally substituted with up to two substituents selected from the group consisting of ($C_1$-$C_3$)alkyl and halo, or ($C_1$-$C_3$)haloalkyl;

X is $CO_2R^8$;

and

R, $R^3$, $R^4$, $R^8$, and n are as defined in claim 1.

9. The compound of claim 1, wherein $R^1$ is H, ($C_1$-$C_6$)alkyl optionally substituted with one substituent selected from the group consisting of ($C_1$-$C_4$) alkoxy, phenyl optionally substituted with halo, and [tri($C_1$-$C_4$)alkyl]silyl, ($C_3$-$C_6$)alkenyl, ($C_3$-$C_6$)alkynyl, ($C_3$-$C_6$)cycloalkyl optionally substituted with up to two substituents selected from the group consisting of ($C_1$-$C_3$)alkyl, $CF_3$, and halo, or ($C_1$-$C_3$)haloalkyl;

$R^2$ is H, halo, ($C_1$-$C_6$)alkyl optionally substituted with one ($C_1$-$C_4$) alkoxy, ($C_3$-$C_6$)cycloalkyl optionally substituted with up to two substituents selected from the group consisting of ($C_1$-$C_3$)alkyl and halo, or ($C_1$-$C_3$)haloalkyl;

X is $CO_2R^8$;

and

R, $R^3$, $R^4$, $R^8$, and n are as defined in claim 1.

10. The compound of claim 1, wherein $R^1$ is H, ($C_1$-$C_6$)alkyl optionally substituted with one substituent selected from the group consisting of ($C_1$-$C_4$) alkoxy, phenyl optionally substituted with halo, and [tri($C_1$-$C_4$)alkyl]silyl, ($C_3$-$C_6$)alkenyl, ($C_3$-$C_6$)alkynyl, ($C_3$-$C_6$)cycloalkyl optionally substituted with up to two substituents selected from the group consisting of ($C_1$-$C_3$)alkyl, $CF_3$, and halo, or ($C_1$-$C_3$)haloalkyl;

$R^2$ is phenyl optionally substituted with up to four substituents selected from the group consisting of ($C_1$-$C_6$)alkyl optionally substituted with one ($C_1$-$C_4$) alkoxy, ($C_1$-$C_6$)alkoxy, hydroxy, $NR^8R^8$, cyano, ($C_1$-$C_6$)alkylthio, halo, $CO_2R^8$, ($C_1$-$C_3$)haloalkoxy, ($C_1$-$C_4$)acyl, and benzoyl;

X is $CO_2R^8$;

and

R, $R^3$, $R^4$, $R^8$, and n are as defined in claim 1.

11. The compound of claim 1, wherein

R is H;

$R^1$ is H, ($C_1$-$C_6$)alkyl optionally substituted with one substituent selected from the group consisting of ($C_1$-$C_4$) alkoxy, phenyl optionally substituted with halo, and [tri($C_1$-$C_4$)alkyl]silyl, ($C_3$-$C_6$)cycloalkyl optionally substituted with up to two substituents selected from the group consisting of ($C_1$-$C_3$)alkyl, $CF_3$, and halo, ($C_1$-$C_3$)haloalkyl, or phenyl optionally substituted with up to four substituents selected from the group consisting of halo, ($C_1$-$C_6$)alkyl optionally substituted with one ($C_1$-$C_4$) alkoxy, ($C_1$-$C_6$)alkoxy, ($C_1$-$C_3$)haloalkyl, ($C_1$-$C_3$)haloalkoxy, $NR^8R^8$, cyano, and ($C_1$-$C_6$)alkylthio;

$R^2$ is H, ($C_1$-$C_6$)alkyl optionally substituted with one ($C_1$-$C_4$) alkoxy, phenyl optionally substituted with up to four substituents selected from the group consisting of ($C_1$-$C_6$)alkyl optionally substituted with one ($C_1$-$C_4$) alkoxy, ($C_1$-$C_6$)alkoxy, hydroxy, $NR^8R^8$, cyano, ($C_1$-$C_6$)alkylthio, halo, $CO_2R^8$, ($C_1$-$C_3$)haloalkoxy, ($C_1$-$C_4$)acyl, and benzoyl;

$R^3$ is ($C_1$-$C_6$)alkyl, ($C_3$-$C_6$)cycloalkyl, or phenyl optionally substituted with up to four substituents selected from the group consisting of ($C_1$-$C_6$)alkyl optionally substituted with one ($C_1$-$C_4$) alkoxy, halo, ($C_1$-$C_3$)haloalkyl, ($C_1$-$C_6$)alkoxy, ($C_1$-$C_3$)haloalkoxy $NR^8R^8$, cyano, ($C_1$-$C_6$)alkylthio, and $SO_2$($C_1$-$C_3$)alkyl;

$R^4$ is ($C_1$-$C_6$)alkyl optionally substituted with one ($C_1$-$C_4$)alkoxy, ($C_1$-$C_6$)alkoxy, halo, phenyl optionally substituted with up to four substituents selected from the group consisting of halo, ($C_1$-$C_6$)alkyl optionally substituted with one ($C_1$-$C_4$) alkoxy, (C$_1$-C$_6$)alkoxy,
(C$_1$-C$_3$)haloalkyl,
(C$_1$-C$_3$)haloalkoxy,
NR$^8$R$^8$,
cyano, and
(C$_1$-C$_6$)alkylthio;
n=0, 1, 2, or 3;
X is CO$_2$R$^8$; and
R$^8$ is H,
(C$_1$-C$_6$)alkyl,
benzyl optionally substituted on the aryl ring with up to four substituents selected from the group consisting of
halo,
(C$_1$-C$_6$)alkyl optionally substituted with one (C$_1$-C$_4$) alkoxy,
(C$_1$-C$_3$)alkoxy,
(C$_1$-C$_3$)haloalkyl,
(C$_1$-C$_3$)haloalkoxy,
cyano, and
(C$_1$-C$_6$)alkylthio, or
phenyl optionally substituted with up to four substituents selected from the group consisting of
(C$_1$-C$_6$)alkyl optionally substituted with one (C$_1$-C$_4$) alkoxy,
halo,
(C$_1$-C$_6$)alkoxy,
(C$_1$-C$_3$)haloalkyl,
(C$_1$-C$_3$)haloalkoxy,
cyano, and
(C$_1$-C$_6$)alkylthio.

12. The compound of claim 1, wherein
R is H;
R$^1$ is H,
(C$_1$-C$_6$)alkyl optionally substituted with one substituent selected from the group consisting of (C$_1$-C$_4$) alkoxy, phenyl optionally substituted with halo, and [tri(C$_1$-C$_4$)alkyl]silyl, or
phenyl optionally substituted with up to four substituents selected from the group consisting of
halo,
(C$_1$-C$_6$)alkyl optionally substituted with one (C$_1$-C$_4$) alkoxy,
(C$_1$-C$_6$)alkoxy,
(C$_1$-C$_3$)haloalkyl,
(C$_1$-C$_3$)haloalkoxy,
NR$^8$R$^8$,
cyano, and
(C$_1$-C$_6$)alkylthio;
R$^2$ is H,
halo, or
(C$_1$-C$_6$)alkyl optionally substituted with one (C$_1$-C$_4$) alkoxy;
R$^3$ is (C$_1$-C$_6$)alkyl,
or
phenyl optionally substituted with up to four substituents selected from the group consisting of
(C$_1$-C$_6$)alkyl optionally substituted with one (C$_1$-C$_4$) alkoxy,
halo,
(C$_1$-C$_3$)haloalkyl,
(C$_1$-C$_6$)alkoxy,
(C$_1$-C$_3$)haloalkoxy
NR$^8$R$^8$,
cyano,
(C$_1$-C$_6$)alkylthio, and
SO$_2$(C$_1$-C$_3$)alkyl;
R$^4$ is (C$_1$-C$_6$)alkyl optionally substituted with one (C$_1$-C$_4$)alkoxy,
(C$_1$-C$_6$)alkoxy,
(C$_1$-C$_6$)alkylthio,
(C$_1$-C$_3$)haloalkyl,
(C$_1$-C$_3$)haloalkoxy,
halo;
n=0, 1, 2, or 3;
X is CONR$^5$R$^6$;
R$^5$ is H,
(C$_1$-C$_6$)alkyl,
(C$_2$-C$_6$)alkyl substituted with OR$^6$,
benzyl optionally substituted on the aryl ring with up to four substituents selected from the group consisting of
halo,
(C$_1$-C$_6$)alkyl optionally substituted with one (C$_1$-C$_4$) alkoxy,
(C$_1$-C$_6$)alkoxy,
(C$_1$-C$_3$)haloalkyl,
(C$_1$-C$_3$)haloalkoxy,
NR$^8$R$^8$,
cyano, and
(C$_1$-C$_6$)alkylthio,
phenyl optionally substituted with up to four substituents selected from the group consisting of
(C$_1$-C$_6$)alkyl optionally substituted with one (C$_1$-C$_4$) alkoxy,
halo,
(C$_1$-C$_6$)alkoxy,
(C$_1$-C$_3$)haloalkyl,
(C$_1$-C$_3$)haloalkoxy,
NR$^8$R$^8$,
cyano, and
(C$_1$-C$_6$)alkylthio,
or
SO$_2$-phenyl said phenyl optionally substituted with up to four substituents selected from the group consisting of
halo
(C$_1$-C$_6$)alkyl optionally substituted with one (C$_1$-C$_4$) alkoxy,
(C$_1$-C$_6$)alkoxy,
(C$_1$-C$_3$)haloalkyl,
(C$_1$-C$_3$)haloalkoxy,
NR$^8$R$^8$,
cyano, and
(C$_1$-C$_6$)alkylthio;
R$^6$ is H or (C$_1$-C$_6$)alkyl;
and
R$^8$ is H,
(C$_1$-C$_6$)alkyl,
benzyl optionally substituted on the aryl ring with up to four substituents selected from the group consisting of
halo,
(C$_1$-C$_6$)alkyl optionally substituted with one (C$_1$-C$_4$) alkoxy,
(C$_1$-C$_3$)alkoxy,
(C$_1$-C$_3$)haloalkyl,
(C$_1$-C$_3$)haloalkoxy,
cyano, and
(C$_1$-C$_6$)alkylthio,
or
phenyl optionally substituted with up to four substituents selected from the group consisting of (C$_1$-C$_6$)alkyl optionally substituted with one (C$_1$-C$_4$) alkoxy,
halo,
(C$_1$-C$_6$)alkoxy,
(C$_1$-C$_3$)haloalkyl,
(C$_1$-C$_3$)haloalkoxy,
cyano, and
(C$_1$-C$_6$)alkylthio.

13. The compound of claim 1 selected from the group consisting of

2-[(3-tert-butyl-1-methyl-1H-pyrazol-5-yl)amino]-5-methoxybenzoic acid;
2-{[3-methyl-1-(2-methylphenyl)-1H-pyrazol-5-yl]amino}benzamide;
2-{[3-(4-fluorophenyl)-1-(2-methylphenyl)-1H-pyrazol-5-yl]amino}benzoic acid;
2-{[3-tert-butyl-1-(2-methylphenyl)-1H-pyrazol-5-yl]amino}-5-methoxybenzoic acid;
2-{[3-tert-butyl-1-(2-methoxyphenyl)-1H-pyrazol-5-yl]amino}-5-methoxybenzoic acid;
2-[(1,3-diphenyl-1H-pyrazol-5-yl)amino]-5-methoxybenzoic acid;
2-fluoro-6-{[3-(4-fluorophenyl)-1-(2-methylphenyl)-1H-pyrazol-5-yl]amino}benzoic acid;
2-fluoro-6-{[1-(2-methylphenyl)-3-(4-methylphenyl)-1H-pyrazol-5-yl]amino}benzoic acid;
2-{[3-tert-butyl-1-(5-fluoro-2-methylphenyl)-1H-pyrazol-5-yl]amino}-6-fluorobenzoic acid;
2-({3-tert-butyl-1-[2-(methylthio)phenyl]-1H-pyrazol-5-yl}amino)-5-methoxybenzoic acid;
2-{[3-tert-butyl-1-(2-ethoxyphenyl)-1H-pyrazol-5-yl]amino}benzoic acid;
2-{[3-tert-butyl-1-(2-ethoxyphenyl)-1H-pyrazol-5-yl]amino}-5-methoxybenzoic acid;
2-{[3-(3-methoxyphenyl)-1-(2-methylphenyl)-1H-pyrazol-5-yl]amino}benzoic acid;
5-methoxy-2-{[3-(3-methoxyphenyl)-1-(2-methylphenyl)-1H-pyrazol-5-yl]amino}benzoic acid;
2-{[3-(3-methoxyphenyl)-1-(2-methylphenyl)-1H-pyrazol-5-yl]amino}-5-methylbenzoic acid;
2-{[3-tert-butyl-1-(2-methoxyphenyl)-4-methyl-1H-pyrazol-5-yl]amino}-5-methoxybenzoic acid;
2-[(3-tert-butyl-1-phenyl-1H-pyrazol-5-yl)amino]-5-methoxybenzoic acid;
2-{[3-tert-butyl-1-(5-fluoro-2-methylphenyl)-1H-pyrazol-5-yl]amino}benzoic acid;
2-{[3-tert-butyl-1-(2,6-dimethylphenyl)-1H-pyrazol-5-yl]amino}benzoic acid;
2-{[3-tert-butyl-1-(2-methoxy-5-methylphenyl)-1H-pyrazol-5-yl]amino}benzoic acid;
2-{[3-tert-butyl-1-(2,3-dimethylphenyl)-1H-pyrazol-5-yl]amino}-5-methoxybenzoic acid;
2-{[3-tert-butyl-1-(2-methoxy-6-methylphenyl)-1H-pyrazol-5-yl]amino}-5-methoxybenzoic acid;
2-{[3-tert-butyl-1-(2,6-dimethylphenyl)-1H-pyrazol-5-yl]amino}-5-methoxybenzoic acid;
2-{[1-(2,6-dimethylphenyl)-3-(1-methylcyclopropyl)-1H-pyrazol-5-yl]amino}benzoic acid;
5) 2-{[1-(2,6-dimethylphenyl)-3-(3,3,3-trifluoropropyl)-1H-pyrazol-5-yl]amino}-5-methoxybenzoic acid;
5-methoxy-2-{[3-methyl-1-(2-methylphenyl)-4-phenyl-1H-pyrazol-5-yl]amino}benzoic acid;
5-methoxy-2-{[1-(2-methylphenyl)-4-pyridin-4-yl-3-(trifluoromethyl)-1H-pyrazol-5-yl]amino}benzoic acid;
5-methoxy-2-{[4-(4-methoxyphenyl)-1-(2-methylphenyl)-3-(trifluoromethyl)-1H-pyrazol-5-yl]amino}benzoic acid;
2-{[4-(2-fluorophenyl)-3-methyl-1-(2-methylphenyl)-1H-pyrazol-5-yl]amino}-5-methoxybenzoic acid;
5-methoxy-2-{[1-(2-methoxyphenyl)-3-methyl-4-phenyl-1H-pyrazol-5-yl]amino}benzoic acid; and
2-{[4-(2,4-dimethoxyphenyl)-3-methyl-1-(2-methylphenyl)-1H-pyrazol-5-yl]amino}-5-methoxybenzoic acid.

14. A pharmaceutical composition comprising a therapeutically effective amount of a compound of claim 1, or a pharmaceutically acceptable salt, in combination with a pharmaceutically acceptable carrier.

15. A pharmaceutical composition comprising a therapeutically effective amount of a compound of claim 1, or a pharmaceutically acceptable salt thereof, in combination with a pharmaceutically acceptable carrier and one or more pharmaceutical agents.

16. The pharmaceutical composition of claim 15, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, anti-obesity agents, HMG CoA reductase inhibitors, nicotinic acid, bile acid sequestrants, fibric acid derivatives, and anti-hypertensive agents.

17. A composition comprising an effective amount of a compound of claim 1, or a salt thereof, in combination with an inert carrier.

18. A method of treating diabetes comprising the step of administering to a subject in need thereof a therapeutically effective amount of a compound of claim 1.

19. The method of claim 18, wherein said diabetes is selected from the group consisting of type 1 diabetes, type 2 diabetes, maturity-onset diabetes of the young, latent autoimmune diabetes adult, and gestational diabetes.

20. A method of treating Syndrome X comprising the step of administering to a subject in need thereof a therapeutically effective amount of a compound of claim 1.

21. A method of treating diabetes-related disorders comprising the step of administering to a subject in need thereof a therapeutically effective amount of a compound of claim 1.

22. The method of claim 21, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

23. A method of treating obesity comprising the step of administering to a subject in need thereof a therapeutically effective amount of a compound of claim 1.

24. A method of treating cardiovascular diseases comprising the step of administering to a subject in need thereof a therapeutically effective amount of a compound of claim 1.

25. A method of treating diabetes comprising the step of administering to a subject in need thereof a therapeutically effective amount of a compound of claim 1 in combination with one or more pharmaceutical agents.

26. The method of claim 25, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

27. The method of claim 25, wherein said diabetes is selected from the group consisting of type 1 diabetes, type 2 diabetes, maturity-onset diabetes of the young, latent autoimmune diabetes adult, and gestational diabetes.

28. A method of treating Syndrome X comprising the step of administering to a subject in need thereof a therapeutically effective amount of a compound of claim 1 in combination with one or more pharmaceutical agents.

29. The method of claim 28, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

30. A method of treating diabetes-related disorders comprising the step of administering to a subject in need thereof a therapeutically effective amount of a compound of claim 1 in combination with one or more pharmaceutical agents.

31. The method of claim 30, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

32. The method of claim 30, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

33. A method of treating diabetes, Syndrome X, or diabetes-related disorders comprising the step of administering to a subject in need thereof a therapeutically effective amount of a compound of claim 1 in combination with one or more agents selected from the group consisting of HMG CoA reductase inhibitors, nicotinic acid, bile acid sequestrants, fibric acid derivatives, and anti-hypertensive agents.

34. The method of claim 33, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

35. The method of any one of claims 25 to 34, wherein the compound of claim 1 and one or more pharmaceutical agents are administered as a single pharmaceutical dosage formulation.

36. A method of treating or preventing secondary causes of diabetes comprising the step of administering to a subject in need thereof a therapeutically effective amount of a compound of claim 1.

37. The method of claim 36, wherein said secondary cause is selected from the group consisting of glucocorticoid excess, growth hormone excess, pheochromocytoma, and drug-induced diabetes.

38. A method of treating or preventing secondary causes of diabetes comprising the step of administering a subject in need thereof a therapeutically effective amount of a compound of claim 1 in combination with one or more pharmaceutical agents.

39. The method of claim 38, wherein said pharmaceutical agent is selected from the group consisting of PPAR agonists, sulfonylurea drugs, non-sulfonylurea secretagogues, α-glucosidase inhibitors, insulin sensitizers, insulin secretagogues, hepatic glucose output lowering compounds, insulin, and anti-obesity agents.

40. A method of stimulating insulin secretion in a subject in need thereof by administering to said subject a compound of claim 1.

* * * * *